US008426569B2

(12) United States Patent
Hirao et al.

(10) Patent No.: US 8,426,569 B2
(45) Date of Patent: Apr. 23, 2013

(54) DNA CAPABLE OF BEING AMPLIFIED BY PCR WITH HIGH SELECTIVITY AND HIGH EFFICIENCY

(75) Inventors: Ichiro Hirao, Komae (JP); Michiko Hirao, Yokohama (JP); Shigeyuki Yokoyama, Yokohama (JP)

(73) Assignees: Riken, Wako-Shi (JP); Tagcyx Biotechnologies, Yokohama-Shi (JP)

( * ) Notice: Subject to any disclaimer, the term of this patent is extended or adjusted under 35 U.S.C. 154(b) by 0 days.

(21) Appl. No.: 12/934,066

(22) PCT Filed: Mar. 31, 2009

(86) PCT No.: PCT/JP2009/056718
§ 371 (c)(1),
(2), (4) Date: Nov. 16, 2010

(87) PCT Pub. No.: WO2009/123216
PCT Pub. Date: Oct. 8, 2009

(65) Prior Publication Data
US 2011/0053782 A1   Mar. 3, 2011

(30) Foreign Application Priority Data

Mar. 31, 2008   (JP) ................................. 2008-094255

(51) Int. Cl.
*C07H 21/02*   (2006.01)
*C07H 21/00*   (2006.01)
*C07H 19/044*   (2006.01)
*C07H 19/052*   (2006.01)

(52) U.S. Cl.
USPC ....... 536/23.1; 536/25.3; 536/25.4; 536/26.6; 536/26.9

(58) Field of Classification Search ........................ None
See application file for complete search history.

(56) References Cited

U.S. PATENT DOCUMENTS

2006/0263771 A1   11/2006   Hirao et al.
2007/0105099 A1    5/2007   Prudent et al.

FOREIGN PATENT DOCUMENTS

| EP | 1544294 A1 | 6/2005 |
| EP | 1816130 A1 | 8/2007 |
| EP | 1921141 A1 | 5/2008 |
| EP | 1970445 A1 | 9/2008 |
| JP | 200761087 A | 3/2007 |
| WO | WO-01/05801 A1 | 1/2001 |
| WO | WO-2004/007713 A1 | 1/2004 |
| WO | WO-2005/026187 A1 | 3/2005 |
| WO | WO-2006049297 A | 5/2006 |
| WO | WO-2007066737 A1 | 6/2007 |

OTHER PUBLICATIONS

Hirao et al., Development of an unnatural base pair for efficient PCR amplification; Nucleic Acids Symposium Series, No. 51, 9-10, 2007.*
Stahl et al., Solid phase DNA sequencing using the biotin-avidin system; NAR, vol. 16, No. 7, pp. 3027-3038, 1988.*
Benner, Steven A. et al., "Did the RNA World Exploit an Expanded Genetic Alphabet?" The RNA World, Second Edition, pp. 163-181, (1999).
Henry, Allison A. et al., "Beyond A, C, G and T: Augmenting Nature's Alphabet," Current Opinion in Chemical Biology, vol. 7, pp. 727-733, (2003).
Moser, Michael J. et al., "Enzymatic Repair of an Expanded Genetic Information System," Nucleic Acids Research, vol. 31, No. 17, pp. 5048-5053, (2003).
Bergstrom, Donald E., "Orthogonal Base Pairs Continue to Evolve," Chemistry & Biology, vol. 11, pp. 18-20, (2004).
Benner, Steven A. et al., "Synthetic Biology," Nature Reviews, vol. 6, pp. 533-543, (2005).
Piccirilli, Joseph A. et al., "Enzymatic Incorporation of a New Base Pair into DNA and RNA Extends the Genetic Alphabet," Nature, vol. 343, pp. 33-37, (1990).
Switzer, Christopher Y. et al., "Enzymatic Recognition of the Base Pair Between Isocytidine and Isoguanosine," Biochemistry, vol. 32, pp. 10489-10496, (1993).
Sismour, A. Michael et al., "PCR Amplification of DNA Containing Non-Standard Base Pairs by Variants of Reverse Transcriptase From Human Immunodeficiency Virus-1," Nucleic Acids Reserach, vol. 32, No. 2, pp. 728-735, (2004).
Johnson, Scott, C. et al., "A Third Base Pair for the Polymerase Chain Reaction: Inserting isoC and isoG," Nucleic Acids Research, vol. 32, No. 6, pp. 1937-1941, (2004).
Ahle, J. David et al., "Sequence Determination of Nucleic Acids Containing 5-metholisocytosine and Isoguanine: Identification and Insight into the Polymerase Replication of the Non-Natural Nucleobases," Nucleic Acids Research, vol. 33, No. 10, pp. 3176-3184, (2005).
Morales, Juan C. et al., "Efficient Replication Between Non-Hydrogen-Bonded Nucleoside Shape Analogs," Nature Structural Biology, vol. 5, No. 11, pp. 950-954, (1998).
Kool, Eric T. et al., "Mimicking the Structure and Function of DNA: Insights into DNA Stability and Replication," Agnew. Chem. Int., Edition 39, pp. 990-1009, (2000).

(Continued)

*Primary Examiner* — Celine Qian
*Assistant Examiner* — Addison D Ault
(74) *Attorney, Agent, or Firm* — Birch, Stewart, Kolasch & Birch, LLP

(57) ABSTRACT

The present invention relates to unnatural base pairs of Ds (a 7-(2 thienyl)-3H-imidazo[4,5-b]pyridine-3-yl group) and a Pa derivative (a 2-nitro-1H-pyrrole-1-yl group bearing a substituent having a π-electron system attached at position 4) that can be replicated with high selectivity/high efficiency, and methods for replicating nucleic acids containing the unnatural base pairs. The present invention also relates to methods for incorporating an unnatural base bearing a functional substituent attached thereto into DNA by a nucleic acid replication reaction. The present invention also relates to methods for replicating and selectively collecting a nucleic acid containing an unnatural base pair from a nucleic acid pool. The present invention also relates to methods for determining a sequence of natural bases in the proximity of an unnatural base in DNA for achieving highly efficient and highly selective replication of a nucleic acid containing the unnatural base.

18 Claims, 9 Drawing Sheets

OTHER PUBLICATIONS

McMinn, Dustin L. et al., "Efforts Toward Expansion of the Genetic Alphabet: DNA Polymerase Recognition of a Highly Stable, Self-Pairing Hydrophobic Base," Journal of the American Chemical Society, vol. 121, No. 49, pp. 11585-11586, (1999).

Wu, Yiqin et al., "Efforts Toward the Expansion of the Genetic Alphabet: Optimization of Interbase Hydrophobic Interactions," Journal of American Chemical Society, vol. 122, No, 32, pp. 7621-7632, (2000).

Ogawa, Anthony K. et al., "Efforts Toward the Expansion of the Genetic Alphabet: Information Storage and Replication with Unnatural Hydrophobic Base Pairs," Journal of the American Chemistry Society, vol. 122, No. 14, pp. 3274-3287, (2000).

Fujiwara, Tsuyoshi et al., "Synthesis of 6-(2-Thienyl)purine Nucleoside Derivatives That Form Unnatural Base Pairs with Pyridin-2-one Nucleosides," Bioorganic & Medicinal Chemistry Letters, vol. 11, pp. 2221-2223, (2001).

Hiroo, Ichiro et al., "An Unnatural Base Pair for Incorporating Amino Acid Analogs into Proteins," Nature Biotechnology, vol. 20, pp. 177-182, (2002).

Mitsui, Tsuneo at al., "An Efficient Unnatural Base Pair for a Base-Pair-Expanded Transcription System," Journal of the American Chemistry Society, vol. 127, No. 24, pp. 8652-8658, (2005).

Kimoto, Michiko et al., "Site-Specific Incorporation of a Photo-Crosslinking Component into RNA by T7 Transcription Mediated by Unnatural Base Pairs," Chemistry & Biology, vol. 11, pp. 47-55, (2004).

Moriyama, Kai et al., "Site-Specific Biotinylation of RNA Molecules by Transcription Using Unnatural Base Pairs," Nucleic Acids Research, vol. 33, No. 15, e.129, pp. 1-8, (2005).

Kawai, Rie et al., "Site-Specific Fluorescent Labeling of RNA Molecules by Specific Transcription Using Unnatural Base Pairs," Journal of the American Chemistry Society, vol. 127, No, 49, pp. 17286-17295, (2005).

Yang, Zunyi et al., "Enzymatic Incorporation of a Third Nucleobase Pair," Nucleic Acids Research, vol. 35, No. 13, pp. 4238-4249, (2007).

Hirao, Ichiro et al., "An Unnatural Hydrophobic Base Pair System: Site-Specific Incorporation of Nucleotide Analogs into DNA and RNA," Nature Methods, vol. 3, No. 9, pp. 729-735, (2006).

Hirao, Ichiro at al., "An Efficient Unnatural Base Pair for PCR Amplification," Journal of the American Chemistry Society, vol. 129, No. 50, pp. 15549-15555, (2007).

Kimoto, Michiko at al., "Efficient PCR Amplification by an Unnatural Base Pair System," Nucleic Acids Symposium Series, No. 52, pp. 469-470, (2008).

Kimoto, Michiko et al., "Sequences Around the Unnatural Base Pair in DNA Templates for Efficient Replication," Nucleic Acids Symposium Series, No. 52, pp. 457-458, 2008.

Kimoto, Michiko et al., "Development of an Unnatural Base Pair System for Efficient PCR Amplification," Dai 81 Kai Nippon Seika Gakkai Taikai Dai 31 Kai Nippon Burnshi Seibutsu Gakkai Nankai Godo Taikai Program Koen Yoshishu, pp. 1468-1469, (2008).

Hirao, I., et al., "Development of an unnatural base pair for efficient PCR amplification," Nucleic Acids Symposium Series, No. 51, pp. 9-10 (2007).

Supplementary European Search Report issued in corresponding EP Application No. 09728695.9 dated Jul. 13, 2012.

* cited by examiner

US 8,426,569 B2

DNA CAPABLE OF BEING AMPLIFIED BY PCR WITH HIGH SELECTIVITY AND HIGH EFFICIENCY

This application is the National Stage phase under 35 U.S.C. §371 of International Application No. PCT/JP2009/056718 filed on Mar. 31, 2009, which claims priority under 35 U.S.C. §119(a)-(d) of Foreign Application No. 2008-094255 filed on Mar. 31, 2008 in Japan.

TECHNICAL FIELD

The present invention relates to unnatural base pairs capable of being replicated with high selectivity/high efficiency, and methods for replicating nucleic acids containing such unnatural base pairs. The present invention also relates to methods for incorporating an unnatural base bearing a functional substituent attached thereto into DNA by a nucleic acid replication reaction. The present invention also relates to methods for replicating and selectively collecting a nucleic acid containing an unnatural base pair from a nucleic acid pool. The present invention also relates to methods for determining a sequence of natural bases in the proximity of an unnatural base in DNA so as to achieve highly efficient and highly selective replication of a nucleic acid containing the unnatural base.

BACKGROUND ART

Nucleic acids amplify by self-complementarity of A-T (U) and G-C base pairs, and function as catalysts and ligands. However, the functions of DNA and RNA molecules are restricted by a limitation in number, which is a result of a fact that natural nucleic acids are formed of nucleotides consisting of only four bases as compared with the twenty different amino acids in natural proteins. Unnatural base pair systems offer a solution to this problem because they can be used for addition to kind of bases of nucleic acids and thereby expand genetic information (non-patent documents 1-5). Unnatural base pairs are required to have high specific complementarity allowing for site-specific incorporation of specific nucleotide analogs into DNA and RNA via a polymerase catalytic reaction. If this became possible, the current genetic engineering limited by the number of naturally occurring bases could be replaced by a novel technique using an unnatural base pair system.

The first attempt to generate an unnatural base pair was made by Benner et al. (non-patent documents 6-7). They developed several unnatural base pairs having different hydrogen-binding patterns from those of natural base pairs, such as isoguanine-isocytosine (isoG-isoC) and xanthosine-diaminopyrimidine. Recently, these unnatural base pairs were applied to PCR amplification of DNA fragments containing such base pairs (non-patent documents 8-9), and sequence analysis (non-patent document 10). However, fidelity was relatively moderate, and/or required application of a complex procedure.

Subsequently, Kool et al. synthesized hydrophobic bases having similar shapes to those of natural bases but lacking an ability to form hydrogen bonds in base pairing (non-patent documents 11-12). These hydrophobic bases were selectively recognized by DNA polymerases, which recognition is suggestive of an importance of geometric complementarity between base pairs rather than hydrogen bonding interaction in replication. Recently, a series of hydrophobic base pairs were developed by Romesberg et al., and these base pairs were complementarily incorporated into DNA by Klenow fragment of DNA polymerase I derived from E. coli (non-patent documents 13-15). However, the hydrophobic bases caused non-specific incorporation between the hydrophobic bases in replication without following geometrical complementarity (non-patent document 14).

By combining the concepts of hydrogen bonding pattern and geometric complementarity, the present inventors were able to develop unnatural base pairs between 2-amino-6-(2-thienyl) purine (s) and 2-oxopyridine (y) (patent document 1, non-patent documents 16-17), and between 2-amino-6-(2-thiazolyl)purine (v) and y (patent document 2, non-patent document 18). Bulky substituents at position 6 of s and v efficiently inhibited undesirable base pairing with natural bases (non-cognate pairing), and substrates for y and modified y bases (nucleoside 5'-triphosphates) were site-specifically incorporated into RNA by T7RNA polymerase complementarily to s or v in the template. This specific transcription can be practicable as a means for developing functional RNA molecules (non-patent documents 19-21), but the selectivity of the s-y and v-y base pairs in replication is not much higher than the selectivity in transcription (non-patent documents 16, 18).

Unnatural base pairs approaching a commercial level in replication have been reported, such as a P—Z base pair (P: 2-amino-imidazo[1,2-a]-1,3,5-triazine-4(8H)-one and Z: 6-amino-5-nitro-2(1H)-pyrrolidone) of S. A. Benner et al, in U.S. (non-patent document 22); an isoG-isoC base pair of EraGen in U.S. (patent document 3, and non-patent document 9); and a Ds-Pa base pair and a Ds-Pn base pair (wherein Ds means a 7-(2-thienyl)-3H-imidazo[4,5-b]pyridine-3-yl group, Pa means a 2-formyl-1H-pyrrole-1-yl group, and Pn means a 2-nitro-1H-pyrrole-1-yl group, respectively) of Hirao et al, who are also inventors of the present invention (patent document 4, and non-patent documents 23 and 24). However, the unnatural base pairs of Benner et al, and EraGen suffer from a low selectivity in replication, limitation in a number of PCR cycles, and difficulty in detecting minor amounts of DNA. The unnatural base pairs of Hirao et al, have high selectivity, but require use of special substrates for their replication and the PCR amplification efficiency is not significantly high.

The conservation rate of unnatural bases in DNA during one cycle of PCR amplification is 97.5% in the P—Z base pair of Benner et al., ~96% in the isoG-isoC base pair of EraGen, and ~99% in the Ds-Pa base pair and Ds-Pn base pair previously developed by the present inventors. If the conservation rate of unnatural base pairs in PCR is 97.5%, only about 60% ($0.975^{20}$=0.60) of unnatural base pairs exist in the DNA finally amplified after 20 cycles of PCR. Thus, application of the P—Z and isoG-isoC base pairs is not easy for carrying out various techniques that are based on nucleic acid replication/amplification reactions in which only minor (small) amounts of DNA are employed. Moreover, no sequencing method of DNA containing these unnatural base pairs has been reported to have been deployed on a commercial scale.

The Ds-Pa and Ds-Pn base pairs previously developed by the present inventors are assumed to exist at a level of 82% ($0.99^{20}$=0.82) in the DNA amplified by 20 cycles of PCR. However, there is a need to develop base pairs having further higher conservation rates than the Ds-Pa and Ds-Pn base pairs in order to apply them to various techniques based on nucleic acid replication/amplification reactions. Moreover, PCR amplification of DNA containing these unnatural base pairs require the use of somewhat special modified substrates (γ-amidotriphosphate derivatives), thus complicating operation. In addition, the locations of unnatural base pairs in DNA can be confirmed by sequencing, but the results of sequencing may be perturbed depending on a sequence of natural base pairs in the proximity of the unnatural base pairs and is in need of being improved so as to provide increased generality.

PRIOR ART REFERENCES

Patent document 1: International Publication No. WO2001/005801.
Patent document 2: International Publication No. WO2005/026187.
Patent document 3: Specification of Published U.S. Patent Application No. US2007/0105099.
Patent document 4: International Publication No. WO2007/066737
Non-patent document 1: Benner, S. A., Burgstaller, P., Battersby, T. R. & Jurczyk, S. in The RNA World (eds Gesteland, R. F., Cech, T. R. & Atkins, J. F.) 163-181 (Cold Spring Harbor Laboratory Press, Cold Spring Harbor, N.Y., 1999).
Non-patent document 2: Henry, A. A. & Romesberg, F. E. Beyond A, C, G and T: augmenting nature's alphabet. Curr. Opin. Chem. Biol. 7, 727-733 (2003).
Non-patent document 3: Moser, M. J. & Prudent, J. R. Enzymatic repair of an expanded genetic information system. Nucleic Acids Res. 31, 5048-5053 (2003).
Non-patent document 4: Bergstrom, D. E. Orthogonal base pairs continue to evolve. Chem. Biol. 11, 18-20 (2004).
Non-patent document 5: Benner, S. A. & Sismour, A. M. Synthetic biology. Nat. Rev. 6, 533-543 (2005).
Non-patent document 6: Piccirilli, J. A., Krauch, T., Moroney, S. E. & Benner, S. A. Enzymatic incorporation of a new base pair into DNA and RNA extends the genetic alphabet. Nature 343, 33-37 (1990).
Non-patent document 7: Switzer, C. Y., Moroney, S. E. & Benner, S. A. Enzymatic recognition of the base pair between isocytidine and isoguanosine. Biochemistry 32, 10489-10496 (1993).
Non-patent document 8: Sismour, A. M. et al. PCR amplification of DNA containing non-standard base pairs by variants of reverse transcriptase from Human Immunodeficiency Virus-1. Nucleic Acids Res. 32, 728-735 (2004).
Non-patent document 9: Johnson, S. C., Sherrill, C. B., Marshall, D. J., Moser, M. J. & Prudent, J. R. A third base pair for the polymerase chain reaction: inserting isoC and isoG. Nucleic Acids Res. 32, 1937-1941 (2004).
Non-patent document 10: Ahle, J. D., Barr, S., Chin, A. M. & Battersby, T. R. Sequence determination of nucleic acids containing 5-methylisocytosine and isoguanine: identification and insight into polymerase replication of the nonnatural nucleobases. Nucleic Acids Res. 33, 3176-3184 (2005).
Non-patent document 11: Morales, J. C. & Kool, E. T. Efficient replication between non-hydrogen-bonded nucleoside shape analogs. Nat. Struct. Biol. 5, 950-954 (1998).
Non-patent document 12: Kool, E. T., Morales, J. C. & Guckian, K. M. Mimicking the structure and function of DNA: Insights into DNA stability and replication. Angew. Chem. Int. Ed. 39, 990-1009 (2000).
Non-patent document 13: McMinn, D. L. et al. Efforts toward expansion of the genetic alphabet: DNA polymerase recognition of a highly stable, self-pairing hydrophobic base. J. Am. Chem. Soc. 121, 11585-11586 (1999).
Non-patent document 14: Wu, Y. et al. Efforts toward expansion of the genetic alphabet: optimization of interbase hydrophobic interactions. J. Am. Chem. Soc. 122, 7621-7632 (2000).
Non-patent document 15: Ogawa, A. K. et al. Efforts toward the expansion of the genetic alphabet: Information storage and replication with unnatural hydrophobic base pairs. J. Am. Chem. Soc. 122, 3274-3287 (2000).
Non-patent document 16: Fujiwara, T., Kimoto, M., Sugiyama, H., Hirao, I. & Yokoyama, S. Synthesis of 6-(2-thienyl)purine nucleoside derivatives that form unnatural base pairs with pyridin-2-one nucleosides. Bioorg. Med. Chem. Lett. 11, 2221-2223 (2001).
Non-patent document 17: Hirao, I. et al. An unnatural base pair for incorporating amino acid analogs into proteins. Nat. Biotechnol. 20, 177-182 (2002).
Non-patent document 18: Mitsui, T., Kimoto, M., Harada, Y., Yokoyama, S. & Hirao, I. An efficient unnatural base pair for a base-pair-expanded transcription system. J. Am. Chem. Soc. 24, 8652-8658 (2005).
Non-patent document 19: Kimoto M. et al. Site-specific incorporation of a photo-crosslinking component into RNA by T7 transcription mediated by unnatural base pairs. Chem. Biol. 11, 47-55 (2004).
Non-patent document 20: Moriyama, K., Kimoto, M., Mitsui, T., Yokoyama, S. & Hirao, I. Site-specific biotinylation of RNA molecules by transcription using unnatural base pairs. Nucleic Acids Res. 33, e129 (2005).
Non-patent document 21: Kawai, R. et al. Site-specific fluorescent labeling of RNA molecules by specific transcription using unnatural base pairs. J. Am. Chem. Soc. 127, 17286-17295 (2005).
Non-patent document 22: Yang, Z., Sismour, A. M., Sheng, P., Puskar, N. L. & Benner, S. A. Enzymatic incorporation of a third nucleobase pair. Nucleic Acids Res. 35, 4238-4249 (2007).
Non-patent document 23: Hirao, I., Kimoto, M., Mitsui, T., Fujiwara, T., Kawai, R., Sato, A., Harada, Y. & Yokoyama, S. An unnatural hydrophobic base pair system: site-specific incorporation of nucleotide analogs into DNA and RNA. Nat. Methods 3, 729-735 (2006).
Non-patent document 24: Hirao, I., Mitsui, T., Kimoto, M. & Yokoyama, S. An efficient unnatural base pair for PCR amplification. J. Am. Chem. Soc. 129, 15549-15555 (2007).

DISCLOSURE OF THE INVENTION

Problems to be Solved by the Invention

An object of the present invention is to provide an unnatural base pair capable of being replicated with high selectivity/high efficiency, and a method for replicating a nucleic acid containing the unnatural base pair. Another object of the present invention is to provide a method for incorporating the unnatural base bearing a functional substituent attached thereto into DNA by a nucleic acid replication reaction. Still another object of the present invention to provide a method for replicating and selectively collecting a nucleic acid containing the unnatural base pair from a nucleic acid pool. Still another object of the present invention is to provide a method for determining a sequence of a natural base in the proximity of the unnatural base in DNA for achieving highly efficient and highly selective replication of a nucleic acid containing the unnatural base.

Means to Prove the Problems

As a result of intensive and meticulous studies to solve the above problems, the present inventors have conceived of the present invention on the basis of the finding that combinations of 1-propynyl derivatives of the unnatural base Pn and the unnatural base Ds have high selectivity in nucleic acid amplification reaction as compared with the combinations of the 1 unnatural base pairs Ds-Pa and Ds-Pn previously developed (wherein Ds means a 7-(2 thienyl)-3H-imidazo[4,5-b]pyridine-3-yl group, Pn means a 2-nitro-1H-pyrrole-1-yl group, and Pa means a 2-formyl-1H-pyrrole-1-yl group, respectively).

In replication using the conventional unnatural base pair Ds-Pa, PCR amplification was successfully achieved with high selectivity by using modified substrates (nucleoside 5'-γ-amidotriphosphates; hereinafter sometimes referred to as γ-amidotriphosphates) for Ds and A in order to prevent undesirable base pair formation of Ds-Ds and A-Pa (I. Hirao, et al., Nature Methods, 3: 729-735 (2006)). Subsequent replacement of the unnatural base Pa with the unnatural base Pn revealed that the undesirable base pair A-Pn is formed less frequently than A-Pa, thus allowing PCR amplification without using modified substrates (γ-amidotriphosphates) for A (I. Hirao, et al., J. Am. Chem. Soc., 129: 15549-15555 (2007)). However, PCR amplification of those having the unnatural base pair Ds-Pn still required modified substrates (γ-amidotriphosphates) for Ds (WO 2007/066737). This is because the efficiency of undesirable Ds-Ds base pair formation is higher than the efficiency of Ds-Pn base pair formation.

Under the circumstances, the present inventors developed a derivative having a propynyl group, which is one of substituents having a π-electron system for increasing the affinity between the substrate Pn and DNA polymerase, attached to position 4 of Pn. Further, we found that the use of this substrate allows PCR amplification using conventional deoxyribonucleotide 5'-triphosphates as substrates for the bases Ds, Pn derivative, A, G, C and T without requiring modified substrates (γ-amidotriphosphates) for Ds. We further found that unnatural bases having functional compounds (amino group, fluorescent dyes, biotin, etc.) added to the end of the substituent having a π-electron system attached to Pn via linker moieties having various lengths also have high selectivity in nucleic acid amplification reactions. As a result, we conceived the present invention.

The foregoing explanation of the background of the present invention was given for understanding the present invention, but the scope of the present invention is not limited to the foregoing explanation but determined by the appended claims.

The present invention provides the following embodiments 1-19.

EMBODIMENT 1

A method for replicating a nucleic acid containing an unnatural base pair, comprising performing a nucleic acid replication reaction on a template strand consisting of a nucleic acid containing a nucleotide having a base represented by formula I below:

[Formula 1]

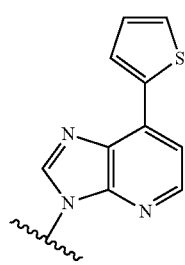

I (hereinafter referred to as Ds), and/or a base represented by formula II below:

[Formula 2]

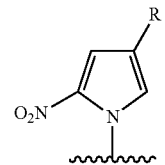

II wherein R is —X—Y,

[Formula 3]

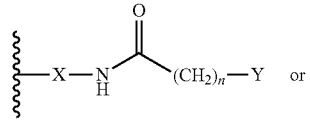

or

[Formula 4]

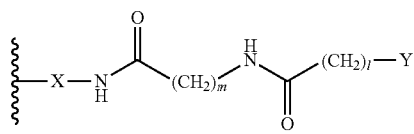

wherein
n is an integer selected from 1 to 12;
m is an integer selected from 1 to 12;
l is an integer selected from 1 to 12;
X is selected from a group consisting of —C≡C—CH$_2$—, —C≡C—, —C=C—, aryl, thienyl, imidazolyl, and thiazolyl;
Y is selected from a group consisting of —CH$_3$, —C$_2$H$_5$, —NH$_2$, —OH, —COOH, —CHO, —SH, a substituted or unsubstituted aryl, —NHCO—Z, —CONH—Z, —NH-CONH—Z, —O—Z, —COO—Z, —O—C(=O)—Z, —CO—Z, and —S—Z, wherein Z is selected from a group consisting of a fluorescent dye, biotin, an antibody-binding compound, a photocrosslinker, a chelating agent, an amino acid and a peptide,
using a substituted or unsubstituted deoxyribonucleoside 5'-triphosphate having the base Ds, a base represented by formula II above, and/or a natural base, as a replication substrate, thereby replicating a nucleic acid containing an unnatural base pair of the base Ds and a base represented by formula II above.

EMBODIMENT 2

The method of embodiment 1 wherein the template strand is a DNA containing at least two nucleotides having the base Ds and/or a base represented by formula II.

EMBODIMENT 3

The method of embodiment 1 or 2 wherein the replication substrate is not a deoxyribonucleoside 5'-triphosphate substituted at the hydroxyl group of the γ-phosphate.

EMBODIMENT 4

The method of any one of embodiments 1 to 3 wherein the fluorescent dye is carboxyfluorescein (FAM).

EMBODIMENT 5

A method for incorporating an unnatural base bearing a functional substituent attached thereto into DNA by a nucleic acid replication reaction, comprising performing a nucleic acid replication reaction on a template strand which is a nucleic acid containing a nucleotide having a base represented by formula I below:

[Formula 5]

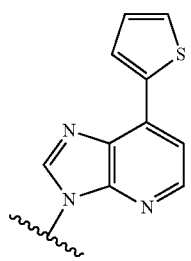

I (hereinafter referred to as Ds) using a substituted or unsubstituted deoxyribonucleoside 5'-triphosphate having a base represented by formula II below:

[Formula 6]

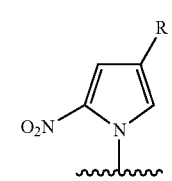

II wherein R is —X—Y,

[Formula 7]

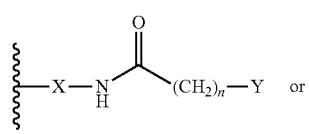

or

[Formula 8]

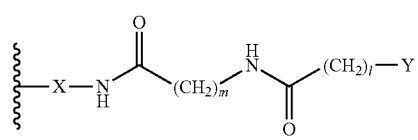

wherein
n is an integer selected from 1 to 12;
m is an integer selected from 1 to 12;
l is an integer selected from 1 to 12;
X is selected from a group consisting of —C≡C—CH$_2$—, —C≡C—, —C=C—, aryl, thienyl, imidazolyl, and thiazolyl;
Y is selected from a group consisting of —CH$_3$, —C$_2$H$_5$, —NH$_2$, —OH, —COOH, —CHO, —SH, a substituted or unsubstituted aryl, —NHCO—Z, —CONH—Z, —NH-CONH—Z, —O—Z, —COO—Z, —O—C(=O)—Z, —CO—Z, and, —S—Z, wherein Z is selected from a group consisting of a fluorescent dye, biotin, an antibody-binding compound, a photocrosslinker, a chelating agent, an amino acid and a peptide; the base Ds, and/or a natural base, as a replication substrate;
thereby generating a nucleic acid containing an unnatural base pair of the base Ds and a base represented by formula II above, whereby an unnatural base bearing a functional substituent attached thereto is incorporated into DNA.

EMBODIMENT 6

The method of embodiment 5 wherein the template strand is a nucleic acid containing at least two nucleotides having the base Ds.

EMBODIMENT 7

The method of embodiment 5 or 6 wherein the replication substrate is not a deoxyribonucleoside 5'-triphosphate substituted at the hydroxyl group of the γ-phosphate.

EMBODIMENT 8

The method of any one of embodiment 5 to 7 wherein the template strand includes a sequence of 5'-N$^1$N$^2$N$^3$(Ds)N$^4$N$^5$N$^6$-3' (SEQ ID NO: 1) as a flanking sequence of the base Ds, wherein N$^1$, N$^2$, N$^3$, N$^5$, N$^6$ are nucleotides having a natural base, provided that it satisfies at least two or more selected from the group consisting of the following criteria:
(a) N$^1$ is thymine (T) or cytosine (C);
(b) N$^3$ is cytosine (C);
(c) N$^4$ is thymine (T);
(d) N$^5$ is thymine (T) or cytosine (C); and
(e) N$^6$ is guanine (G).

EMBODIMENT 9

The method of embodiment 8 wherein the fluorescent dye is carboxyfluorescein (FAM).

EMBODIMENT 10

A method for replicating and selectively collecting a nucleic acid containing an unnatural base pair from a nucleic acid pool, comprising:
(1) performing a nucleic acid replication reaction on a nucleic acid pool comprising a nucleic acid containing a nucleotide having a base represented by formula I below:

[Formula 9]

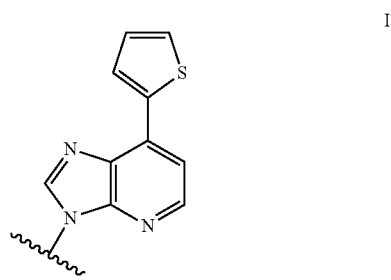

I (hereinafter referred to as Ds) using a substituted or unsubstituted deoxyribonucleoside 5'-triphosphate having a base represented by formula II below:

[Formula 10]

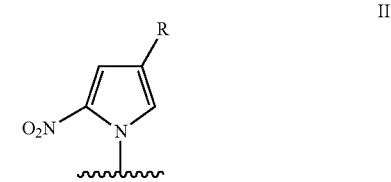

II wherein R is —X—Y,

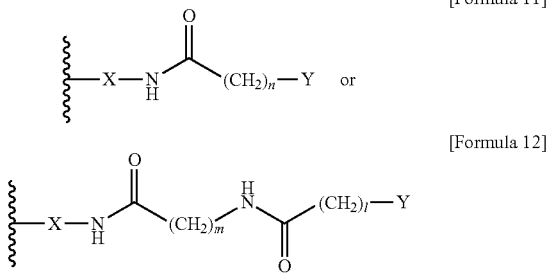

[Formula 11]

[Formula 12]

wherein
n is an integer selected from 1 to 12;
m is an integer selected from 1 to 12;
l is an integer selected from 1 to 12;
X is selected from a group consisting of —C≡C—CH$_2$—, —C≡C—, —C═C—, aryl, thienyl, imidazolyl, and thiazolyl;
Y is selected from a group consisting of an aryl substituted by Z, —NHCO—Z, —CONH—Z, —NHCONH—Z, —O—Z, —COO—Z, —O—C(═O)—Z, —CO—Z, and —S—Z, wherein Z is functional substituent selected from a group consisting of a fluorescent dye, biotin, an antibody-binding compound, a photocrosslinker, a chelating agent, an amino acid and a peptide; the base Ds, and/or a natural base, as a replication substrate; and (2) selectively collecting a nucleic acid containing an unnatural base pair of the base Ds and a base represented by formula II above from the resulting nucleic acids on the basis of the properties of the functional substituent borne by the base represented by formula II above.

EMBODIMENT 11

The method of embodiment 10 wherein the nucleic acid containing a nucleotide having the base Ds contains at least two nucleotides having the base Ds.

EMBODIMENT 12

The method of embodiment 10 or 11 wherein the replication substrate is not a deoxyribonucleoside 5'-triphosphate substituted at the hydroxyl group of the γ-phosphate.

EMBODIMENT 13

The method of any one of embodiment 10 to 12 wherein the nucleic acid containing a nucleotide having the base Ds includes a sequence of 5'-N$^1$N$^2$N$^3$(Ds)N$^4$N$^5$N$^6$-3' (SEQ ID NO: 1) as a flanking sequence of the base Ds, wherein N$^1$, N$^2$, N$^3$, N$^4$, N$^5$, N$^6$ are nucleotides having a natural base, provided that it satisfies at least two or more selected from the group consisting of the following criteria:
(a) N$^1$ is thymine (T) or cytosine (C);
(b) N$^3$ is cytosine (C);
(c) N$^4$ is thymine (T);
(d) N$^5$ is thymine (T) or cytosine (C); and
(e) N$^6$ is guanine (G).

EMBODIMENT 14

The method of embodiment 13 wherein the fluorescent dye is carboxyfluorescein (FAM).

EMBODIMENT 15

A method for determining the sequence of a natural base in the proximity of the unnatural base in DNA for achieving highly efficient and highly selective replication of a nucleic acid containing the unnatural base, comprising:

(1) preparing a DNA library including a random region represented by 5'-(N)$_n$(N$^{u1}$)(N)$_m$-3' (SEQ ID NO: 2), wherein n and m are each independently an integer selected from 1 to 10, and N$^{u1}$ is a first unnatural base;

(2) performing a nucleic acid replication reaction on the DNA library using a replication substrate containing a nucleoside having a second unnatural base N$^{u2}$ which forms an unnatural base pair with N$^{u1}$, wherein N$^{u2}$ contains a functional substituent;

(3) collecting a nucleic acid into which the functional substituent is introduced by the formation of an unnatural base pair of N$^{u1}$ and N$^{u2}$, on the basis of the properties of the functional substituent;

(4) repeating steps (2) and (3) on the nucleic acid collected in (3); and (5) determining the sequence of the resulting nucleic acid.

EMBODIMENT 16

A method for determining the sequence of a natural base in the proximity of the unnatural base in DNA for achieving highly efficient and highly selective replication of a nucleic acid containing the unnatural base, comprising:

(1) preparing a DNA library including a random region represented by 5'-(N)$_n$(Ds)(N)$_m$-3' (SEQ ID NO: 3) containing a nucleotide having a base represented by formula I below:

[Formula 13]

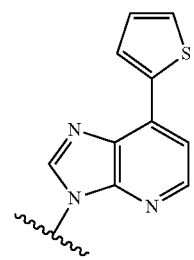

I wherein n and m are each independently an integer selected from 1 to 10;

(2) performing a nucleic acid replication reaction on the DNA library using a substituted or unsubstituted deoxyribonucleoside 5'-triphosphate having a base represented by formula II below:

[Formula 14]

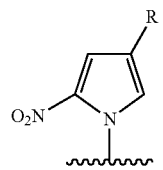

II wherein R is —X—Y,

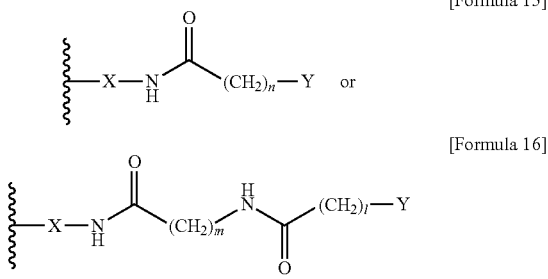

wherein
n is an integer selected from 1 to 12;
m is an integer selected from 1 to 12;
l is an integer selected from 1 to 12;
X is selected from a group consisting of —C≡C—CH$_2$—, —C≡C—, —C=C—, aryl, thienyl, imidazolyl, and thiazolyl;
Y is selected from a group consisting of an aryl substituted by Z, —NHCO—Z, —CONH—Z, —NHCONH—Z, —O—Z, —COO—Z, —O—C(=O)—Z, —CO—Z, and —S—Z, wherein Z is a functional substituent selected from a group consisting of a fluorescent dye, biotin, an antibody-binding compound, a photocrosslinker, a chelating agent, an amino acid and a peptide; the base Ds, and/or a natural base, as a replication substrate;

(3) collecting a nucleic acid into which the functional substituent is introduced by the formation of an unnatural base pair of the base Ds and a base represented by formula II above, on the basis of the properties of the functional substituent;

(4) repeating steps (2) and (3) on the nucleic acid collected in (3); and (5) determining the sequence of the resulting nucleic acid.

EMBODIMENT 17

The method of embodiment 16 wherein the replication substrate is not a deoxyribonucleoside 5'-triphosphate substituted at the hydroxyl group of the γ-phosphate.

EMBODIMENT 18

A nucleic acid obtained by the method of embodiment 16 or 17.

EMBODIMENT 19

A nucleic acid containing a nucleotide having a base represented by formula I below:

[Formula 17]

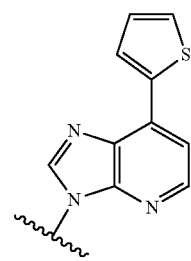

I (hereinafter referred to as Ds), which includes a sequence of 5'-N$^1$N$^2$N$^3$(Ds)N$^4$N$^5$N$^6$-3' (SEQ ID NO: 1) as a flanking sequence of the base Ds, wherein N$^1$, N$^2$, N$^3$, N$^4$, N$^5$, N$^6$ are nucleotides having a natural base, provided that it satisfies at least two or more selected from the group consisting of the following criteria:

(a) N$^1$ is thymine (T) or cytosine (C);
(b) N$^3$ is cytosine (C);
(c) N$^4$ is thymine (T);
(d) N$^5$ is thymine (T) or cytosine (C); and
(e) N$^6$ is guanine (G).

Advantages of the Invention

Unnatural base pairs of derivatives containing a substituent having a π-electron system attached at position 4 of the unnatural base Pn and the unnatural base Ds were developed. The use of these unnatural base pairs made it possible to use even unmodified nucleotide 5'-triphosphates as replication substrates for all bases (each of the bases Ds, Pn derivative, A, G, C, and T) in replication reactions of nucleic acids containing the unnatural bases. The conservation rates of the unnatural base pairs of the present invention in nucleic acid replication reactions are so high that they can be applied to various nucleic acid replication/amplification techniques. In addition, functional substituents can be added to the ends of the substituents having a π-electron system attached to Pn via linker moieties having various lengths, whereby the functional substituents can be regioselectively incorporated into DNA using the unnatural bases of the present invention and the DNA into which they have been incorporated per se can be replicated.

BRIEF EXPLANATION OF THE DRAWINGS

FIG. 5-1 depicts a schematic diagram of an experiment for incorporating FAM-hx-dPnTP into DNA by PCR amplification, and electrophoretograms showing the results.

FIG. 5-2 depicts a schematic diagram of an experiment for incorporating NH$_2$-hx-dPnTP into DNA by PCR amplification, and sequencing peak patterns showing the results of an analysis of the sequences of the amplified DNA products.

PREFERRED EMBODIMENTS OF THE INVENTION

Figure 1:
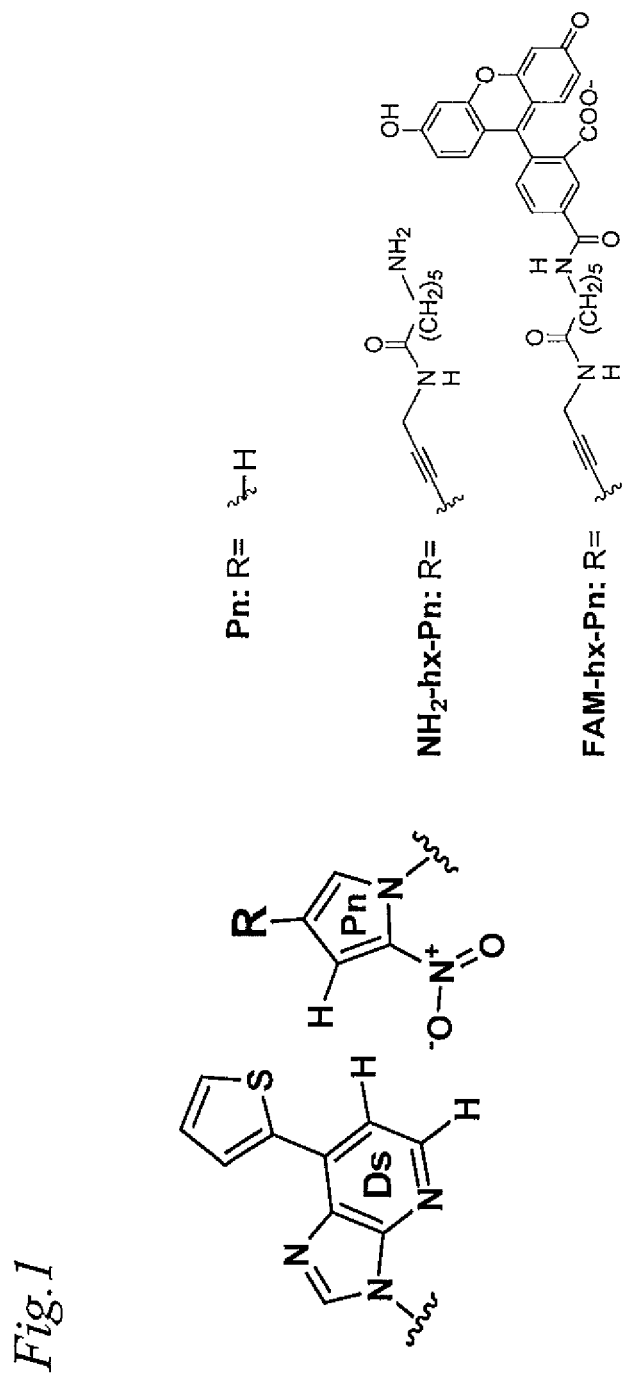
FIG. 1 depicts the structures of Ds, Pn, NH$_2$-hx-Pn, and FAM-hx-Pn.

The present invention will now be explained further in detail below.

Unnatural Base Pairs

Unnatural base pairs of the present invention are base pairs formed of the unnatural base Ds and a derivative of the unnatural base Pn.

The unnatural base Ds is represented by formula I below:

[Formula 18]

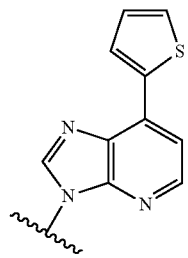

I

The derivative of the unnatural base Pn is represented by formula II below:

[Formula 19]

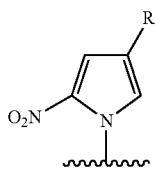

II wherein
R is —X—Y,

[Formula 20]

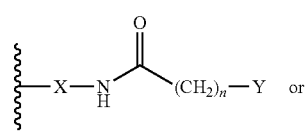

[Formula 21]

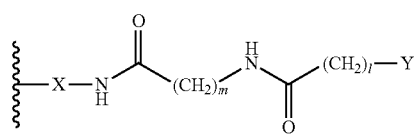

wherein
n is an integer selected from 1 to 12, preferably 1 to 10, more preferably 1 to 8, still more preferably 1 to 5;
m is an integer selected from 1 to 12, preferably 1 to 10, more preferably 1 to 8, still more preferably 1 to 5;
l is an integer selected from 1 to 12, preferably 1 to 10, more preferably 1 to 8, still more preferably 1 to 5;

X is selected from a group consisting of —C≡C—CH$_2$—, —C≡C—, —C═C—, aryl, thienyl, imidazolyl, and thiazolyl, preferably —C≡C—CH$_2$— or —C≡C—, more preferably —C≡C—CH$_2$—;

Y is selected from a group consisting of —CH$_3$, —C$_2$H$_5$, —NH$_2$, —OH, —COOH, —CHO, —SH, a substituted or unsubstituted aryl, —NHCO—Z, —CONH—Z, —NH-CONH—Z, —O—Z, —COO—Z, —O—C(═O)—Z, —CO—Z, and —S—Z, wherein Z is selected from a group consisting of a fluorescent dye, biotin, an antibody-binding compound, a photocrosslinker, a chelating agent, an amino acid and a peptide.

In the Pn derivative represented by formula II, a substituent having a π r electron system is selected as the substituent X to increase affinity for DNA polymerases and reverse transcriptases.

In the Pn derivative represented by formula II, the —NHCO—(CH$_2$)$_n$—, and —NHCO—(CH$_2$)$_m$—NHCO—(CH$_2$)$_l$— moieties in the substituent R are linker moieties.

In the Pn derivative represented by formula II, the substituent Y may be a functional substituent moiety. As used herein, the functional substituent means a substituent having some function, such as a functional group amenable to chemical modification, a reactive functional group capable of participating in a chemical reaction, a labeling substance allowing for detection, a functional group capable of capturing/isolating a molecule, etc.

Examples of cases in which the substituent Y contains a functional group amenable to chemical modification include cases in which the substituent Y is —NH$_2$, —OH, —COOH, —CHO, or —SH, and cases in which the substituent Y contains an amino acid as the substituent Z, etc.

Examples of cases in which the substituent Y contains a reactive functional group capable of participating in a chemical reaction include cases in which the substituent Y contains a chelating agent as the substituent Z, etc. Chelating agents can confer a novel function on nucleic acids having an unnatural base because they can participate in cleavage of nucleic acid or protein chains in their proximity.

Examples of cases in which the substituent Y contains a labeling substance allowing for detection or a functional group capable of capturing/isolating a molecule include cases in which the substituent Y contains a fluorescent dye, biotin, an antibody-binding compound, a photocrosslinker, a chelating agent, an amino acid or a peptide or the like as the substituent Z.

As used herein, fluorescent dye refers to any fluorescence-emitting molecule and is not specifically limited, but preferably is selected from a group consisting of 5-carboxyfluorescein (5-FAM), 6-carboxyfluorescein (6-FAM), 5-carboxytetramethylrhodamine (5-TAMRA), 6-carboxytetramethylrhodamine (6-TAMRA), 5-(dimethylamino)naphthalene-1-sulfonyl (DANSYL), 5-carboxy-2',4,4',5',7,7'-hexachlorofluorescein (5-HEX), 6-carboxy-2',4,4',5',7,7'-hexachlorofluorescein (6-HEX), 5-carboxy-2',4,7,7'-tetrachlorofluorescein (5-TET), 6-carboxy-2',4,7,7'-tetrachlorofluorescein (6-TET), 5-carboxy-X-rhodamine (5-ROX), 6-carboxy-X-rhodamine (6-ROX), and derivatives thereof. A more preferred fluorescent dye is FAM or TAMRA, and still more preferably is FAM. Fluoresceins and rhodamines are generally expressed in two forms, i.e., ring-opened form and Spiro form.

Nucleotides or nucleosides having a base of formula II containing a fluorescent dye can detect nucleic acids depending on the nature of the fluorescent dye. For example, FAM has a wavelength of absorption maximum at 493 nm, and a wavelength of fluorescence maximum at 522 nm. TAMRA has a wavelength of absorption maximum at 553 nm, and a wavelength of fluorescence maximum at 578 nm. DANSYL has a wavelength of absorption maximum at 335 nm, and a wavelength of fluorescence maximum at 518 nm. HEX has a wavelength of absorption maximum at 535 nm, and a wavelength of fluorescence maximum at 556 nm. TET has a wavelength of absorption maximum at 521 nm, and a wavelength of fluorescence maximum at 536 nm. 5-ROX has a wavelength of absorption maximum at 567 nm, and a wavelength of fluorescence maximum at 591 nm. 6-ROX has a wavelength of absorption maximum at 570 nm, and a wavelength of fluorescence maximum at 590 nm. These fluorescent dyes can also be used as means for capturing/isolating nucleic acids containing nucleotides to which the fluorescent dyes have been bound with the aid of antibodies to these fluorescent dyes; such antibodies also are known in the art.

Biotin, also known as coenzyme R, is one of B vitamins. Biotin is known specifically to bind avidin, which is a glycoprotein contained in egg white, to form a complex. Therefore, nucleotides and nucleosides having biotin as a substituent specifically bind avidin protein. Thus, nucleic acids containing biotin-conjugated nucleotides can be used to capture/isolate such nucleic acids because they can be bound to avidin-immobilized carrier.

The antibody-binding compound refers to any substance binding to an antibody and is not specifically limited. Examples of antibody-binding compounds include digoxigenin, ascorbic acid, benzopyrene, etc.

The photocrosslinker refers to any substance inducing a crosslinking reaction upon photoirradiation and is not specifically limited. Examples of photocrosslinkers include benzophenones, azides, (trifluoromethyl)diazirinyl, etc.

The amino acid may be one of the twenty natural α-amino acids or an unnatural amino acid.

The peptide refers to a substance formed of two or more amino acids joined through an amide linkage. The number of amino acids forming the peptide is not limited specifically, but preferably may be 2-15, more preferably 2-10, and still more preferably 2-8.

The chelating agent is not specifically limited so far as it coordinates with a metal ion, radioisotope or the like as a ligand. Examples of chelating agents include nitrilotriacetic acid (NTA), trans-1,2-cyclohexadiamine-N,N,N',N'-tetraacetic acid (CyDTA), ethylenediamine tetraacetic acid (EDTA), etc.

In an especially preferred embodiment, the unnatural base Pn derivative of the present invention is NH$_2$-hx-Pn: 4-[3-(6-aminohexanamide)-1-propynyl]-2-nitropyrrole-1-yl group; or FAM-hx-Pn: 4-[3-[6-(fluorescein-5-carboxamide)hexanamide]-1-propynyl]-2-nitropyrrole-1-yl group.

Replication of a Nucleic Acid Containing an Unnatural Base Pair

In one embodiment, the present invention provides a method for replicating a nucleic acid containing an unnatural base pair, comprising performing a nucleic acid replication reaction on a template strand consisting of a nucleic acid containing a nucleotide having Ds and/or a Pn derivative as a base using a substituted or unsubstituted deoxyribonucleoside 5'-triphosphate having the base Ds, the base Pn derivative, and/or a natural base as a replication substrate, thereby replicating a nucleic acid containing an unnatural base pair of the base Ds and a base represented by formula II above.

As used herein, the "nucleoside" refers to a glycoside compound consisting of a nucleobase bound to a reducing group on a sugar via a glycosidic linkage. The "nucleobase" here includes natural bases, i.e., adenine (A), guanine (G), cytosine (C), thymine (T), and uracil (U), and derivatives thereof as well as unnatural bases. As used herein, "nucleotide" refers to a compound consisting of a sugar moiety of the nucleoside combined with a phosphate group to form an ester, more preferably, a mono-, di-, or triphosphate ester.

In the method of the present invention, the template strand is a nucleic acid containing a nucleotide having Ds and/or a Pn derivative as a base. The nucleic acid of the template strand may be DNA or RNA. The template strand may have only one Ds moiety or Pn derivative, or may have at least two such moieties or derivatives. Further, the template strand may have Ds and a Pn derivative in the same template strand. The maximum number of Ds moieties and/or Pn derivatives that the template strand may have is not specifically limited, but may be, for example, 20, 15, 10, or 5.

The replication substrate used in the method of the present invention is a substituted or unsubstituted deoxyribonucleoside 5'-triphosphate having Ds, a Pn derivative, and/or a natural base. Because of the high conservation rate of base pair formation of Ds-Pn derivative, in the nucleic acid replication method of the present invention it is possible to use unsubstituted deoxyribonucleoside 5'-triphosphates as replication substrates. Substituted deoxyribonucleoside 5'-triphosphates may also be used. Examples of substituted deoxyribonucleoside 5'-triphosphates include derivatives having a group selected from a group consisting of amino, methylamino, dimethylamino, mercapto and fluoro substituted for the hydroxyl group of the γ-phosphate; derivatives having a fluorescent dye attached to the γ-phosphate; derivatives containing a triphosphate as the α-phosphate, etc. Preferably, substituted deoxyribonucleoside 5'-triphosphates exclude derivatives having an amino group substituted for the hydroxyl group of the γ-phosphate, i.e., γ-amidotriphosphate derivatives.

In the method of the present invention, the nucleic acid replication reaction refers to a reaction in which a complementary strand to a template strand nucleic acid is enzymatically produced. The nucleic acid replication reaction includes a reaction using a DNA polymerase or reverse transcriptase. If a DNA polymerase is used, it preferably should have, but need not necessarily, an exonuclease activity for prevention of undesirable non-specific base pair formation during the nucleic acid replication. The DNA polymerase having exonuclease activity is selected from the group consisting of Klenow fragment, T4 DNA polymerase, Vent DNA polymerase, and Deep Vent DNA polymerase having 3'→5' exonuclease activity. Preferred examples of reverse transcriptases include, but are not limited to, AMV Reverse Transcriptase XL (AMV-RT) (Life Science), M-MLV Reverse Transcriptase (Promega), HIV Reverse Transcriptase (Applied Biosystems).

The replication reaction in the method of the present invention can be performed according to a known procedure.

The nucleic acid replication method of the present invention shows a high conservation rate of base pair formation of Ds-Pn derivative. Even template strands existing at a level of $10^{-20}$ mol can be amplified and detected while conserving base pair formation of Ds-Pn derivative by the nucleic acid replication method of the present invention.

In another embodiment, the present invention provides a method for incorporating an unnatural base bearing a functional substituent attached thereto into DNA through the use of the nucleic acid replication method of the present invention. That is, the present invention provides a method for incorporating an unnatural base bearing a functional substituent attached thereto into DNA by a nucleic acid replication reaction, comprising performing a nucleic acid replication reaction on a template strand which is a nucleic acid containing a nucleotide having Ds as a base using a substituted or unsubstituted deoxyribonucleoside 5'-triphosphate having the base Ds, the base Pn derivative, and/or a natural base as a replication substrate, thereby generating a nucleic acid containing an unnatural base pair of the base Ds and the base Pn derivative, whereby an unnatural base bearing a functional substituent attached thereto is incorporated into a DNA.

In the structure above, the unnatural base Pn derivative of the present invention has a functional substituent shown as substituent Y. An unnatural base bearing a functional substituent attached thereto can be regioselectively incorporated into DNA by generating a nucleic acid containing an unnatural base pair of Ds-Pn derivative by carrying out the nucleic acid replication method of the present invention on a template strand consisting of a nucleic acid containing a nucleotide having Ds as a base.

Selective Detection/Collection of a Nucleic Acid Containing an Unnatural Base Pair The unnatural base Pn derivative of the present invention may have a functional substituent selected from the group consisting of a fluorescent dye, biotin, an antibody-binding compound, a photocrosslinker, a chelating agent, an amino acid and a peptide. When the Pn derivative has these functional substituents, a nucleic acid containing an unnatural base pair of Ds-Pn derivative generated by the nucleic acid replication method of the present invention can be selectively detected and/or collected on the basis of the properties of these functional substituents. In the present invention, examples of unnatural bases bearing a functional substituent that allows for detection and/or collection of a nucleic acid containing an unnatural base pair include Pn derivatives represented by formula II having a fluorescent dye, biotin, an antibody-binding compound, a photocrosslinker, a chelating agent, an amino acid or a peptide or the like as substituent Z.

When the derivative has a fluorescent dye as a functional substituent, detection of a nucleic acid can be performed depending on the nature of the fluorescent dye. Further, a nucleic acid containing an unnatural base pair of Ds-Pn derivative generated by the nucleic acid replication method of the present invention can be collected by selectively capturing and isolating it with the aid of an antibody binding to the fluorescent dye.

When the derivative has biotin as a functional substituent, a nucleic acid containing an unnatural base pair of Ds-Pn derivative generated by the nucleic acid replication method of the present invention can be collected by selectively capturing and isolating it through use of specific binding of biotin-avidin. Further, a nucleic acid having biotin as a functional substituent can be detected by using avidin or streptavidin conjugated to a chemiluminescent substance or fluorescent dye.

When the derivative has an antibody-binding compound as a functional substituent, a nucleic acid containing an unnatural base pair of Ds-Pn derivative generated by the nucleic acid replication method of the present invention can be collected by selectively capturing and isolating it through the use of binding to an antibody. Further, a nucleic acid having an antibody-binding compound as a functional substituent can be detected by such a method as ELISA through the use of binding to an antibody.

When the derivative has a photocrosslinker as a functional substituent, a nucleic acid containing an unnatural base pair of Ds-Pn derivative generated by the nucleic acid replication method of the present invention can be collected by selectively capturing and isolating it by crosslinking it to a carrier or the like by photoirradiation.

When the derivative has an amino acid as a functional substituent, a nucleic acid containing an unnatural base pair which is obtained by the method of the present invention can be collected by being captured selectively and isolated by binding to an antibody that binds to the amino acid. Further, a nucleic acid having an amino acid as a functional substituent can be detected by such a method as ELISA through use of binding to an antibody.

When the derivative includes a chelating agent as a functional substituent, a nucleic acid containing an unnatural base pair can be collected by being selectively captured and isolated with the aid of a suitable ligand. Further, a nucleic acid containing an unnatural base pair can be detected with the aid of a suitable ligand.

When the derivative contains a peptide as a functional substituent, a nucleic acid containing an unnatural base pair of Ds-Pn derivative generated by the nucleic acid replication method of the present invention can be collected by being selectively captured and isolated with the aid of a substance binding to the amino acid. The substance binding to the peptide is not limited specifically, and may be an antibody. In a case that the substance binding to the peptide is an antibody, a nucleic acid having an unnatural base pair can be detected by a method such as ELISA. Specific examples of combinations of a peptide and a substance binding thereto include the following combinations. When the peptide is a histidine tag ((His)$_6$ (SEQ ID NO: 57)), the substance binding to the peptide may be Ni-NTA. When the peptide is glutathione (L-γ-glutamyl-L-cysteinyl-glysine), the substance binding to the peptide may be glutathione-S-transferase. When the peptide is a FLAG tag (DYKDDDDK (SEQ ID NO: 58)) or a MYC tag (EQKLISEEDL (SEQ ID NO: 59)), the substance binding to the peptide is an antibody binding to the tag.

Thus, a nucleic acid containing an unnatural base pair of Ds-Pn derivative generated by the nucleic acid replication method of the present invention can be selectively detected and/or collected with the aid of a Pn derivative bearing a functional substituent as described above.

In another embodiment, therefore, the present invention provide a method for replicating and selectively collecting a nucleic acid containing an unnatural base pair from a nucleic acid pool, comprising performing a nucleic acid replication reaction on a nucleic acid pool including a nucleic acid containing an nucleotide having the unnatural base Ds by the nucleic acid replication method of the present invention; and selectively collecting a nucleic acid containing an unnatural base pair of the unnatural base Ds and an unnatural base Pn derivative from the resulting nucleic acids on the basis of the properties of the functional substituent borne by the Pn derivative.

In still another embodiment, the present invention provides a method for replicating and selectively detecting a nucleic acid containing an unnatural base pair from a nucleic acid pool, comprising performing a nucleic acid replication reaction on a nucleic acid pool including a nucleic acid containing a nucleotide having the unnatural base Ds by the nucleic acid replication method of the present invention; and selectively detecting a nucleic acid containing an unnatural base pair of the unnatural base Ds and an unnatural base Pn derivative from the resulting nucleic acids on the basis of the properties of the functional substituent borne by the Pn derivative.

In the methods of the present invention, the nucleic acid pool refers to a collection of multiple types of nucleic acids. The sequences and lengths of nucleic acids included in the nucleic acid pool are not limited, but may be various sequences and various lengths. The nucleic acid pool includes at least one nucleic acid containing a nucleotide having the unnatural base Ds.

The methods of the present invention can be applied to authentification techniques using a nucleic acid containing an unnatural base, because a nucleic acid containing an unnatural base pair can be replicated and selectively detected and/or collected from a nucleic acid pool consisting of a collection of nucleic acids of various sequences and various lengths. For example, they can be applied to authentification techniques by incorporating a nucleic acid containing an unnatural base into a tag of an article along with large amounts of foreign DNAs as proof of authenticity of the article, amplifying the nucleic acid containing the unnatural base to a detectable level, and detecting and/or collecting the amplified nucleic acid containing the unnatural base to confirm the sequence.

Sequences of Natural Bases in the Proximity of the Unnatural Base Allowing for Highly Efficient and Highly Selective Nucleic Acid Replication of a Nucleic Acid Containing the Unnatural Base The present inventors hypothesized that efficiency and selectivity of formation of an unnatural base pair of a template base and a replication substrate ring in replication is dependent partially upon the sequence of natural bases in the proximity of the unnatural base pair in DNA. Then, we searched for sequences of an unnatural base pair and its flanking natural bases showing efficient nucleic acid amplification in a nucleic acid replication reaction by using an in vitro selection method, as described in Example 2 below. As a result, we found sequences of an unnatural base pair and its flanking natural bases showing efficient nucleic acid amplification in a nucleic acid replication reaction.

Therefore, the present invention also provides the methods of the present invention, further characterized by using a template strand including a sequence of 5'- $N^1N^2N^3$(Ds)$N^4N^5N^6$-3' (SEQ ID NO: 1) as a flanking sequence of the unnatural base Ds in the template strand, wherein $N^1$, $N^2$, $N^3$, $N^4$, $N^5$, $N^6$ are nucleotides having a natural base, provided that it satisfies at least two or more criteria of the group consisting of the following:
(a) $N^1$ is thymine (T) or cytosine (C);
(b) $N^3$ is cytosine (C);
(c) $N^4$ is thymine (T);
(d) $N^5$ is thymine (T) or cytosine (C); and
(e) $N^6$ is guanine (G).
Preferably, a template strand satisfying at least three or more, more preferably four or more, still more preferably all five of the criteria (a)-(e) above may be used. Alternatively, a template strand satisfying at least two or more criteria of the group consisting of (b), (c) and (e) above may be used.

Alternatively, the present invention also provides the methods of the present invention, characterized by using a template strand including a sequence of 5'-$N^{1'}N^{2'}N^{3'}$(Pn derivative)$N^{4'}N^{5'}N^{6'}$-3' (SEQ ID NO: 4) as a flanking sequence of the unnatural base Ds in the template strand, wherein $N^{1'}$, $N^{2'}$, $N^{3'}$, $N^{4'}$, $N^{5'}$, $N^{6'}$ are nucleotides having a natural base, provided that the nucleic acid satisfies at least two or more criteria of the group consisting of the following:
(a) $N^{1'}$ is cytosine (C);
(b) $N^{2'}$ is adenine (A) or guanine (G);
(c) $N^{3'}$ is adenine (A);
(d) $N^{4'}$ is guanine (G); and
(e) $N^{6'}$ is adenine (A) or guanine (G).
Preferably, a template strand satisfying at least three or more, more preferably four or more, still more preferably all five of the criteria (a)-(e) above may be used. Alternatively, a template strand satisfying at least two or more criteria of the group consisting of (a), (c) and (d) above may be used.

The present invention also provides a nucleic acid containing a nucleotide having the unnatural base Ds, said nucleic acid including a sequence of 5'-$N^1N^2N^3$(Ds)$N^4N^5N^6$-3' (SEQ ID NO: 1) as a flanking sequence of the unnatural base Ds, wherein $N^1$, $N^2$, $N^3$, $N^4$, $N^5$, $N^6$ are nucleotides having a natural base, provided that the nucleotides satisfies at least two or more criteria of the group consisting of the following:
(a) $N^1$ is thymine (T) or cytosine (C);
(b) $N^3$ is cytosine (C);
(c) $N^4$ is thymine (T);
(d) $N^5$ is thymine (T) or cytosine (C); and
(e) $N^6$ is guanine (G).
Preferably, the nucleic acid may satisfy at least three or more, and more preferably four or more, and still more preferably all five of the criteria (a)-(e) above. Alternatively, the nucleic acid may satisfy at least two or more criteria of the group consisting of (b), (c) and (e) above.

Alternatively, the present invention provides a nucleic acid containing a nucleotide having an unnatural base Pn derivative that is a complementary strand of a nucleic acid containing a nucleotide having the unnatural base Ds, said nucleic acid including a sequence of 5'-$N^{1'}N^{2'}N^{3'}$(Pn derivative)$N^{4'}N^{5'}N^{6'}$-3' (SEQ ID NO: 4) as a flanking sequence of the unnatural base Pn derivative, wherein $N^{1'}$, $N^{2'}$, $N^{3'}$, $N^{4'}$, $N^{5'}$, $N^{6'}$ are nucleotides having a natural base, provided that it satisfies at least two or more criteria of the group consisting of the following:
(a) $N^{1'}$ is cytosine (C);
(b) $N^{2'}$ is adenine (A) or guanine (G);
(c) $N^{3'}$ is adenine (A);
(d) $N^{4'}$ is guanine (G); and
(e) $N^{6'}$ is adenine (A) or guanine (G).
Preferably, the nucleic acid may satisfy at least three or more, more preferably four or more, and still more preferably all five of the criteria (a)-(e) above. Alternatively, the nucleic acid may satisfy at least two or more criteria of the group consisting of (a), (c) and (d).

Sequencing of Nucleic Acids Containing an Unnatural Base

Sequencing of DNA fragments containing the unnatural base Ds can be performed by using a Ds-Pa base pair.

Hirao et al., (Nature Methods, 3: 729-735 (2006)) reported a method based on a difference in sequencing pattern depending on the presence or absence of a substrate of a propynyl derivative of Pa, which is a complementary base of Ds (dPa'TP: 1-(2-deoxy-β-D-ribofuranosyl)-4-(1-propynyl)pyrrole-2-carbaldehyde 5'-triphosphate). This method gives a peak pattern indicating the termination of the sequencing reaction at the site of a base complementary to Ds in the template DNA when sequencing is performed by a dideoxy dye terminator method of Ds-containing DNA without adding dPa'TP, for example. When sequencing is performed with dPa'TP, however, the reaction proceeds but gives a peak pattern in which a sequencing peak disappeared only at the site of a base complementary to Ds in the template DNA due to the absence of a dideoxy dye terminator of fluorescently labeled Pa'. A DNA sequence containing the unnatural base is determined by comparing these two sequencing patterns. However, this previous method had the disadvantage that substrates for some natural bases in the proximity of Ds in the template strand DNA might be misincorporated into the Ds site depending on the sequence of the natural bases even if dPa'TP were not added, in which case the sequencing reaction proceeded and a clear sequencing peak pattern would not be obtained.

Figure 4:
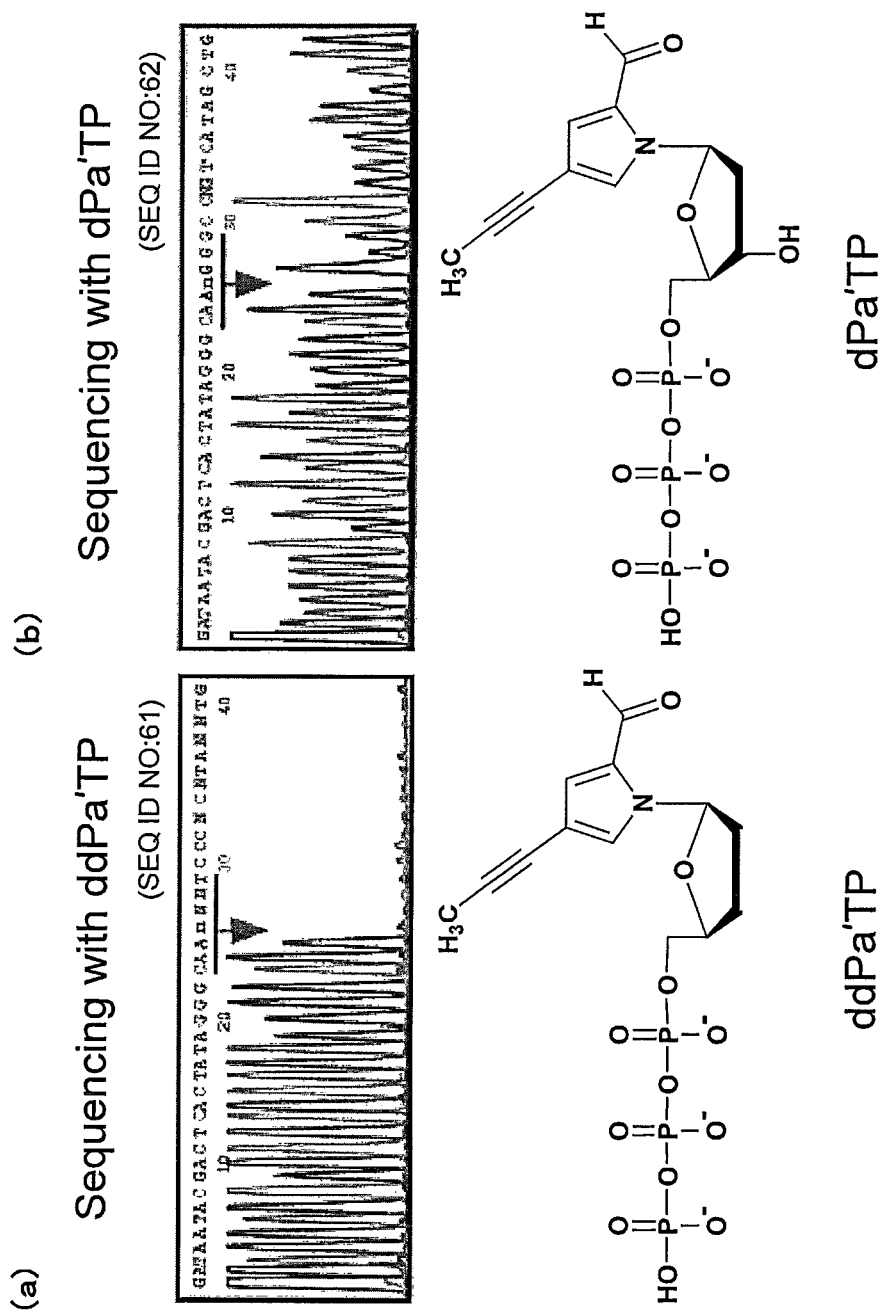
FIG. 4 depicts sequencing peak patterns of sequencing reactions using ddPa'TP and dPa'TP.

Thus, the present invention provides a method for sequencing a DNA fragment containing the unnatural base Ds by using a substrate of a propynyl-modified dideoxy derivative of Pa (ddPa'TP: 1-(2,3-dideoxy-β-D-ribofuranosyl)-4-(1-propynyl)pyrrole-2-carbaldehyde 5'-triphosphate) to completely terminate the sequencing reaction at the Ds site in the template strand DNA. When sequencing of a DNA fragment containing Ds is performed by a dideoxy dye terminator method with ddPa'TP, ddPa'TP is incorporated reliably into the Ds site, to thereby prevent misincorporation of substrates for natural bases. This gives a peak pattern in which sequencing peaks after Ds disappear (FIG. 4a). When the dideoxy dye terminator method is used with dPa'TP, the sequencing peak disappears only at the site corresponding to Ds (FIG. 4b). By comparing these two sequencing patterns, sequencing information on DNA fragments containing Ds can be obtained without relying on DNA nucleotide sequences in the proximity of Ds.

Method for Determining the Sequence of Natural Bases in the Proximity of an Unnatural Base in DNA for Achieving Highly Efficient and Highly Selective Replication of a Nucleic Acid Containing the Unnatural Base In one embodiment, the present invention provides a method for determining the sequence of natural bases in the proximity of an unnatural base in DNA for achieving highly efficient and highly selective replication of a nucleic acid containing the unnatural base. Accordingly, the present invention provides a method for determining the sequence of natural bases in the proximity of an unnatural base in DNA for achieving highly efficient and highly selective replication of a nucleic acid containing the unnatural base, comprising:

(1) preparing a DNA library including a random region represented by 5'-(N)$_n$(N$^{u1}$)(N)$_m$-3' (SEQ ID NO: 2), wherein n and m are each independently an integer selected from 1 to 10, and N$^{u1}$ is a first unnatural base;

(2) performing a nucleic acid replication reaction on the DNA library using a replication substrate containing a nucleoside having a second unnatural base N$^{u2}$ which forms an unnatural base pair with N$^{u1}$, wherein N$^{u2}$ contains a functional substituent;

(3) collecting a nucleic acid into which the functional substituent is introduced by the formation of an unnatural base pair of N$^{u1}$ and N$^{u2}$, on the basis of the properties of the functional substituent;

(4) repeating steps (2) and (3) on the nucleic acid collected in (3); and (5) determining the sequence of the resulting nucleic acid.

In the method of the present invention, the combination of N$^{u1}$ and N$^{u2}$ in the unnatural base pair may be any combination of an unnatural base pair and not specifically limited, but preferably includes combinations of:

isoG-isoC (patent document 3, and non-patent document 9);
P—Z (P: 2-amino-imidazo[1,2-a]-1,3,5-triazine-4(8H)-one, Z: 6-amino-5-nitro-2(1H)-pyridone) (non-patent document 22);
s-y (s: 2-amino-6-(2-thienyl)purine, y: 2-oxopyridine) (non-patent documents 16-17);
v-y (v: 2-amino-6-(2-thiazolyl)purine, y: 2-oxopyridine) (non-patent document 18);
Ds-Pa;
Ds-Pn; and
Ds-Pn derivative.

Those skilled in the art will readily understand that when the former in the combinations above is N$^{u1}$, the latter is N$^{u2}$, and when the latter is N$^{u1}$, the former is N$^{u2}$.

In a preferred embodiment, N$^{u1}$ is Ds, and N$^{u2}$ is a Pn derivative represented by formula II herein in the method of the present invention.

In the method of the present invention, the step of determining the sequence of the resulting nucleic acid can be performed by using any method capable of determining the sequence of a nucleic acid containing an unnatural base. When the combination of N$^{u1}$ and N$^{u2}$ in the unnatural base pair is a combination of Ds-Pa, Ds-Pn, or Ds-Pn derivative, the sequence of the resulting nucleic acid may be determined preferably using the method using ddPa'TP described above.

The present invention also provides a nucleic acid obtained by the method of the present invention for determining the sequence of natural bases in the proximity of an unnatural base in DNA for achieving highly efficient and highly selective replication of a nucleic acid containing the unnatural base.

EXAMPLES

The following examples further illustrate the present invention but are not intended to limit the technical scope of the present invention. Those skilled in the art can readily add modifications/changes to the present invention in the light of the description herein, and such modifications/changes are included in the technical scope of the present invention.

In the Examples below, the functional groups/compounds represented by the symbols below have the following meanings.

Ds: 7-(2-thienyl)-3H-imidazo[4,5-b]pyridine-3-yl group;
Pn: 2-nitro-1H-pyrrole-1-yl group;
Pa: 2-formyl-1H-pyrrole-1-yl group;
NH$_2$-hx-Pn: 4-[3-(6-aminohexanamide)-1-propynyl]-2-nitropyrrole-1-yl group;
FAM-hx-Pn: 4-[3-[6-(fluorescein-5-carboxamide)hexanamide]-1-propynyl]-2-nitropyrrole-1-yl group;
NH$_2$-hx-dPnTP: 1-(2-deoxy-β-D-ribofuranosyl)-4-[3-(6-amino-hexanamide)-1-propynyl]-2-nitropyrrole 5'-triphosphate;
FAM-hx-dPnTP: 1-(2-deoxy-β-D-ribofuranosyl)-4-[3-[6-(fluorescein-5-carboxamide) hexanamide]-1-propynyl]-2-nitropyrrole 5'-triphosphate
dPa'TP: 1-(2-deoxy-β-D-ribofuranosyl)-4-(1-propynyl)pyrrole-2-carbaldehyde 5'-triphosphate;
ddPa'TP: 1-(2,3-dideoxy-β-D-ribofuranosyl)-4-(1-propynyl) pyrrole-2-carbaldehyde 5'-triphosphate.

The structures of Ds, Pn, NH$_2$-hx-Pn, and FAM-hx-Pn are shown in FIG. 1.

Example 1

Analysis of the Reaction Rate Constant of a Single Nucleotide Insertion Reaction by Klenow Fragment To assess the efficiency and selectivity of base pair formation between a 1-propynyl derivative of the unnatural base Pn and Ds in replication, a nucleotide insertion experiment with Klenow fragment of DNA polymerase I derived from E. coli was performed and the reaction rate constant was analyzed.

A single nucleotide insertion experiment was performed as described in the literature (Kimoto, M., et al., Biotechnol. Lett., 2004, 26: 999-1005; Petruska, J., et al., Proc. Natl. Acad. Sci. USA, 1988, 85: 6252-6256; Goodman, M. F., et al., J. Crit. Rev. Biochem. Mol. Biol., 1993, 28: 83-126; Morales, J. C., et al., Nat. Struct. Biol., 1998, 5: 950-954). Specifically, primers labeled with 6-carboxyfluorescein at the 5' end (20-mer, 5'-ACTCACTATAGGGAGGAAGA-3'(SEQ ID NO: 5) or, 5'-ACTCACTATAGGGAGCTTCT-3'(SEQ ID NO: 6)) and a template DNA (35-mer, 5'-AGCTCTNTCT-TCCTCCCTATAGTGAGTCGTATTAT-3' (SEQ ID NO: 7) (N=Ds, A, C, or, T) or, 5'-TCGAGANAGAAGCTCCCTAT-AGTGAGTCGTATTAT-3' (SEQ ID NO: 8) (N=Pa, or Pn)) were heated at 95° C. in a 100 mM Tris-HCl (pH 7.5) buffer containing 20 mM MgCl$_2$, 2 mM DTT, and 100 µg/ml bovine serum albumin (BSA), then annealed by slowly cooling to 4° C. to form a double strand of a template strand and a primer strand. A 5 µl aliquot of this primer/template double-stranded DNA solution (10 µM or 2 µM) was incubated with an enzyme solution (2 µl) of Kienow fragment lacking exonuclease activity (KF exo⁻, Amersham USB) at 37° C. for 2 minutes to form a DNA/enzyme complex. To this solution was added 3 µl of each substrate, i.e., a nucleoside triphosphate or γ-amidotriphosphate solution (where the base is one of NH$_2$-hx-Pn, Pn, Pa, Ds, A, G, C, or T) (1 µM-5 mM) to perform an enzymatic reaction at 37° C. (for 1-28.2 minutes). The reaction was quenched by adding 10 µl of a 95% formamide solution containing 20 mM EDTA (quenching solution) and heating at 75° C. for 3 minutes.

The reaction solution (10 µl) contained 1 µM or 5 µM primer/template double strand, 2-50 nM enzyme, and 0.3-1500 µM substrate. The reaction solution (10 µl) also contained 50 mM Tris-HCl (pH 7.5), 10 mM MgCl$_2$, 1 mM DTT and 0.05 mg/ml BSA.

After the quenching solution was added to the reaction solution, the resulting solution (0.5 µl) was mixed with a loading solution (deionized formamide: Blue Dextran solution containing 25 mM EDTA (50 mg/ml)=5:1; 3 µl), and the mixed solution was heated at 90° C. for 2 minutes, and quenched on ice. A 0.5 µl aliquot was loaded on a sequencing gel and subjected to electrophoresis. The sequence gel (36 cm WTR) contained 6M urea, 8-10% polyacrylamide (acrylamide:bisacrylamide=19:1), 0.5×TBE. The electrophoresis buffer used was 0.5×TBE. Run Module is GS Run 36C-2400. The migration time was about 1 hour, and the peak pattern of the reaction product was analyzed and quantified by an automatic ABI377 DNA sequencer equipped with GeneScan software (version 3.0).

The proportion of the primers extended by one nucleotide was determined from the peak areas of unreacted primer fragments and DNA fragments into which one nucleotide had been inserted, and kinetic parameters (Vmax and Km) were calculated by a Hanes-Woolf plots (Goodman, M. F., et al., J. Crit. Rev. Biochem. Mol. Biol., 1993, 28: 83-126). Note that the Vmax value was determined by normalizing the enzyme concentration to 20 nM and the concentration of double-stranded DNA to 5 µM.

Figure 2:
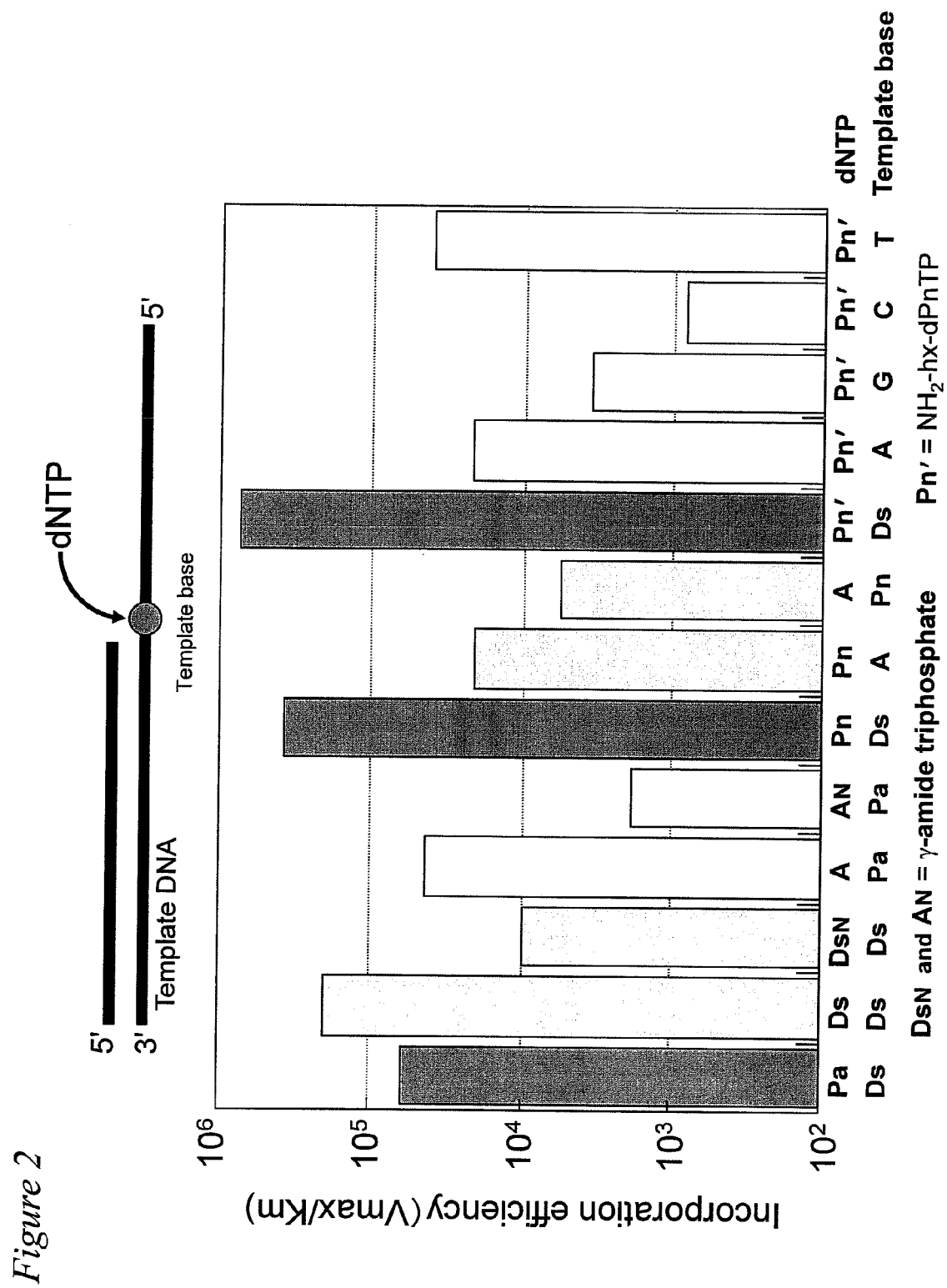
FIG. 2 depicts a schematic diagram of a single nucleotide insertion experiment using Klenow fragment, and a graph showing the results.

The results are shown in FIG. 2. The incorporation efficiency of the Pa substrate into Ds in the template strand was Vmax/Km=6.2×10$^4$, and the incorporation efficiency of the Pn substrate into Ds in the template strand was 3.7×10$^5$. In contrast, the incorporation efficiency of the Pn derivative substrate having a propynyl group (NH$_2$-hx-dPnTP) into Ds in the template strand was 7.4×10$^5$, which was about twice the incorporation efficiency of the Pn substrate into Ds in the template strand. The incorporation efficiency of the Pn derivative substrate having a prop ynyl group into Ds in the template strand was also higher than the incorporation efficiency of the Ds substrate into Ds in the template strand, which was 2.0×10$^5$. Further, the incorporation efficiency of the Pn derivative substrate having a propynyl group into natural bases was found to be lower than the incorporation efficiency into Ds. Therefore, an unnatural base pair of Ds and the Pn derivative was formed more efficiently than undesirable base pairs of Ds-Ds and A-Pn in replication.

The results of the above experiment demonstrated that the Pn derivative substrate having a propynyl group, which is a substituent having a π-electron system, is selectively incorporated into Ds in the template strand DNA more efficiently than the substrate of the unnatural base Pn. In contrast to the previous Ds-Pn base pair that used a γ-amidotriphosphate derivative of Ds to prevent incorporation of substrate Ds into template Ds, the incorporation efficiency of the Pn derivative substrates into template Ds became higher than the incorporation efficiency of substrate Ds into template Ds. This eliminated the need of using a γ-amidotriphosphate derivative in the replication of a base pair of Ds-Pn derivative, which made it possible to develop a simple system for replicating DNAs containing an unnatural base pair.

Example 2

Sequencing of Natural Bases in the Proximity of an Unnatural Base in DNA for Achieving Highly Efficient and Highly Selective PCR Amplification of DNA Containing the Unnatural Base On the hypothesis that the efficiency and selectivity of formation of an unnatural base pair of a template base and a substrate partially depend on the sequence of natural bases in the proximity of the unnatural base pair in DNA, the present inventors searched for sequences of an unnatural base pair and its flanking natural bases showing an efficient amplification by PCR by using an in vitro evolution engineering method (in vitro selection method).

(2-1: In Vitro Selection)

Specifically, in vitro selection was performed to determine the sequence of natural bases in the proximity of the unnatural base that can be amplified by PCR with high efficiency and high selectivity according to the following procedure using an evolution engineering method with a DNA library of random sequences. Initially, a DNA fragment containing Ds was prepared by chemically synthesizing a single-stranded DNA containing three randomized natural bases flanking the unnatural base Ds on each side (55-mer; 5'-TTTCACACAG-GAAACAGCTATGACGG-NNN-Ds-NNN-CCCTATAGT-GAGTCGTATTATC-3'(SEQ ID NO: 9)) by a DNA synthesizer and purifying it by gel electrophoresis. This DNA fragment (2 pmol) was used as a template to perform PCR with substrates for natural bases (dNTPs, N=A, G, C, T) and substrates for unnatural bases (dDsTP, FAM-hx-dPnTP), and Deep Vent DNA polymerase (0.04 units/µl). The PCR reaction scale was 200 µl, and the reaction buffer contained 20 mM Tris-HCl (pH 8.8), 10 mM KCl, 10 mM (NH$_4$)$_2$SO$_4$, 2 mM MmgSO$_4$, 0.1% Triton X-100. A 5'-primer (5'-GATAATACGACTCACTATAG-3'(SEQ ID NO: 10)) and a 3'-primer (5'-TTTCACACAGGAAACAGCTATGAC-3' (SEQ ID NO: 11)) were used each at a concentration of 1 µM, in combination with a substrate dNTP for each natural base (0.3 mM) and FAM-hx-dPnTP (2.5 µM) and dDsTP (50 µM) as substrates for the unnatural base. PCR conditions included 94° C. for 30 seconds, 45° C. for 30 seconds, and 65° C. for 4 minutes per cycle. After 10 cycles of PCR amplification, the full-length PCR product was purified by electrophoresis on 10% PAGE-7M urea gel, and the concentration of collected DNA was calculated from the absorbance at 260 nm.

The amplified DNA fragment (which corresponds to about 20 pmol as single-stranded DNA) and 20 µl of an anti-FAM antibody (1 mg/ml, purchased from Invitrogen) were mixed in phosphate buffer (PBS, final volume 100 µl) on ice and left for 1 hour. This solution was subjected to ultrafiltration using Microcon YM-100 from Millipore to isolate the amplified DNA fragment containing FAM-hx-Pn bound to the anti-FAM antibody. This solution was treated with phenol/chloroform and DNA was collected by ethanol precipitation of the aqueous layer. About 1 pmol of the total amount of thus obtained DNA was used as a template for PCR (200 µl scale, the same reaction conditions as described above) in the subsequent round of selection.

A total of 5 rounds of selection were performed, each consisting of PCR amplification and the subsequent isolation of a fragment containing FAM-hx-Pn. The DNA fragment obtained after 5 rounds was used to perform PCR, and the nucleotide sequence of the resulting DNA fragment was analyzed by method 1 and method 2 below.

(Method 1) A DNA library obtained after 5 rounds of selection and DeepVent DNA polymerase (0.02 units/µl) were used in combination with a 5'-primer (5'-CGTTG-TAAAACGACGGCCAGGATAATACGACTCACTATAG-3'(SEQ ID NO: 12)) and a 3'-primer (5'-TTTCACACAG-GAAACAGCTATGAC-3'(SEQ ID NO: 11)) to perform 8 cycles of PCR in the presence of 50 µM NH$_2$-hx-dPnTP and dDsTP, and the full-length PCR product was purified by electrophoresis and used as a template for DNA sequencing to perform a sequencing reaction and analysis thereof.

For the DNA sequencing reaction, 25 cycles of PCR (96° C. for 10 seconds, 50° C. for 5 seconds, 60° C. for 4 minutes) were performed at the scale of a total volume of 20 µl by adding a primer (4 pmol, 5'-CGTTGTAAAACGACGGC-CAG-3' (SEQ ID NO: 13)), the PCR amplified DNA fragment (approximately 0.3 pmol), and dPa'TP (40 pmol) to 8 µl of Cycle Sequencing Mix of a commercially available BigDye Terminator v1.1 Cycle Sequencing Kit (Applied Biosystems). Unreacted dye terminator was removed from the reaction solution through Centri-Sep™ spin column (Applied Biosystems), and the remaining solution was dried under reduced pressure. To the residue was added 4 µl of a solution of Blue-Dextran diluted in formamide, and a part of the solution was analyzed by ABI377DNA sequencer. The gel composition used for analysis was 7% polyacrylamide –6M urea gel. The peak pattern of the sequence was analyzed by using Applied Biosystems PRISM sequencing analysis v3.2 software.

(Method 2) After 5 rounds of PCR and selection, a part of the resulting DNA was amplified by 8 cycles of PCR (94° C. for 30 seconds, 45° C. for 30 seconds, and 72° C. for 1 minute) using Premix Ex Taq (Takara) without adding any substrate for the unnatural base, and the PCR product was cloned with TOPO TA Cloning Kit Dual Promoter (Invitrogen). A normal sequencing reaction was performed on the individual clones by BigDye Terminator v3.1 Cycle Sequencing Kit (Applied Biosystems), and the flanking random regions each consisting of three bases were analyzed by a DNA sequencer (model 3100, Applied Biosystems) to determine the sequences of 66 clones.

Results

Figure 3:
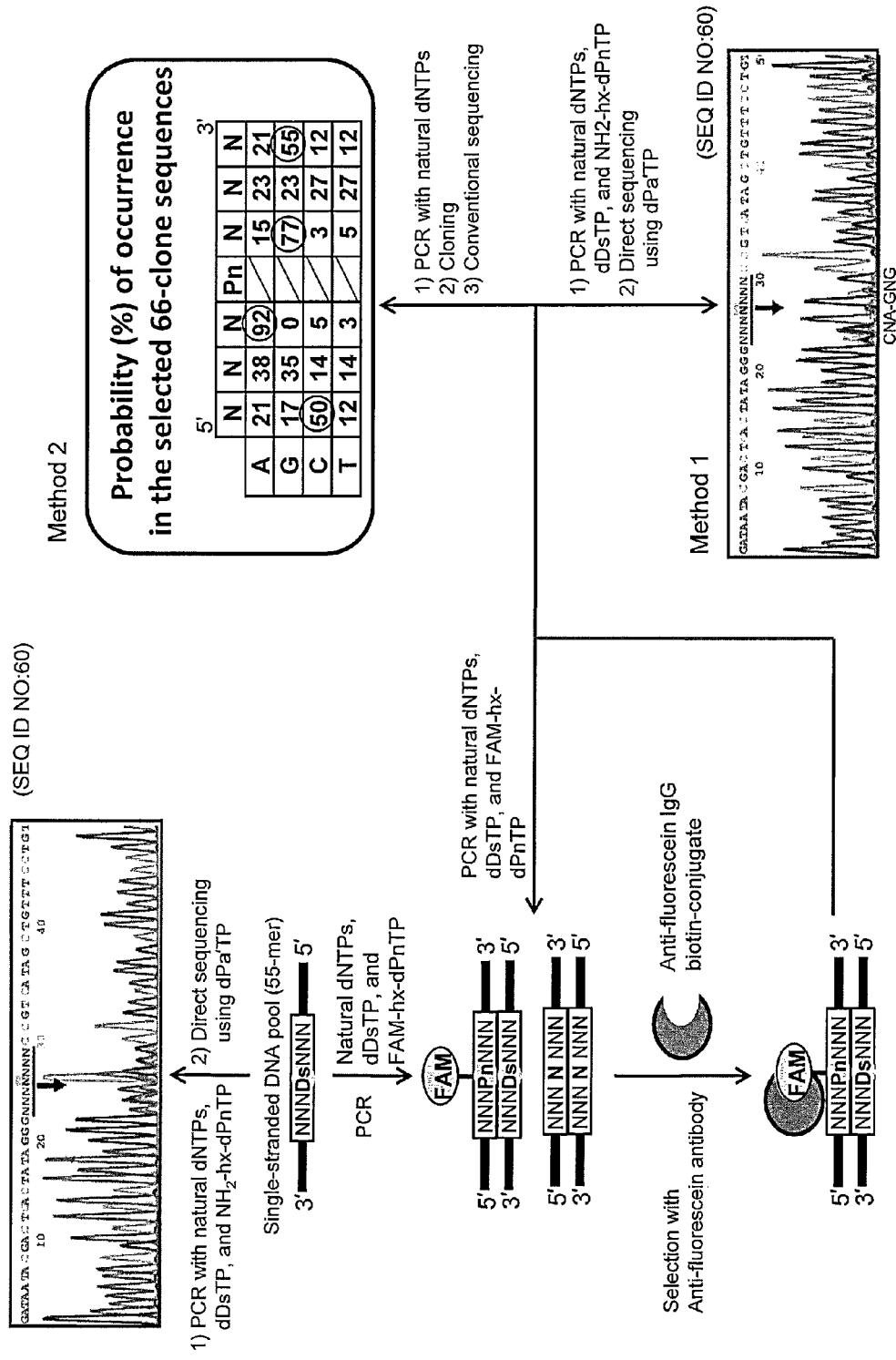
FIG. 3 depicts a schematic diagram of an experiment for determining the sequence of a natural base in the proximity of the unnatural base in DNA for achieving highly efficient and highly selective PCR amplification of DNA containing the unnatural base, as well as a table and a sequencing peak pattern showing the results.

The sequencing pattern of method 1 revealed convergence to sequence 5'-CNA(Pa)GNG-3' (SEQ ID NO: 14), i.e., 5'-CNC(Ds)TNG-3' (SEQ ID NO: 15) (wherein N represents any of A, G, C, T) (FIG. 3: the sequencing peak pattern shown as method 1). Similarly to method 1, evaluation of the frequency of occurrence of the bases at each site in the sequences obtained by cloning in method 2 gave sequence 5'-CNC(Ds) TNG-3' (wherein N represents any of A, G, C, T) (SEQ ID NO: 15), as shown in the table of method 2 in FIG. 3. This demonstrated that the efficiency and selectivity of PCR depend on not only bases adjacent to the unnatural base pair but also the third bases from the unnatural base toward both 5' and 3' ends.

(2-2: Results of In Vitro Selection and Analysis of DNA Sequence)

DNA fragments of the sequence obtained by cloning according to the sequence analysis of method 2 in the selection of Example 2 (S1-S8, (SEQ ID NOs: 16-23, respectively)), and DNA fragments unnaturally modified from the resulting sequence (N9-N12 (SEQ ID NOs: 24-27, respectively)) were synthesized by a DNA synthesizer, and each DNA fragment was evaluated for the amplification efficiency in PCR and its selectivity for the unnatural base.

In the presence of dDsTP and FAM-hx-dPnTP, 15 cycles of PCR were performed using primers labeled with $^{32}$P at their 5'-end, and the product was analyzed by gel electrophoresis. Specifically, the PCR reaction scale was 25 µl or 50 µl, and the reaction solution contained 20 mM Tris-HCl (pH 8.8), 10 mM KCl, 10 mM (NH$_4$)$_2$SO$_4$, 2 mM MgSO$_4$, 0.1% Triton X-100. One µM each of a 5'-primer (5'-CGTTGTAAAACGACGGC-CAGGATAATACGACTCACTATAG-3' (SEQ ID NO: 12)) and a 3'-primer (5'-TTTCACACAGGAAACAGCTATGAC-3' (SEQ ID NO: 11)) was used with a substrate dNTP for each natural base (0.3 mM), dDsTP (50 µM) and FAM-hx-dPnTP (2.5 µM) as substrates for the unnatural base, and DeepVent DNA polymerase (0.02 units/µl). PCR cycling included 94° C. for 30 seconds, 45° C. for 30 seconds, and 65° C. for 4 minutes per cycle. The concentration of the DNA fragment used as a template was 0.6 nM. After 15 cycles, the PCR product was separated by electrophoresis on 15% polyacrylamide –7M urea gel, and amplified DNA bands were detected/quantified by a bioimager FLA-7000 (Fujifilm). When the primers were labeled with $^{32}$P, radioactivity was analyzed by exposure of imaging plates. Fluorescence from FAM-hx-Pn incorporated into DNA by PCR amplification was detected in fluorescence analysis mode (laser: 473 nm, blue excitation filter Y520) by directly mounting the gel on the stage. The results are shown in Table 1.

TABLE 1

Relative fluorescence intensities and amplification efficiency of each DNA fragment amplified by 15-cycle PCR

| DNA | 5'-NNN Ds NNN-3' | Number of clones isolated in the selection | Relative fluorescence intensity incorporated into DNA | Relative efficiency of DNA fragments amplified by PCR | Relative fluorescence intensity/ Relative amplification efficiency |
|---|---|---|---|---|---|
| S1 (SEQ ID NO: 16) | CAC Ds TTG | 3 | 2.89 | 2.04 | 1.42 |
| S2 (SEQ ID NO: 17) | CCC Ds TTG | 4 | 2.63 | 1.85 | 1.42 |
| S3 (SEQ ID NO: 18) | CGC Ds TTG | 2 | 2.58 | 1.83 | 1.41 |

TABLE 1-continued

Relative fluorescence intensities and amplification efficiency of each DNA fragment amplified by 15-cycle PCR

| DNA | 5'-NNN Ds NNN-3' | Number of clones isolated in the selection | Relative fluorescence intensity incorporated into DNA | Relative efficiency of DNA fragments amplified by PCR | Relative fluorescence intensity/ Relative amplification efficiency |
|---|---|---|---|---|---|
| S4 (SEQ ID NO: 19) | TAC Ds TTG | 3 | 2.45 | 1.85 | 1.32 |
| S5 (SEQ ID NO: 20) | CAC Ds TCG | 2 | 2.45 | 1.85 | 1.32 |
| S6 (SEQ ID NO: 21) | TGC Ds TTG | 3 | 2.37 | 1.85 | 1.28 |
| S7 (SEQ ID NO: 22) | TAC Ds TCG | 1 | 2.11 | 1.78 | 1.19 |
| S8 (SEQ ID NO: 23) | ATC Ds TAT | 2 | 1.87 | 1.63 | 1.15 |
| N9 (SEQ ID NO: 24) | TAC Ds TTC | 0 | 1.76 | 1.28 | 1.38 |
| N10 (SEQ ID NO: 25) | TAG Ds TTG | 0 | 0.84 | 0.72 | 1.17 |
| N11 (SEQ ID NO: 26) | ATG Ds AAC | 0 | 0.11 | 0.20 | 0.55 |
| N12 (SEQ ID NO: 27) | TAC Ds GTG | 0 | 3.42 | 2.33 | 1.47 |
| Pool (SEQ ID NO: 1) | NNN Ds NNN | — | 1 | 1 | 1 |
| Cont (SEQ ID NO: 28) | ATC C TTA | 0 | 0.03 | 4.44 | — |
| | | Number of clones obtained by the selection; 0 means that the sequence was not obtained. | Intake of FAM-hx-dPnTP by PCR (detected by fluorescence of FAM) | Amplification efficiency of each DNA fragment by PCR (detected and quantitated by using $^{32}$P) | Selectivity of artificial base pair in PCR |

In this experiment, fluorescence intensities from amplified DNA bands were measured to evaluate the efficiency of incorporation of FAM-hx-dPnTP, and the intensities of $^{32}$P from the amplified DNA bands were measured to evaluate the amplification efficiency of DNA. The respective values were determined as relative intensities based on the initial library (Pool) used for the selection. The former measurement of the fluorescence intensity of FAM (Relative fluorescence intensity incorporated into DNA) depends on the abundance of the unnatural base pair in the amplified DNA, while the latter measurement of the radioisotope (Relative efficiency of DNA fragments amplified by PCR) represents relative abundance of the total amount of amplified DNA. Thus, the former value divided by the latter value (Fluorescence intensity/Relative amplification efficiency) represents the relative fidelity (selectivity) of the unnatural base pair in each sequence in PCR.

The DNA fragments obtained by selection (S1-S8 (SEQ ID NOs: 16-23, respectively)) contain sequence 5'-YNC(Ds)TYG-3' (Y=C or T, N=A, G, C, or T) (SEQ ID NO: 29) at high frequency, and the PCR amplification efficiency of these DNA fragments improved to 1.6 times to 2.0 times higher than DNA fragments of random sequences. The incorporation efficiency of FAM-hx-Pn also improved to 1.9 times to 2.9 times higher than DNA fragments of random sequences. Moreover, the fidelity (selectivity) of the unnatural base pair also correlates with these values, indicating that the selectivity and efficiency of unnatural base pair in PCR depend on the sequence of natural bases in the proximity of the unnatural base pair.

It was shown that this sequence 5'-YNC(Ds)TYG-3' (SEQ ID NO: 29) can be optimized to a more efficient sequence by replacing the base at each site by another natural base. The sequence 5'-TAC(Ds)GTG-3' (N12; SEQ ID NO: 27) obtained by this optimization as well as the sequences 5'-CAC (Ds)TTG-3' (S1; SEQ ID NO: 16) and 5'-CCC(Ds)TTG-3' (S2; SEQ ID NO: 17) obtained by selection showed high values in both PCR amplification efficiency and selectivity.

These results demonstrated that a sequence including an unnatural base pair capable of being amplified by PCR at high efficiency/high selectivity can be found by in vitro selection using a DNA library containing randomized sequences of natural bases in the proximity of the unnatural base pair and that the resulting sequence can be optimized by partially replacing some bases by other bases.

Example 3

Sequencing Method of DNA Containing an Unnatural Base

The present inventors previously reported a sequencing method of DNA fragments containing the unnatural base Ds (I. Hirao, et al., Nature Methods, 3: 729-735 (2006).). This previous method using Ds-Pa base pair relied on the difference in sequencing pattern depending on the presence or absence of a substrate (dPa'TP) of a propynyl derivative of Pa, which is a complementary base to Ds. For example, sequencing of DNA fragments containing Ds by a dideoxy dye terminator method without adding dPa'TP gives a peak pattern indicating the termination of the sequencing reaction at the site of a base complementary to Ds in the template strand DNA. When sequencing is performed with dPa'TP, however, the reaction proceeds but gives a peak pattern indicating disappearance of a sequencing peak only at the site of a base complementary to Ds in the template strand DNA due to the absence of a dideoxy dye terminator of fluorescently labeled Pa' (FIG. 3b). The previous method determines the sequence of DNA containing the unnatural base by comparing these two sequencing patterns.

In this previous method, however, substrates for some natural bases in the proximity of Ds in the template strand DNA might be misincorporated into the Ds site depending on the sequence of the natural bases even if dPa'TP were not added, in which case the sequencing reaction proceeded and a clear sequencing peak pattern would not be obtained. In the present invention, therefore, a substrate of a propynyl-modified dideoxy derivative of Pa (ddPa') was chemically synthesized to terminate completely the sequencing reaction at the Ds site in the template strand DNA and added to perform sequencing. As a result, a sequencing pattern independent from DNA sequences in the proximity of Ds (a pattern in which peaks after the base complementary to Ds disappear) was successively obtained (FIG. 3a).

Note that the propynyl-modified dideoxy derivative substrate of Pa (ddPa'TP) was synthesized according to the following scheme.

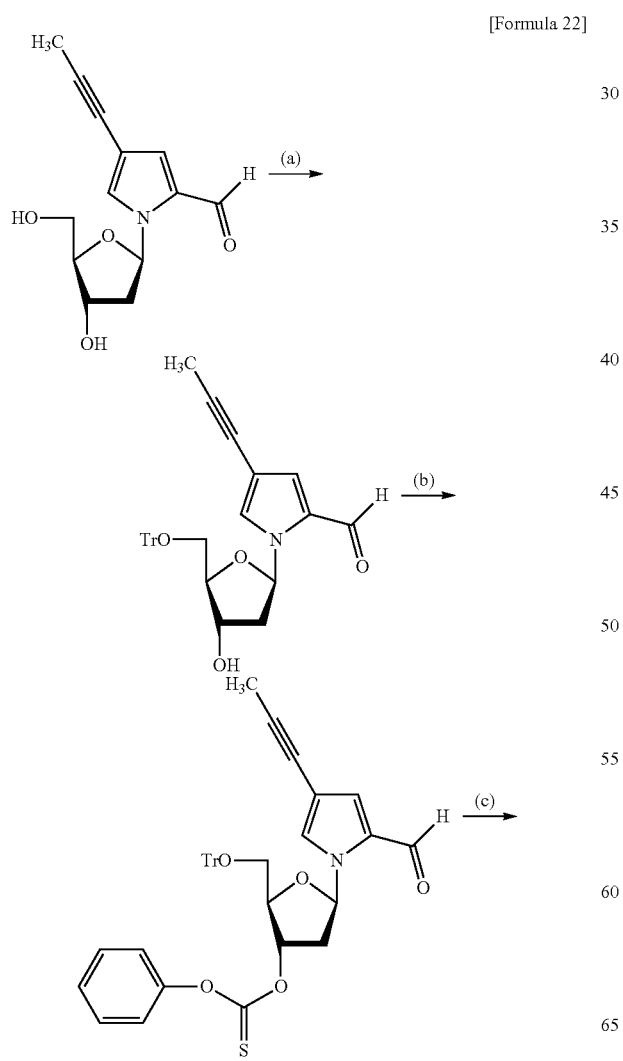

[Formula 22]

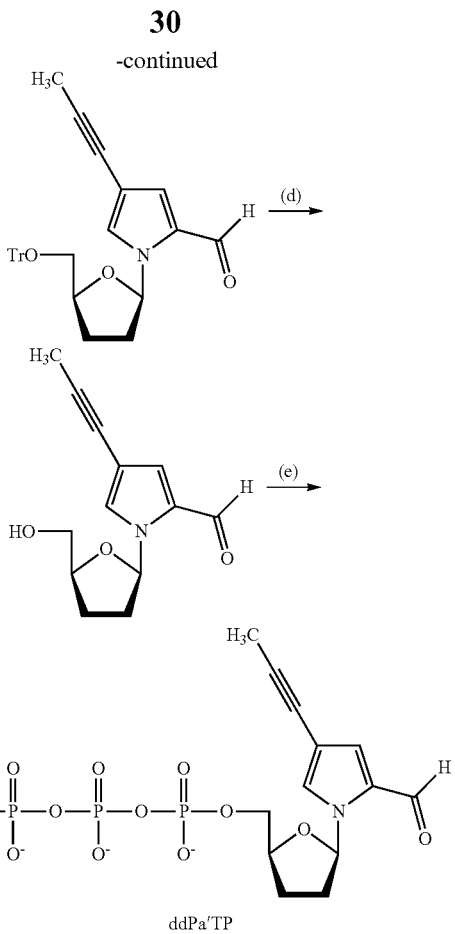

ddPa'TP

Step (a): Synthesis of 1-(2-deoxy-5-O-trityl-β-D-ribofuranosyl)-4-(1-propynyl)pyrrole-2-carbaldehyde To a solution of 1-(2-deoxy-β-D-ribofuranosyl)-4-(1-propynyl)pyrrole-2-carbaldehyde (249 mg, 1.00 mmol) (I. Hirao, et al., Nature Methods, 3: 729-735 (2006)) dissolved in anhydrous pyridine (10 ml) were added trityl chloride (1.18 g, 4.21 mmol) and N,N-diisopropylamine (1.11 ml, 6.40 mmol), and the reaction mixture was stirred at room temperature for 29 hours, and then at 50° C. for 1.5 hours. The reaction solution was concentrated under reduced pressure, and the residue was diluted with ethyl acetate, and the organic layers were washed twice with a saturated aqueous sodium bicarbonate solution and dried over magnesium sulfate. The resulting crude product was purified by column chromatography on silica gel (eluent:dichloromethane:ethyl acetate=100:0→400:3, then dichloromethane:methanol=100:2) to give the title product (395 mg, 80%).

$^1$H NMR (DMSO-d6) δ 9.51 (d, 1H, J=0.59 Hz), 7.63 (s, 1H), 7.50-7.23 (m, 15H), 7.12 (d, 1H, J=1.8 Hz), 6.67 (t, 1H, J=6.0 Hz), 5.32 (d, 1H, J=4.6 Hz), 4.32-4.22 (m, 1H), 4.00-3.90 (m, 1H), 3.25-3.10 (m, 2H), 2.40-2.28 (m, 1H), 2.28-2.15 (m, 1H), 1.95 (s, 3H).

HRMS (FAB, 3-NBA matrix): calculated for $C_{32}H_{29}N_1Na_1O_4$ [M+Na]$^+$, 514.1994; observed, 514.1992.

Steps (b) and (c): Synthesis of 1-(2,3-dideoxy-5-O-trityl-β-D-ribofuranosyl)-4-(1-propynyl)pyrrole-2-carbaldehyde To a solution of 1-(2-deoxy-5-O-trityl-β-D-ribofuranosyl)-4-(1-propynyl)pyrrole-2-carbaldehyde (392 mg, 797

µmol) in acetonitrile were added 4-dimethylaminopyridine (975 mg, 7.98 mmol) and phenyl chlorothioformate (470 µl, 3.40 mmol) in an argon atmosphere, and the reaction mixture was stirred at room temperature. After 23 hours, the reaction solution was concentrated under reduced pressure, and purified by column chromatography on silica gel (50-67% $CH_2Cl_2$ in hexane) to give an intermediate (193 mg, containing minor amounts of impurities). To a solution of this intermediate in toluene (10 ml) were added tri-n-butyltin hydride (165 µl, 612 µmol) and α,α'-azobisisobutyronitrile (15 mg, 92 µmol), and the reaction mixture was refluxed for 5 hours in an argon atmosphere. The reaction solution was concentrated under reduced pressure, and the resulting crude product was purified by column chromatography on silica gel (eluent: 50-80% $CH_2Cl_2$ in hexane) to give the title product (84 mg, 58%).

NMR (DMSO-d6) δ 9.52 (s, 1H), 7.64 (s, 1H), 7.50-7.23 (m, 15H), 7.12 (d, 1H, J=1.7 Hz), 6.53 (dd, 1H, J=1.6, 6.6 Hz), 4.26-4.20 (m, 1H), 3.25-3.19 (m, 2H), 2.45-2.32 (m, 1H), 2.10-1.80 (m, 3H), 1.94 (s, 3H).

HRMS (FAB, 3-NBA matrix):calculated for $C_{32}H_{29}N_1Na_1O_3$ $[M+Na]^+$, 498.2045; observed, 498.2072.

Step (d): Synthesis of 1-(2,3-dideoxy-β-D-ribofuranosyl)-4-(1-propynyl)pyrrole-2-carbaldehyde A solution of 1-(2,3-dideoxy-5-O-trityl-β-D-ribofuranosyl)-4-(1-propynyl)pyrrole-2-carbaldehyde (82 mg, 171 µmol) dissolved in 80% acetic acid (10 ml) was stirred at room temperature for 3 hours, and then at 50° C. for 2 hours. The reaction solution was concentrated under reduced pressure and repeated co-evaporation with water. The resulting crude product was purified by column chromatography on silica gel (0-1% $CH_3OH$ in $CH_2Cl_2$) and RP-HPLC (35-80% $CH_3CN$ in water, 12 min) to give the title product (31 mg, 78%).

$^1$H NMR (DMSO-d6) δ 9.45 (d, 1H, J=0.91 Hz), 7.95 (s, 1H), 7.10 (d, 1H, J=1.9 Hz), 6.47 (dd, 1H, J=2.2, 6.8 Hz), 5.04 (t, 1H, J=5.3 Hz), 4.20-4.10 (m, 1H), 3.69 (ddd, 1H, J=3.4, 5.7, 12.0 Hz), 3.54 (ddd, 1H, J=4.0, 4.9, 12.0 Hz), 2.46-2.32 (m, 1H), 1.97 (s, 3H), 1.96-1.78 (m, 3H).

$^{13}$C NMR (DMSO-d6) δ 179.94, 130.80, 130.56, 127.11, 105.87, 87.74, 85.38, 82.80, 73.91, 62.32, 34.73, 24.58, 4.30.

HRMS (FAB, 3-NBA matrix): calculated for $C_{13}H_{16}NO_3$ $[M+H]^+$, 234.1130; observed, 234.1137.

Step (e): Synthesis of 1-(2,3-dideoxy-β-D-ribofuranosyl)-4-(1-propynyl)pyrrole-2-carbaldehyde 5'-triphosphate (ddPa'TP)

A solution of 1-(2,3-dideoxy-β-D-ribofuranosyl)-4-(1-propynyl)pyrrole-2-carbaldehyde (20.8 mg, 89 mmol) dissolved in anhydrous pyridine (90 µl) and anhydrous dioxane (270 µl) was stirred with a 1M solution of 2 chloro-4H-1,3, 2-benzodioxaphosphorin-4-one in dioxane (100 µl, 100 µmol) at room temperature for 10 minutes, then stirred with tri-n-butylamine (90 µl) and a 0.5M solution of bis(tri-n-butyl ammonium) pyrophosphate in DMF (270 µl) for 10 minutes. The reaction mixture was stirred with a 1% iodine/water/pyridine solution (1.8 ml) at room temperature for 15 minutes, and a 5% aqueous sodium bisulfite solution (135 µl) was added and then the reaction solution was concentrated under reduced pressure. The resulting oily material was stirred with water (5 ml) at room temperature for 1 hour. This was purified by DEAF Sephadex A-25 column chromatography (1.5×30 cm, concentration linear gradient: 50 mM-1 M TEAB solution) and C18-HPLC (concentration gradient: 0%-15% acetonitrile in 0.1 M triethylammonium acetate buffer, pH 7.0) to give the title product.

$^1$H NMR (D$_2$O) δ 9.21 (d, 1H, J=0.76 Hz), 7.62 (s, 1H), 7.04 (d, 1H, J=1.7 Hz), 6.49 (dd, 1H, J=2.8, 6.8 Hz), 4.30-4.24 (m, 1H), 4.09 (ddd, 1H, J=3.2, 6.3, 11.4 Hz), 4.00-3.90 (m, 1H), 3.04 (q, 18H, J=7.3 Hz), 2.45-2.30 (m, 1H), 2.10-1.92 (m, 2H), 1.97 (s, 3H), 1.95-1.75 (m, 1H), 1.84 (s, 3H), 1.12 (t, 27H, J=7.3 Hz).

$^{31}$P NMR (D$_2$O) δ −23.28, −10.98, −10.98.

MS (ESI): calculated for $C_{13}H_{17}N_1O_{12}P_3$ $[M-H]^-$, 472.00; observed, 471.94.

Example 4

Method for Incorporating an Unnatural Base Bearing a Functional Substituent Into DNA by PCR Amplification and Detection/Isolation Method Thereof (4-1: PCR Amplification of DNA Containing an Unnatural Base)

A fragment containing Ds (55-mer) was subjected to 15-40 cycles of PCR with primers and substrates for the unnatural base (dDsTP and FAM-hx-dPnTP or NH$_2$-hx-dPnTP).

The PCR reaction scale was 25 µl or 50 µl, and the reaction solution contained 20 mM Tris-HCl (pH 8.8), 10 mM KCl, 10 mM (NH$_4$)$_2$SO$_4$, 2 mM MgSO$_4$, 0.1% Triton X-100. PCR was performed using a 5' primer (5'-CGTTGTAAAAC-GACGGCCAGGATAATACGACTCACTATAG-3' (SEQ ID NO: 12)) and a 3' primer (5'-TFICACACAGGAAACAGC-TATGAC-3' (SEQ ID NO: 11)) (each 1 µM), a substrate dNTP for each natural base (0.3 mM), dDsTP (50 µM), FAM-hx-dPnTP (2.5 µM) or NH$_2$-hx-dPnTP (50 µM), DeepVent DNA polymerase (0.02 units/µl). PCR cycling included 94° C. for 30 seconds, 45° C. or 42° C. for 30 seconds, and 65° C. for 4 minutes per cycle. The concentration of the DNA fragment used as a template was 0.6 fM-0.6 nM. The PCR product was separated by electrophoresis on 15% polyacrylamide −7M urea gel, and the product bands were detected/quantified by a bioimager FLA-7000 (Fujifilm). When the primers were labeled with $^{32}$P, the radioactivity was analyzed by exposure of imaging plates, and fluorescence from FAM-hx-Pn incorporated into DNA by PCR amplification was detected in fluorescence analysis mode (laser: 473 nm, blue excitation filter Y520) by directly mounting the gel on the stage.

Figures 1, 5:
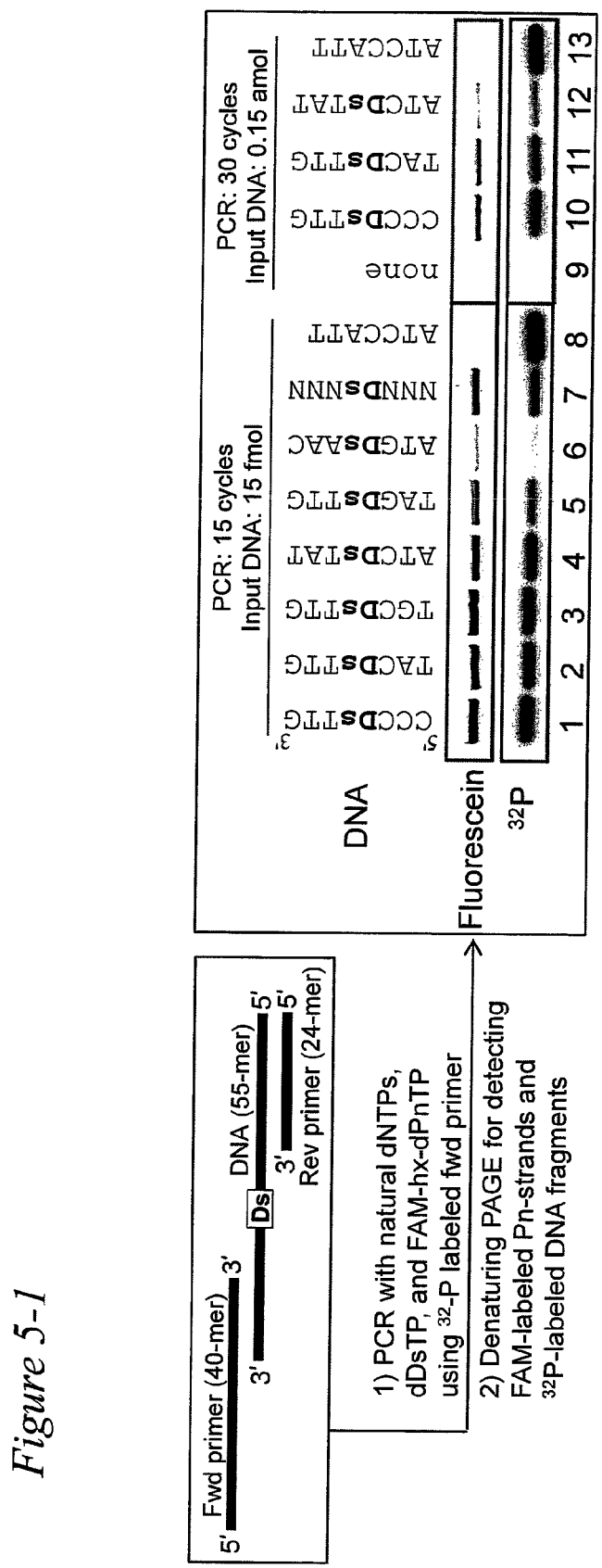
Figures 2, 5:
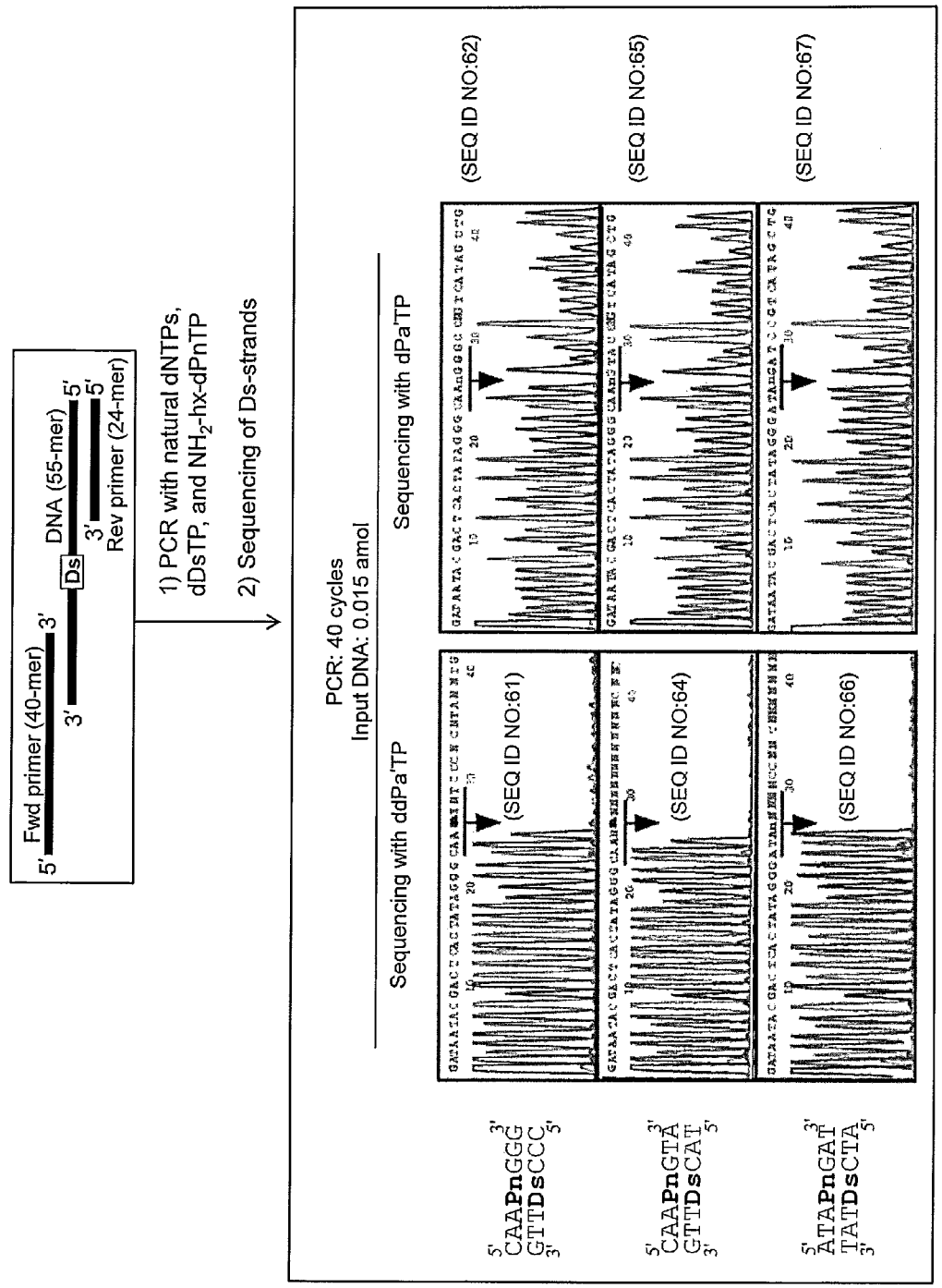

In PCR using FAM-hx-dPnTP, amplified products could be observed after 15 cycles (annealing temperature 45° C.) when the template concentration was 0.6 nM (15 fmol at a 25 µl scale), while amplified products could be observed after 30 cycles (annealing temperature 42° C.) when the template concentration was 6 fM (0.15 amol at a 25 µl scale). Thus, a DNA fragment containing Ds in an amount equivalent to 15 fmol was amplified to about 300 times after 15 cycles of PCR, and the DNA fragment in an amount equivalent to 0.15 amol was amplified to about 10$^7$ times after 30 cycles of PCR by the method using FAM-hx-dPnTP (FIG. 5-1).

In sequencing analysis, the product amplified by 40 cycles of PCR (annealing temperature 45° C.) at a template concentration of 0.6 fM (0.015 amol at a 25 µl scale) using NH$_2$-hx-dPnTP was purified by gel electrophoresis, and then its sequence was confirmed by a DNA sequencer. See (method 1) in Example 2-1 and Example 3 for the sequencing method. The results showed that the unnatural base Ds was almost completely conserved in DNA even after 40 cycles of PCR amplification. In PCR using NH$_2$-hx-dPnTP, a DNA fragment containing Ds in an amount equivalent 0.015 amol was amplified to about 10⁸ times after 40 cycles of PCR, and its sequence was also successfully confirmed (FIG. 5-2).

(4-2: PCR Amplification of DNA Containing Multiple Unnatural Bases)

To determine whether a DNA fragment containing multiple unnatural bases can be amplified by PCR, 15 cycles of PCR were performed using fragments containing two Ds moieties (60-mer, 62-mer, 65-mer, 68-mer) as templates with primers and substrates for the unnatural base (dDsTP and FAM-hx-dPnTP or NH₂-hx-dPnTP).

The DNA fragments containing two Ds moieties used are shown below.

Sequence of a DNA fragment containing two Ds moieties (60-mer) (SEQ ID NO: 33):

```
5'-TTTCACACAGGAAACAGCTATGACGGCCC(Ds)TTAC(Ds)
GTGCCCTATAGTGAGTCGTATTATC-3'
```

Sequence of a DNA fragment containing two Ds moieties (62-mer) (SEQ ID NO: 34):

```
5'-TTTCACACAGGAAACAGCTATGACGGCCC(Ds)TTGTAC(Ds)
GTGCCCTATAGTGAGTCGTATTATC-3'
```

Sequence of a DNA fragment containing two Ds moieties (65-mer) (SEQ ID NO: 35):

```
5'-TTTCACACAGGAAACAGCTATGACGGCCC(Ds)TTGTAATAC(Ds)
GTGCCCTATAGTGAGTCGTATTATC-3'
```

Sequence of a DNA fragment containing two Ds moieties (68-mer) (SEQ ID NO: 36):

```
5'-TTTCACACAGGAAACAGCTATGACGGCCC(Ds)TTGTAACGATAC
(Ds)
GTGCCCTATAGTGAGTCGTATTATC-3'.
```

The PCR reaction scale was 25 μl, and the reaction solution contained 20 mM Tris-HCl (pH 8.8), 10 mM KCl, 10 mM (NH₄)₂SO₄, 2 mM MgSO₄, 0.1% Triton X-100. PCR was performed using a 5' primer (5'-CGTTGTAAAACGACG-GCCAGGATAATACGACTCACTATAG-3' (SEQ ID NO: 12)) and a 3' primer (5'-TTTCACACAGGAAACAGCTAT-GAC-3' (SEQ ID NO: 11)) (each 1 μM), a substrate dNTP for each natural base (0.3 mM), dDsTP (50 μM), FAM-hx-dPnTP (2.5 μM) or NH₂-hx-dPnTP (50 μM), and Deep Vent DNA polymerase (0.02 units/μl). PCR cycling included 94° C. for 30 seconds, 45° C. for 30 seconds, and 65° C. for 4 minutes per cycle. The concentration of the DNA fragments used as templates was 0.6 nM. The PCR product was separated by electrophoresis on 15% polyacrylamide –7 M urea gel, and the product bands were detected/quantified by a bioimager FLA-7000 (Fujifilm). Fluorescence from FAM-hx-Pn incorporated into DNA by PCR amplification was detected in fluorescence analysis mode (laser: 473 nm, blue excitation filter Y520) by directly mounting the gel on the stage. In sequencing analysis, the PCR amplified product was purified by gel electrophoresis, and then a sequencing reaction was performed using dPa'TP at a final concentration of 50 μM, and the sequence was confirmed by a DNA sequencer. See (method 1) in Example 2-1 and Example 3 for the sequencing method.

Figure 6:
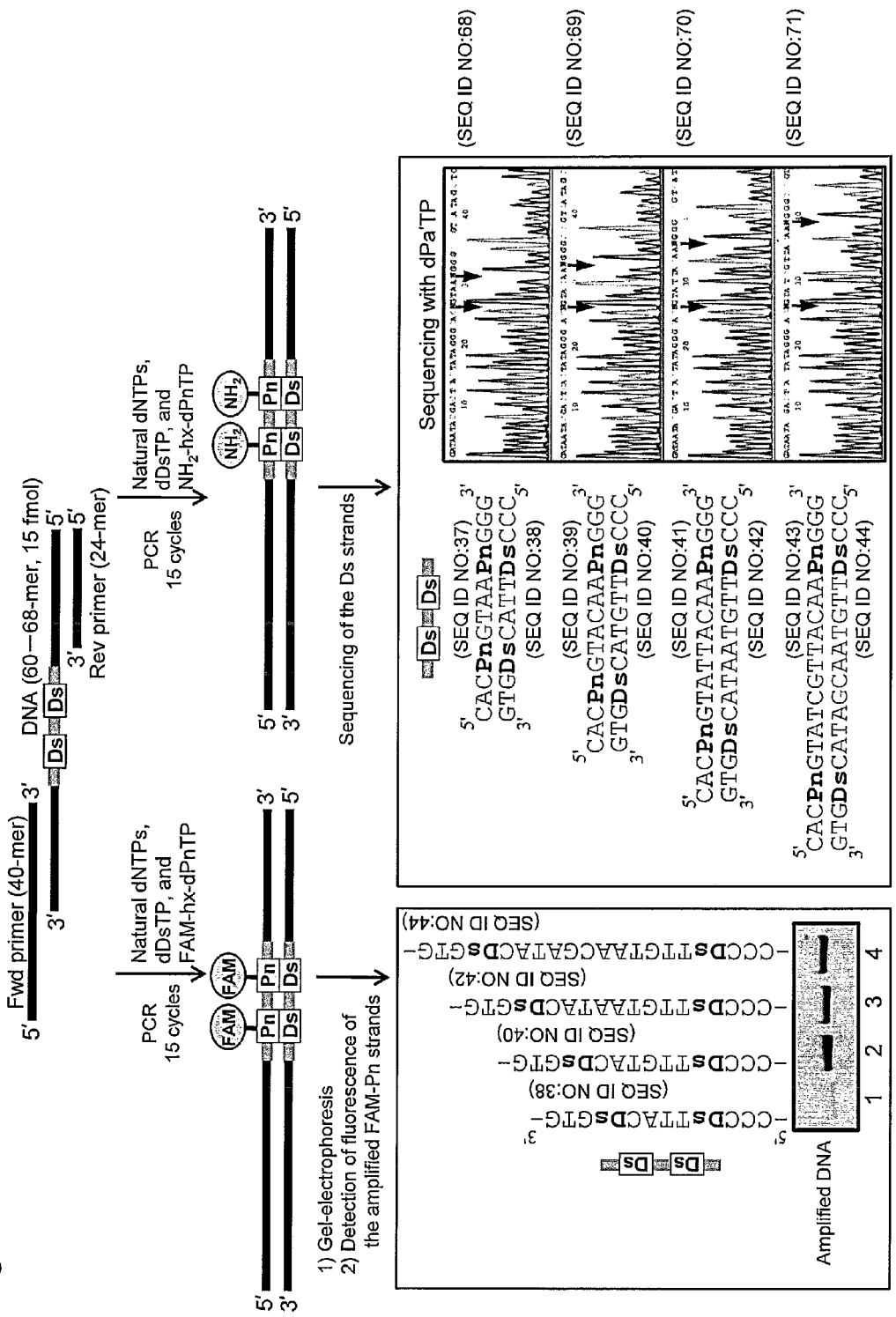
FIG. 6 depicts a schematic diagram of a PCR amplification experiment of DNA containing multiple unnatural bases, as well as an electrophoretogram showing the results and sequencing peak patterns showing the results of an analysis of the sequences of the amplified DNA products.

In PCR using FAM-hx-dPnTP, a DNA fragment containing the unnatural base was successfully detected from fluorescence of FAM-hx-Pn incorporated into amplified DNA by electrophoresis of the product after PCR amplification. A comparison of the amplification efficiencies in cases where the number of natural bases between two Ds moieties is 4 (a sequence of SEQ ID NO: 33), 6 (a sequence of SEQ ID NO: 34), 9 (a sequence of SEQ ID NO: 35), and 12 (a sequence of SEQ ID NO: 36) showed that efficient amplification occurs when two unnatural base moieties are separated by 6 bases or more (FIG. 6: gel electrophoretogram). In PCR using NH₂-hx-dPnTP, both two sites of the unnatural base Ds were almost completely conserved in DNA even after 15 cycles of PCR amplification, as demonstrated by sequencing pattern analysis (FIG. 6: sequencing pattern).

Example 5

PCR of a DNA Fragment Containing Ds in the Presence of Foreign DNA Fragments and Sequencing Thereof (1)

PCR amplification of a DNA fragment containing the unnatural base Ds allows incorporation of FAM-hx-Pn into its complementary DNA strand, whereby only the DNA fragment containing the unnatural base pair can be isolated with the aid of an anti-FAM antibody. In order to verify this, the following experiment was performed in the presence of an equal amount of three DNA fragments and a DNA fragment containing the unnatural base Ds, all of which have different sequences except for the primer regions, in the present Example.

PCR amplification of a DNA fragment containing the unnatural base Ds in the presence of DNA fragments solely consisting of natural bases having the same primer sequences and DNA sequencing analysis of the product were performed.

The sequences of four DNA fragments having the same primer sequences at both ends (including one DNA fragment containing Ds) are shown below.

```
DNA1 (55-mer) (SEQ ID NO: 45):
5'-TTTCACACAGGAAACAGCTATGACGGCCC(Ds)TTGCCCTATA
GTGAGTCGTATTATC-3'

DNA2 (55-mer) (SEQ ID NO: 46):
5'-TTTCACACAGGAAACAGCTATGACACATGGAACTGCTATAGT
GAGTCGTATTATC-3'

DNA3 (55-mer) (SEQ ID NO: 47):
5'-TTTCACACAGGAAACAGCTATGACCATGATGCAGACTATAGT
GAGTCGTATTATC-3'

DNA4 (55-mer) (SEQ ID NO: 48):
5'-TTTCACACAGGAAACAGCTATGACTTGATCCGTATCTATAGTGAGTC
GTATTATC-3'.
```

A mixture of these DNA fragments (final concentration of each fragment 0.15 nM) was used as a template in combination with FAM-hx-dPnTP (2.5 μM) and dDsTP (50 μM) and a substrate dNTP for each natural base (300 μM) to perform 15 cycles (94° C. for 30 seconds, 45° C. for 30 seconds, and 65° C. for 4 minutes) of PCR (50 μl scale) with DeepVent DNA polymerase. After amplification, a 20-μl aliquot of the PCR solution was passed through Microcon YM-30 (Millipore), and further washed with a buffer (20 mM Tris-HCl pH 7.6, 0.5 M NaCl, 10 mM MgCl₂) to remove unreacted substrates contained in the solution. This solution (30 μl) was mixed with a biotin-conjugated anti-FAM antibody (10 μl of a 1 mg/ml solution, Invitrogen) preliminarily immobilized on streptavidin magnetic beads (10 µl of a 4 mg/ml solution, New England Biolabs), and the mixture was incubated on ice for 1 hour. The magnetic beads stripped of the solution were washed twice with a buffer (100 µl), and then heated with 20 µl of a 1 mM EDTA solution (pH 8.0) at 75° C. for 30 seconds to elute DNA bound to the beads. A sequencing reaction was performed using 10 µl of the eluted DNA solution in the presence of dPa'TP (final concentration 2 µM). As a control, a part of each sample before purification with the anti-FAM antibody, i.e. immediately after PCR was purified by gel electrophoresis, and the product was used to perform a sequencing reaction.

Figure 7:
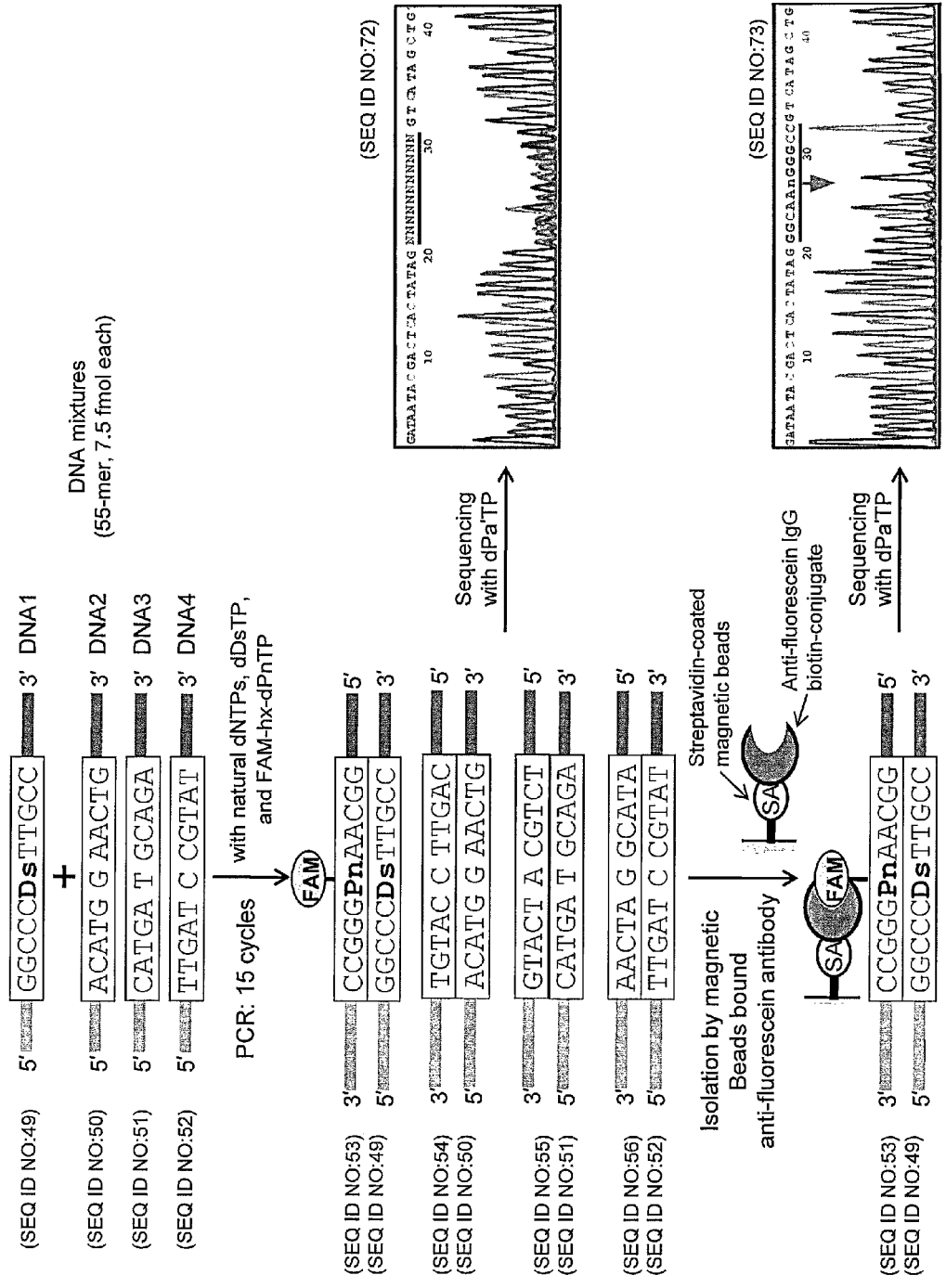
FIG. 7 depicts a schematic diagram of a PCR amplification and isolation experiment of a DNA fragment containing Ds under the conditions where foreign DNA coexists, and sequencing peak patterns of the amplified nucleic acid products at different stages of the experiment.

As shown in FIG. 7, the fragment containing the unnatural base becomes buried in the other sequences when the samples are subjected to sequencing immediately after PCR, but the nucleotide sequence of the DNA fragment containing Ds can be analyzed by sequencing after the fragment containing the unnatural base has been isolated from the PCR product with the aid of an anti-FAM antibody. Thus, only the DNA fragment containing the unnatural base pair can be isolated and its sequence can be determined by the method described above even if foreign DNA fragments having the same primer sequences at both ends but not containing the unnatural base coexist.

Example 6

PCR of a DNA Fragment Containing Ds in the Presence of Foreign DNA Fragments and Sequencing Thereof (2)

The present Example shows that the nucleotide sequence of a DNA fragment containing Ds can be analyzed by amplifying the DNA fragment containing Ds (55-mer, 0.3 amol) with a $10^7$-fold excess of a 100-mer fragment consisting of a random sequence of natural bases by PCR (30 cycles) and isolating only the DNA fragment containing the unnatural base with the aid of an anti-FAM antibody.

The sequence of a DNA fragment containing Ds (55-mer) is shown below (SEQ ID NO: 45):

5'-TTTCACACAGGAAACAGCTATGACGGCCC(Ds)TTGCCCTATAGT

GAGTCGTATTATC-3'.

Figure 8:
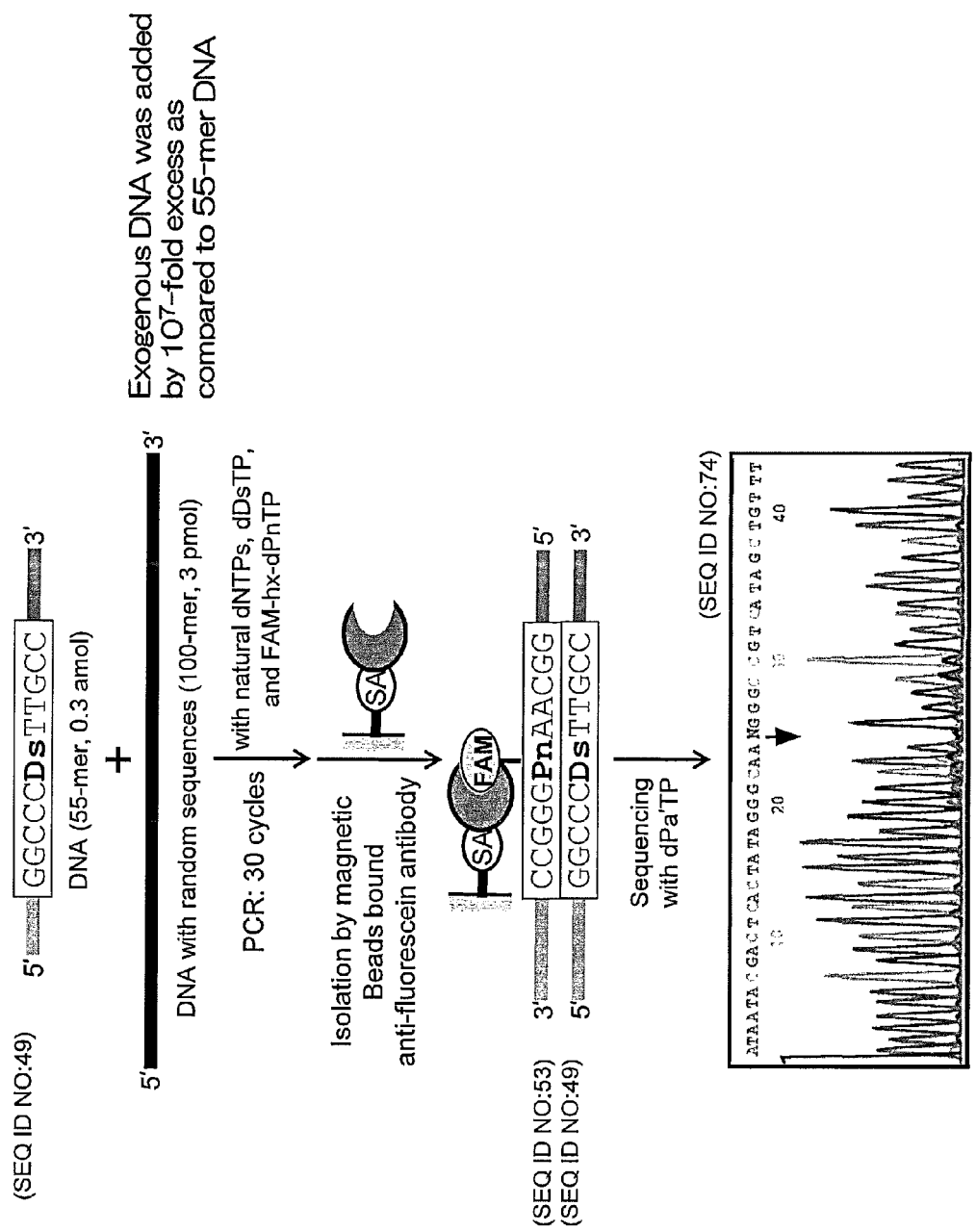
FIG. 8 depicts a schematic diagram of a PCR amplification and isolation experiment of a DNA fragment containing Ds under the conditions where foreign DNA coexists, and a sequencing peak pattern of the amplified and isolated nucleic acid containing the unnatural base pairs.

This DNA fragment (final concentration 6 fM) was subjected to 30 cycles of PCR (94° C. for 30 seconds, 45° C. for 30 seconds, and 65° C. for 4 minutes) (50 µl scale) with DeepVent DNA polymerase using FAM-hx-dPnTP (2.5 µM) and dDsTP (50 µM) as a substrate for the unnatural base, and dNTP (300 µM) as a substrate for each natural base in the presence of a 100-mer DNA fragment consisting of a random sequence of natural bases (final concentration 60 nM). A 20 µl aliquot of this solution was treated through a Centri-Sep™ spin column to remove excessive amounts of the substrates. The resulting solution was prepared into a solution containing 20 mM Tris-HCl pH 7.6, 0.5 M NaCl, 1 mM EDTA at final concentrations (40-50 µl), and this solution was mixed with a biotin-conjugated anti-FAM antibody (5 µl of a 1 mg/ml solution, Invitrogen) preliminarily immobilized on streptavidin magnetic beads (20 µl of a 4 mg/ml solution, New England Biolabs), and the mixture was incubated on ice for 30 minutes. The magnetic beads stripped of the solution were washed once with a buffer (100 µl), then heated with 20 µl of a 1 mM EDTA solution (pH 8.0) at 75° C. for 30 seconds to elute DNA bound to the beads. Sequencing was performed using 10 µl of the eluted DNA solution in the presence of dPa'TP (final concentration 2 µM). As shown in FIG. 8, the fragment containing the unnatural base could be isolated from the PCR product with the aid of an anti-FAM antibody even in the presence of a large excess of random DNA fragments, and then, the nucleotide sequence of the DNA fragment containing Ds could be analyzed by sequencing.

INDUSTRIAL APPLICABILITY

Even unmodified nucleotide 5'-triphosphates can be used as replication substrates for all bases (each of the base Ds, Pn derivative, A, G, C, T) in a replication reaction of a nucleic acid containing an unnatural base by using an unnatural base pair of a derivative bearing a substituent having a π-electron system attached to position 4 of the unnatural base Pn of the present invention (Pn derivative) and the unnatural base Ds. Moreover, a functional substituent can be added to the Pn derivative, whereby the functional substituent can be regioselectively incorporated into DNA and the resulting DNA bearing the substituent per se can be replicated by using the unnatural base of the present invention. Furthermore, the conservation rate of the unnatural base pair of the present invention in a nucleic acid replication reaction is very high. These distinguishing features are expected to lead to applications to various nucleic acid replication/amplification techniques such as in vitro selection methods handling minor amounts of DNA, DNA-based authentification techniques, etc.

The invention claimed is:

1. A method for replicating a nucleic acid containing an unnatural base pair, comprising performing a nucleic acid replication reaction on a template strand which is a nucleic acid containing a nucleotide having a base of formula I below:

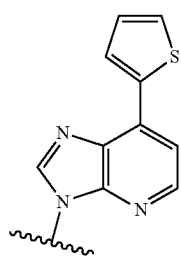

(hereinafter referred to as Ds), and/or a base of formula II below:

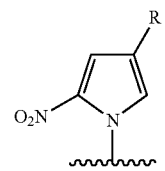

wherein R is —X—Y, or R is

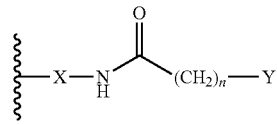

or R is

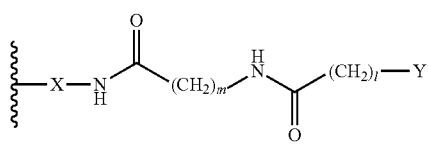

wherein
n is an integer selected from 1 to 12;
m is an integer selected from 1 to 12;
l is an integer selected from 1 to 12;
X is selected from a group consisting of —C≡C—CH2—, —C≡C—, —C=C—, aryl, thienyl, imidazolyl, and thiazolyl;
Y is selected from a group consisting of —CH3, —C2H5, —NH2, —OH, —COOH, —CHO, —SH, a substituted or unsubstituted aryl, —NHCO—Z, —CONH—Z, —NHCONH—Z, —O—Z, —COO—Z, —O—C(=O)—Z, —CO—Z, and —S—Z, wherein Z is selected from a group consisting of a fluorescent dye, biotin, an antibody-binding compound, a photo-crosslinker, a chelating agent, an amino acid and a peptide,
using a replication substrate containing the substituted or unsubstituted deoxyribonucleoside 5'-triphosphate having the base of formula II when the template strand contains a nucleotide having the base Ds, and using a replication substrate containing the substituted or unsubstituted deoxyribonucleoside 5'-triphosphate having the base Ds when the template strand contains a nucleotide having a base of formula II, thereby replicating a nucleic acid containing an unnatural base pair of the base Ds and a base of Formula II above.

2. The method of claim 1 wherein the template strand is a DNA containing at least two nucleotides having the base Ds and/or a base of formula II.

3. The method of claim 1 or 2 wherein the replication substrate is not a deoxyribonucleoside 5'-triphosphate substituted at the hydroxyl group of the γ-phosphate.

4. The method of claim 1 or 2, wherein the fluorescent dye is carboxyfluorescein (FAM).

5. A method for incorporating an unnatural base bearing a functional substituent attached thereto into DNA by a nucleic acid replication reaction, comprising performing a nucleic acid replication reaction on a template strand which is a nucleic acid containing a nucleotide having a base of formula I below:

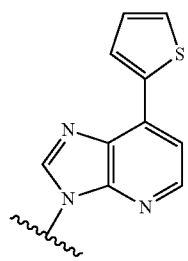

I (hereinafter referred to as Ds) using a substituted or unsubstituted deoxyribonucleoside 5'-triphosphate having a base of formula II below:

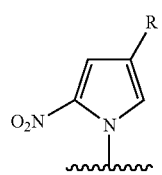

II wherein R is —X—Y, or R is

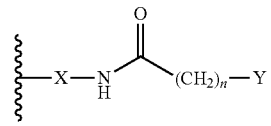

or R is

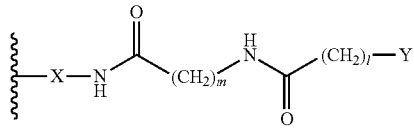

wherein
n is an integer selected from 1 to 12;
m is an integer selected from 1 to 12;
l is an integer selected from 1 to 12;
X is selected from a group consisting of —C≡C—CH$_2$—, —C≡C—, —C=C—, aryl, thienyl, imidazolyl, and thiazolyl;
Y is selected from a group consisting of —CH$_3$, —C$_2$H$_5$, —NH$_2$, —OH, —COOH, —CHO, —SH, a substituted or unsubstituted aryl, —NHCO—Z, —CONH—Z, —NHCONH—Z, —O—Z, —COO—Z, —O—C(=O)—Z, —CO—Z, and, —S—Z, wherein Z is selected from a group consisting of a fluorescent dye, biotin, an antibody-binding compound, a photo-crosslinker, a chelating agent, an amino acid and a peptide; the base Ds, and/or a natural base, as a replication substrate;
thereby generating a nucleic acid containing an unnatural base pair of the base Ds and a base of formula II above, whereby an unnatural base bearing a functional substituent attached thereto is incorporated into DNA.

6. The method of claim 5 wherein the template strand is a nucleic acid containing at least two nucleotides having the base Ds.

7. The method of claim 5 or 6 wherein the replication substrate is not a deoxyribonucleoside 5'-triphosphate substituted at the hydroxyl group of the γ-phosphate.

8. The method of claim 5 or 6 wherein the template strand includes a sequence of 5'-N$^1$N$^2$N$^3$(Ds)N$^4$N$^5$N$^6$-3' (SEQ ID NO: 1) as a flanking sequence of the base Ds, wherein N$^1$, N$^2$, N$^3$, N$^4$, N$^5$, N$^6$ are nucleotides having a natural base, provided that they satisfy two or more criteria of the group consisting of the following:
(a) N$^1$ is thymine (T) or cytosine (C);
(b) N$^3$ is cytosine (C);
(c) N$^4$ is thymine (T);
(d) N$^5$ is thymine (T) or cytosine (C); and
(e) N$^6$ is guanine (G).

9. The method of claim 8 wherein the fluorescent dye is carboxyfluorescein (FAM).

10. A method for replicating and selectively collecting a nucleic acid containing an unnatural base pair from a nucleic acid pool, comprising:
(1) performing a nucleic acid replication reaction on a nucleic acid pool including a nucleic acid containing a nucleotide having a base of formula I below:

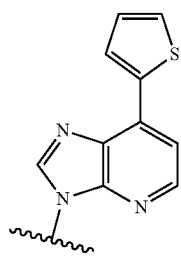

(hereinafter referred to as Ds) using a substituted or unsubstituted deoxyribonucleoside 5'-triphosphate having a base of formula II below:

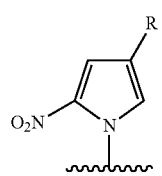

wherein R is —X—Y, or R is

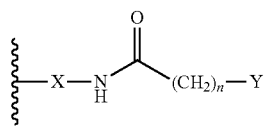

or R is

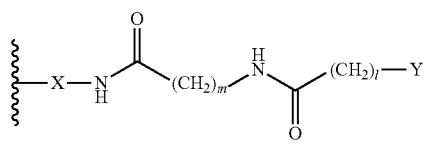

wherein
n is an integer selected from 1 to 12;
m is an integer selected from 1 to 12;
l is an integer selected from 1 to 12;
X is selected from a group consisting of —C≡C—CH$_2$—, —C≡C—, —C=C—, aryl, thienyl, imidazolyl, and thiazolyl;
Y is selected from a group consisting of —CH$_3$, —C$_2$H$_5$, —NH$_2$, —OH, —COOH, —CHO, —SH, a substituted or unsubstituted aryl, —NHCO—Z, —CONH—Z, —NHCONH—Z, —O—Z, —COO—Z, —O—C(=O)—Z, —CO—Z, and, —S—Z, wherein Z is selected from a group consisting of a fluorescent dye, biotin an antibody-binding compound, a photocrosslinker, a chelating agent, an amino acid and a peptide;
(2) selectively collecting a nucleic acid containing an unnatural base pair of the base Ds and a base of formula II above from the resulting nucleic acids on the basis of the properties of the functional substituent borne by the base of formula II above.

11. The method of claim 10 wherein the nucleic acid containing a nucleotide having the base Ds contains at least two nucleotides having the base Ds.

12. The method of claim 10 or 11 wherein the replication substrate is not a deoxyribonucleoside 5'-triphosphate substituted at the hydroxyl group of the γ-phosphate.

13. The method of claim 10 or 11 wherein the nucleic acid containing a nucleotide having the base Ds includes a sequence of 5'-N$^1$N$^2$N$^3$(Ds)N$^4$N$^5$N$^6$-3' (SEQ ID NO: 1) as a flanking sequence of the base Ds, wherein N$^1$, N$^2$, N$^3$, N$^4$, N$^5$, N$^6$ are nucleotides having a natural base, provided that they satisfy two or more criteria of the group consisting of the following:
(a) N$^1$ is thymine (T) or cytosine (C);
(b) N$^3$ is cytosine (C);
(c) N$^4$ is thymine (T);
(d) N$^5$ is thymine (T) or cytosine (C); and
(e) N$^6$ is guanine (G).

14. The method of claim 13 wherein the fluorescent dye is carboxyfluorescein (FAM).

15. A method for determining the sequence of natural bases in the proximity of an unnatural base in DNA, achieving highly efficient and highly selective replication of a nucleic acid containing the unnatural base, comprising:
(1) preparing a DNA library including a random region comprising the sequence 5'-(N)$_n$(Ds)(N)$_m$-3' (SEQ ID NO: 3) containing a nucleotide having a base of formula I below:

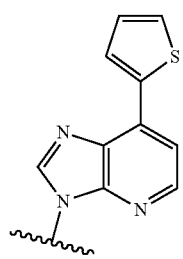

wherein n and m are each independently an integer selected from 1 to 10;
(2) performing a nucleic acid replication reaction on the DNA library using a substituted or unsubstituted deoxyribonucleoside 5'-triphosphate having a base of formula II below:

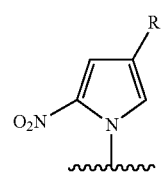

wherein R is —X—Y, or R is

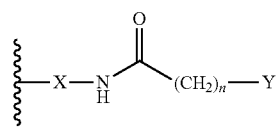

or R is

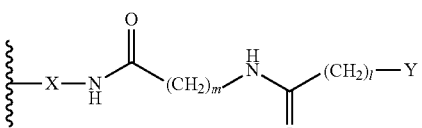

wherein n is an integer selected from 1 to 12;

m is an integer selected from 1 to 12;

l is an integer selected from 1 to 12;

X is selected from a group consisting of —C≡C—CH₂—, —C≡C—, —C=C—, aryl, thienyl, imidazolyl, and thiazolyl;

Y is selected from a group consisting of an aryl substituted by Z, —NHCO—Z, —CONH—Z, —NHCONH—Z, —O—Z, —COO—Z, —O—C(=O)—Z, —CO—Z, and —S—Z, wherein Z is a functional substituent selected from a group consisting of a fluorescent dye, biotin, an antibody-binding compound, a photocrosslinker, a chelating agent, an amino acid and a peptide; the base Ds, and/or a natural base, as a replication substrate;

(3) collecting a nucleic acid into which the functional substituent is introduced by the formation of an unnatural base pair of the base Ds and a base of formula II above, on the basis of the properties of the functional substituent;

(4) repeating steps (2) and (3) on the nucleic acid collected in (3); and (5) determining the sequence of the resulting nucleic acid.

16. The method of claim 15 wherein the replication substrate is not a deoxyribonucleoside 5'-triphosphate substituted at the hydroxyl group of the γ-phosphate.

17. A nucleic acid obtained by the method of claim 15 or 16.

18. A nucleic acid containing a nucleotide having an unnatural base that is a Pn derivative of the formula II:

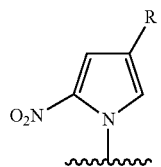

wherein R is —X—Y, or R is

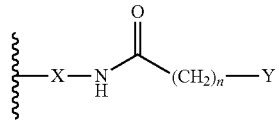

or R is

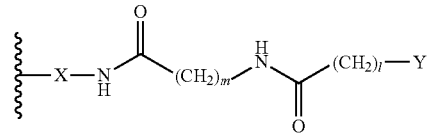

wherein n is an integer selected from 1 to 12;

m is an integer selected from 1 to 12;

l is an integer selected from 1 to 12;

X is selected from a group consisting of —C≡C—CH₂—, —C≡C—, —C=C—, aryl, thienyl, imidazolyl, and thiazolyl;

Y is selected from a group consisting of an aryl substituted by Z, —NHCO—Z, —CONH—Z, —NHCONH—Z, —O—Z, —COO—Z, —O—C(=O)—Z, —CO—Z, and —S—Z, wherein Z is a functional substituent selected from a group consisting of a fluorescent dye, biotin, an antibody-binding compound, a photocrosslinker, a chelating agent, an amino acid and a peptide;

said nucleic acid including a sequence of 5'-N¹'N²'N³'(Pn derivative) N⁴'N⁵'N⁶'-3' (SEQ ID NO: 4) as a flanking sequence of the unnatural base Pn derivative, wherein N¹', N²', N³', N⁴', N⁵', N⁶' are nucleotides having a natural base, provided that they satisfy two or more criteria of the group consisting of the following:

(a) N¹' is cytosine (C);

(b) N²' is adenine (A) or guanine (G);

(c) N³' is adenine (A);

(d) N⁴' is guanine (G); and (e) N⁶' is adenine (A) or guanine (G).

* * * * *

SEQUENCE LISTING

```
<160> NUMBER OF SEQ ID NOS: 74

<210> SEQ ID NO 1
<211> LENGTH: 7
<212> TYPE: DNA
<213> ORGANISM: Artificial sequence
<220> FEATURE:
<223> OTHER INFORMATION: random sequence containing Ds base
<220> FEATURE:
<221> NAME/KEY: misc_feature
<222> LOCATION: (1)..(3)
<223> OTHER INFORMATION: n stands for adenine, guanine, thymine, or
      cytosine
<220> FEATURE:
<221> NAME/KEY: misc_feature
<222> LOCATION: (5)..(7)
<223> OTHER INFORMATION: n stands for adenine, guanine, thymine, or
      cytosine
```

```
-continued

<220> FEATURE:
<221> NAME/KEY: misc_feature
<222> LOCATION: (4)..(4)
<223> OTHER INFORMATION: n stands for 7-(2-thienyl)-3H-
      imidazo[4,5-b]pyridin-3-yl

<400> SEQUENCE: 1 nnnnnnn                                                                    7

<210> SEQ ID NO 2
<211> LENGTH: 21
<212> TYPE: DNA
<213> ORGANISM: Artificial sequence
<220> FEATURE:
<223> OTHER INFORMATION: random sequence containing unnatural base
<220> FEATURE:
<221> NAME/KEY: misc_feature
<222> LOCATION: (1)..(10)
<223> OTHER INFORMATION: n stands for adenine, guanine, thymine, or
      cytosine
<220> FEATURE:
<221> NAME/KEY: misc_feature
<222> LOCATION: (12)..(21)
<223> OTHER INFORMATION: n stands for adenine, guanine, thymine, or
      cytosine
<220> FEATURE:
<221> NAME/KEY: misc_feature
<222> LOCATION: (11)..(11)
<223> OTHER INFORMATION: n stands for any unnatural base

<400> SEQUENCE: 2
nnnnnnnnnn nnnnnnnnnn n                                                   21

<210> SEQ ID NO 3
<211> LENGTH: 21
<212> TYPE: DNA
<213> ORGANISM: Artificial sequence
<220> FEATURE:
<223> OTHER INFORMATION: random sequence containing Ds base
<220> FEATURE:
<221> NAME/KEY: misc_feature
<222> LOCATION: (1)..(10)
<223> OTHER INFORMATION: n stands for adenine, guanine, thymine, or
      cytosine
<220> FEATURE:
<221> NAME/KEY: misc_feature
<222> LOCATION: (12)..(21)
<223> OTHER INFORMATION: n stands for adenine, guanine, thymine, or
      cytosine
<220> FEATURE:
<221> NAME/KEY: misc_feature
<222> LOCATION: (11)..(11)
<223> OTHER INFORMATION: n stands for 7-(2-thienyl)-3H-
      imidazo[4,5-b]pyridin-3-yl

<400> SEQUENCE: 3
nnnnnnnnnn nnnnnnnnnn n                                                   21

<210> SEQ ID NO 4
<211> LENGTH: 7
<212> TYPE: DNA
<213> ORGANISM: Artificial sequence
<220> FEATURE:
<223> OTHER INFORMATION: random sequence containing Pn derivative
<220> FEATURE:
<221> NAME/KEY: misc_feature
<222> LOCATION: (1)..(3)
<223> OTHER INFORMATION: n stands for adenine, guanine, thymine, or
      cytosine
<220> FEATURE:
<221> NAME/KEY: misc_feature
<222> LOCATION: (5)..(7)
<223> OTHER INFORMATION: n stands for adenine, guanine, thymine, or
      cytosine
```

```
<220> FEATURE:
<221> NAME/KEY: misc_feature
<222> LOCATION: (4)..(4)
<223> OTHER INFORMATION: n stands for 4-substituted 2-nitro-1H-
      pyrrol-1-yl

<400> SEQUENCE: 4 nnnnnnn                                                                     7

<210> SEQ ID NO 5
<211> LENGTH: 20
<212> TYPE: DNA
<213> ORGANISM: Artificial sequence
<220> FEATURE:
<223> OTHER INFORMATION: primer for single nucleotide insertion
      experiment

<400> SEQUENCE: 5
actcactata gggaggaaga                                                      20

<210> SEQ ID NO 6
<211> LENGTH: 20
<212> TYPE: DNA
<213> ORGANISM: Artificial sequence
<220> FEATURE:
<223> OTHER INFORMATION: primer for single nucleotide insertion
      experiment

<400> SEQUENCE: 6
actcactata gggagcttct                                                      20

<210> SEQ ID NO 7
<211> LENGTH: 35
<212> TYPE: DNA
<213> ORGANISM: Artificial sequence
<220> FEATURE:
<223> OTHER INFORMATION: template for single nucleotide insertion
      experiment
<220> FEATURE:
<221> NAME/KEY: misc_feature
<222> LOCATION: (7)..(7)
<223> OTHER INFORMATION: n stands for adenine, guanine, thymine,
      cytosine, or 7-(2-thienyl)-3H-imidazo[4,5-b]pyridin-3-yl

<400> SEQUENCE: 7
agctctntct tcctccctat agtgagtcgt attat                                     35

<210> SEQ ID NO 8
<211> LENGTH: 35
<212> TYPE: DNA
<213> ORGANISM: Artificial sequence
<220> FEATURE:
<223> OTHER INFORMATION: template for single nucleotide insertion
      experiment
<220> FEATURE:
<221> NAME/KEY: misc_feature
<222> LOCATION: (7)..(7)
<223> OTHER INFORMATION: n stands for 2-formyl-1H-pyrrol-1-yl or
      2-nitro-1H-pyrrol-1-yl

<400> SEQUENCE: 8
tcgaganaga agctccctat agtgagtcgt attat                                     35

<210> SEQ ID NO 9
<211> LENGTH: 55
<212> TYPE: DNA
<213> ORGANISM: Artificial sequence
<220> FEATURE:
<223> OTHER INFORMATION: DNA library containing Ds base
```

-continued

```
<220> FEATURE:
<221> NAME/KEY: misc_feature
<222> LOCATION: (27)..(29)
<223> OTHER INFORMATION: n stands for adenine, guanine, thymine, or
      cytosine
<220> FEATURE:
<221> NAME/KEY: misc_feature
<222> LOCATION: (31)..(33)
<223> OTHER INFORMATION: n stands for adenine, guanine, thymine, or
      cytosine
<220> FEATURE:
<221> NAME/KEY: misc_feature
<222> LOCATION: (30)..(30)
<223> OTHER INFORMATION: n stands for 7-(2-thienyl)-3H-
      imidazo[4,5-b]pyridin-3-yl

<400> SEQUENCE: 9
tttcacacag gaaacagcta tgacggnnnn nnnccctata gtgagtcgta ttatc          55

<210> SEQ ID NO 10
<211> LENGTH: 20
<212> TYPE: DNA
<213> ORGANISM: Artificial sequence
<220> FEATURE:
<223> OTHER INFORMATION: 5'-primer for in vitro selection experiment

<400> SEQUENCE: 10
gataatacga ctcactatag                                                 20

<210> SEQ ID NO 11
<211> LENGTH: 24
<212> TYPE: DNA
<213> ORGANISM: Artificial sequence
<220> FEATURE:
<223> OTHER INFORMATION: 3'-primer

<400> SEQUENCE: 11
tttcacacag gaaacagcta tgac                                            24

<210> SEQ ID NO 12
<211> LENGTH: 40
<212> TYPE: DNA
<213> ORGANISM: Artificial sequence
<220> FEATURE:
<223> OTHER INFORMATION: 5'-primer for sequencing method 1

<400> SEQUENCE: 12
cgttgtaaaa cgacggccag gataatacga ctcactatag                           40

<210> SEQ ID NO 13
<211> LENGTH: 20
<212> TYPE: DNA
<213> ORGANISM: Artificial sequence
<220> FEATURE:
<223> OTHER INFORMATION: primer for sequencing

<400> SEQUENCE: 13
cgttgtaaaa cgacggccag                                                 20

<210> SEQ ID NO 14
<211> LENGTH: 7
<212> TYPE: DNA
<213> ORGANISM: Artificial sequence
<220> FEATURE:
<223> OTHER INFORMATION: consensus sequence obtained from method 1:
      Pn-strand
```

```
-continued

<220> FEATURE:
<221> NAME/KEY: misc_feature
<222> LOCATION: (2)..(2)
<223> OTHER INFORMATION: n stands for adenine, guanine, thymine, or
      cytosine
<220> FEATURE:
<221> NAME/KEY: misc_feature
<222> LOCATION: (6)..(6)
<223> OTHER INFORMATION: n stands for adenine, guanine, thymine, or
      cytosine
<220> FEATURE:
<221> NAME/KEY: misc_feature
<222> LOCATION: (4)..(4)
<223> OTHER INFORMATION: n stands for 2-formyl-1H-pyrrol-1-yl,
      2-nitro-1H-pyrrol-1-yl, or 4-substituted 2-nitro-1H-pyrrol-1-yl

<400> SEQUENCE: 14 cnangng                                                                  7

<210> SEQ ID NO 15
<211> LENGTH: 7
<212> TYPE: DNA
<213> ORGANISM: Artificial sequence
<220> FEATURE:
<223> OTHER INFORMATION: consensus sequence obtained from method 1:
      Ds-strand
<220> FEATURE:
<221> NAME/KEY: misc_feature
<222> LOCATION: (2)..(2)
<223> OTHER INFORMATION: n stands for adenine, guanine, thymine, or
      cytosine
<220> FEATURE:
<221> NAME/KEY: misc_feature
<222> LOCATION: (6)..(6)
<223> OTHER INFORMATION: n stands for adenine, guanine, thymine, or
      cytosine
<220> FEATURE:
<221> NAME/KEY: misc_feature
<222> LOCATION: (4)..(4)
<223> OTHER INFORMATION: n stands for 7-(2-thienyl)-3H-
      imidazo[4,5-b]pyridin-3-yl

<400> SEQUENCE: 15 cncntng                                                                  7

<210> SEQ ID NO 16
<211> LENGTH: 7
<212> TYPE: DNA
<213> ORGANISM: Artificial sequence
<220> FEATURE:
<223> OTHER INFORMATION: S1 clone sequence
<220> FEATURE:
<221> NAME/KEY: misc_feature
<222> LOCATION: (4)..(4)
<223> OTHER INFORMATION: n stands for 7-(2-thienyl)-3H-
      imidazo[4,5-b]pyridin-3-yl

<400> SEQUENCE: 16 cacnttg                                                                  7

<210> SEQ ID NO 17
<211> LENGTH: 7
<212> TYPE: DNA
<213> ORGANISM: Artificial sequence
<220> FEATURE:
<223> OTHER INFORMATION: S2 clone sequence
<220> FEATURE:
<221> NAME/KEY: misc_feature
<222> LOCATION: (4)..(4)
<223> OTHER INFORMATION: n stands for 7-(2-thienyl)-3H-
      imidazo[4,5-b]pyridin-3-yl
```

```
<400> SEQUENCE: 17 cccnttg                                                              7

<210> SEQ ID NO 18
<211> LENGTH: 7
<212> TYPE: DNA
<213> ORGANISM: Artificial sequence
<220> FEATURE:
<223> OTHER INFORMATION: S3 clone sequence
<220> FEATURE:
<221> NAME/KEY: misc_feature
<222> LOCATION: (4)..(4)
<223> OTHER INFORMATION: n stands for 7-(2-thienyl)-3H-
      imidazo[4,5-b]pyridin-3-yl

<400> SEQUENCE: 18 cgcnttg                                                              7

<210> SEQ ID NO 19
<211> LENGTH: 7
<212> TYPE: DNA
<213> ORGANISM: Artificial sequence
<220> FEATURE:
<223> OTHER INFORMATION: S4 clone sequnce
<220> FEATURE:
<221> NAME/KEY: misc_feature
<222> LOCATION: (4)..(4)
<223> OTHER INFORMATION: n stands for 7-(2-thienyl)-3H-
      imidazo[4,5-b]pyridin-3-yl

<400> SEQUENCE: 19 tacnttg                                                              7

<210> SEQ ID NO 20
<211> LENGTH: 7
<212> TYPE: DNA
<213> ORGANISM: Artificial sequence
<220> FEATURE:
<223> OTHER INFORMATION: S5 clone sequence
<220> FEATURE:
<221> NAME/KEY: misc_feature
<222> LOCATION: (4)..(4)
<223> OTHER INFORMATION: n stands for 7-(2-thienyl)-3H-
      imidazo[4,5-b]pyridin-3-yl

<400> SEQUENCE: 20 cacntcg                                                              7

<210> SEQ ID NO 21
<211> LENGTH: 7
<212> TYPE: DNA
<213> ORGANISM: Artificial sequence
<220> FEATURE:
<223> OTHER INFORMATION: S6 clone sequence
<220> FEATURE:
<221> NAME/KEY: misc_feature
<222> LOCATION: (4)..(4)
<223> OTHER INFORMATION: n stands for 7-(2-thienyl)-3H-
      imidazo[4,5-b]pyridin-3-yl

<400> SEQUENCE: 21 tgcnttg                                                              7

<210> SEQ ID NO 22
<211> LENGTH: 7
<212> TYPE: DNA
<213> ORGANISM: Artificial sequence
<220> FEATURE:
<223> OTHER INFORMATION: S7 clone sequence
```

```
<220> FEATURE:
<221> NAME/KEY: misc_feature
<222> LOCATION: (4)..(4)
<223> OTHER INFORMATION: n stands for 7-(2-thienyl)-3H-
      imidazo[4,5-b]pyridin-3-yl

<400> SEQUENCE: 22 tacntcg                                                                   7

<210> SEQ ID NO 23
<211> LENGTH: 7
<212> TYPE: DNA
<213> ORGANISM: Artificial sequence
<220> FEATURE:
<223> OTHER INFORMATION: S8 clone sequence
<220> FEATURE:
<221> NAME/KEY: misc_feature
<222> LOCATION: (4)..(4)
<223> OTHER INFORMATION: n stands for 7-(2-thienyl)-3H-
      imidazo[4,5-b]pyridin-3-yl

<400> SEQUENCE: 23 atcntat                                                                   7

<210> SEQ ID NO 24
<211> LENGTH: 7
<212> TYPE: DNA
<213> ORGANISM: Artificial sequence
<220> FEATURE:
<223> OTHER INFORMATION: N9 sequence
<220> FEATURE:
<221> NAME/KEY: misc_feature
<222> LOCATION: (4)..(4)
<223> OTHER INFORMATION: n stands for 7-(2-thienyl)-3H-
      imidazo[4,5-b]pyridin-3-yl

<400> SEQUENCE: 24 tacnttc                                                                   7

<210> SEQ ID NO 25
<211> LENGTH: 7
<212> TYPE: DNA
<213> ORGANISM: Artificial sequence
<220> FEATURE:
<223> OTHER INFORMATION: N10 sequence
<220> FEATURE:
<221> NAME/KEY: misc_feature
<222> LOCATION: (4)..(4)
<223> OTHER INFORMATION: n stands for 7-(2-thienyl)-3H-
      imidazo[4,5-b]pyridin-3-yl

<400> SEQUENCE: 25 tagnttg                                                                   7

<210> SEQ ID NO 26
<211> LENGTH: 7
<212> TYPE: DNA
<213> ORGANISM: Artificial sequence
<220> FEATURE:
<223> OTHER INFORMATION: N11 sequence
<220> FEATURE:
<221> NAME/KEY: misc_feature
<222> LOCATION: (4)..(4)
<223> OTHER INFORMATION: n stands for 7-(2-thienyl)-3H-
      imidazo[4,5-b]pyridin-3-yl

<400> SEQUENCE: 26 atgnaac                                                                   7
```

-continued

```
<210> SEQ ID NO 27
<211> LENGTH: 7
<212> TYPE: DNA
<213> ORGANISM: Artificial sequence
<220> FEATURE:
<223> OTHER INFORMATION: N12 sequence
<220> FEATURE:
<221> NAME/KEY: misc_feature
<222> LOCATION: (4)..(4)
<223> OTHER INFORMATION: n stands for 7-(2-thienyl)-3H-
      imidazo[4,5-b]pyridin-3-yl

<400> SEQUENCE: 27 tacngtg                                                              7

<210> SEQ ID NO 28
<211> LENGTH: 7
<212> TYPE: DNA
<213> ORGANISM: Artificial sequence
<220> FEATURE:
<223> OTHER INFORMATION: control sequence

<400> SEQUENCE: 28 atcctta                                                              7

<210> SEQ ID NO 29
<211> LENGTH: 7
<212> TYPE: DNA
<213> ORGANISM: Artificial sequence
<220> FEATURE:
<223> OTHER INFORMATION: consensus sequence obtained by method 2:
      Ds-strand
<220> FEATURE:
<221> NAME/KEY: misc_feature
<222> LOCATION: (2)..(2)
<223> OTHER INFORMATION: n stands for adenine, guanine, thymine, or
      cytosine
<220> FEATURE:
<221> NAME/KEY: misc_feature
<222> LOCATION: (4)..(4)
<223> OTHER INFORMATION: n stands for 7-(2-thienyl)-3H-
      imidazo[4,5-b]pyridin-3-yl

<400> SEQUENCE: 29 yncntyg                                                              7

<210> SEQ ID NO 30
<211> LENGTH: 7
<212> TYPE: DNA
<213> ORGANISM: Artificial sequence
<220> FEATURE:
<223> OTHER INFORMATION: complementary sequence of S2 clone
<220> FEATURE:
<221> NAME/KEY: misc_feature
<222> LOCATION: (4)..(4)
<223> OTHER INFORMATION: n stands for 4-substituted 2-nitro-1H-
      pyrrol-1-yl

<400> SEQUENCE: 30 caanggg                                                              7

<210> SEQ ID NO 31
<211> LENGTH: 7
<212> TYPE: DNA
<213> ORGANISM: Artificial sequence
<220> FEATURE:
<223> OTHER INFORMATION: complementary sequence of S4 clone
<220> FEATURE:
<221> NAME/KEY: misc_feature
<222> LOCATION: (4)..(4)
<223> OTHER INFORMATION: n stands for 4-substituted 2-nitro-1H-
      pyrrol-1-yl
```

-continued

```
<400> SEQUENCE: 31 caangta                                                                    7

<210> SEQ ID NO 32
<211> LENGTH: 7
<212> TYPE: DNA
<213> ORGANISM: Artificial sequence
<220> FEATURE:
<223> OTHER INFORMATION: complementary sequence of S8 clone
<220> FEATURE:
<221> NAME/KEY: misc_feature
<222> LOCATION: (4)..(4)
<223> OTHER INFORMATION: n stands for 4-substituted 2-nitro-1H-
      pyrrol-1-yl

<400> SEQUENCE: 32 atangat                                                                    7

<210> SEQ ID NO 33
<211> LENGTH: 60
<212> TYPE: DNA
<213> ORGANISM: Artificial sequence
<220> FEATURE:
<223> OTHER INFORMATION: 60-mer DNA containing 2 Ds bases
<220> FEATURE:
<221> NAME/KEY: misc_feature
<222> LOCATION: (30)..(30)
<223> OTHER INFORMATION: n stands for 7-(2-thienyl)-3H-
      imidazo[4,5-b]pyridin-3-yl
<220> FEATURE:
<221> NAME/KEY: misc_feature
<222> LOCATION: (35)..(35)
<223> OTHER INFORMATION: n stands for 7-(2-thienyl)-3H-
      imidazo[4,5-b]pyridin-3-yl

<400> SEQUENCE: 33
tttcacacag gaaacagcta tgacggcccn ttacngtgcc ctatagtgag tcgtattatc         60

<210> SEQ ID NO 34
<211> LENGTH: 62
<212> TYPE: DNA
<213> ORGANISM: Artificial sequence
<220> FEATURE:
<223> OTHER INFORMATION: 62-mer DNA containing 2 Ds bases
<220> FEATURE:
<221> NAME/KEY: misc_feature
<222> LOCATION: (30)..(30)
<223> OTHER INFORMATION: n stands for 7-(2-thienyl)-3H-
      imidazo[4,5-b]pyridin-3-yl
<220> FEATURE:
<221> NAME/KEY: misc_feature
<222> LOCATION: (37)..(37)
<223> OTHER INFORMATION: n stands for 7-(2-thienyl)-3H-
      imidazo[4,5-b]pyridin-3-yl

<400> SEQUENCE: 34
tttcacacag gaaacagcta tgacggcccn ttgtacngtg ccctatagtg agtcgtatta         60
tc                                                                        62

<210> SEQ ID NO 35
<211> LENGTH: 65
<212> TYPE: DNA
<213> ORGANISM: Artificial sequence
<220> FEATURE:
<223> OTHER INFORMATION: 65-mer DNA containing 2 Ds bases
<220> FEATURE:
<221> NAME/KEY: misc_feature
<222> LOCATION: (30)..(30)
<223> OTHER INFORMATION: n stands for 7-(2-thienyl)-3H-
      imidazo[4,5-b]pyridin-3-yl
```

```
<220> FEATURE:
<221> NAME/KEY: misc_feature
<222> LOCATION: (40)..(40)
<223> OTHER INFORMATION: n stands for 7-(2-thienyl)-3H-
      imidazo[4,5-b]pyridin-3-yl

<400> SEQUENCE: 35
tttcacacag gaaacagcta tgacggcccn ttgtaatacn gtgccctata gtgagtcgta    60
ttatc                                                               65

<210> SEQ ID NO 36
<211> LENGTH: 68
<212> TYPE: DNA
<213> ORGANISM: Artificial sequence
<220> FEATURE:
<223> OTHER INFORMATION: 68-mer DNA containing 2 Ds bases
<220> FEATURE:
<221> NAME/KEY: misc_feature
<222> LOCATION: (30)..(30)
<223> OTHER INFORMATION: n stands for 7-(2-thienyl)-3H-
      imidazo[4,5-b]pyridin-3-yl
<220> FEATURE:
<221> NAME/KEY: misc_feature
<222> LOCATION: (43)..(43)
<223> OTHER INFORMATION: n stands for 7-(2-thienyl)-3H-
      imidazo[4,5-b]pyridin-3-yl

<400> SEQUENCE: 36
tttcacacag gaaacagcta tgacggcccn ttgtaacgat acngtgccct atagtgagtc    60
gtattatc                                                            68

<210> SEQ ID NO 37
<211> LENGTH: 12
<212> TYPE: DNA
<213> ORGANISM: Artificial sequence
<220> FEATURE:
<223> OTHER INFORMATION: a part of sequence complementary to the 60-mer
      DNA
<220> FEATURE:
<221> NAME/KEY: misc_feature
<222> LOCATION: (4)..(4)
<223> OTHER INFORMATION: n stands for 4-substituted 2-nitro-1H-
      pyrrol-1-yl
<220> FEATURE:
<221> NAME/KEY: misc_feature
<222> LOCATION: (9)..(9)
<223> OTHER INFORMATION: n stands for 4-substituted 2-nitro-1H-
      pyrrol-1-yl

<400> SEQUENCE: 37
cacngtaang gg                                                       12

<210> SEQ ID NO 38
<211> LENGTH: 12
<212> TYPE: DNA
<213> ORGANISM: Artificial sequence
<220> FEATURE:
<223> OTHER INFORMATION: a part of the 60-mer DNA
<220> FEATURE:
<221> NAME/KEY: misc_feature
<222> LOCATION: (4)..(4)
<223> OTHER INFORMATION: n stands for 7-(2-thienyl)-3H-
      imidazo[4,5-b]pyridin-3-yl
<220> FEATURE:
<221> NAME/KEY: misc_feature
<222> LOCATION: (9)..(9)
<223> OTHER INFORMATION: n stands for 7-(2-thienyl)-3H-
      imidazo[4,5-b]pyridin-3-yl
```

```
<400> SEQUENCE: 38
cccnttacng tg                                                          12

<210> SEQ ID NO 39
<211> LENGTH: 14
<212> TYPE: DNA
<213> ORGANISM: Artificial sequence
<220> FEATURE:
<223> OTHER INFORMATION: a part of sequence complementary to the
      62-mer DNA
<220> FEATURE:
<221> NAME/KEY: misc_feature
<222> LOCATION: (4)..(4)
<223> OTHER INFORMATION: n stands for 4-substituted 2-nitro-1H-
      pyrrol-1-yl
<220> FEATURE:
<221> NAME/KEY: misc_feature
<222> LOCATION: (11)..(11)
<223> OTHER INFORMATION: n stands for 4-substituted 2-nitro-1H-
      pyrrol-1-yl

<400> SEQUENCE: 39
cacngtacaa nggg                                                        14

<210> SEQ ID NO 40
<211> LENGTH: 14
<212> TYPE: DNA
<213> ORGANISM: Artificial sequence
<220> FEATURE:
<223> OTHER INFORMATION: a part of the 62-mer DNA
<220> FEATURE:
<221> NAME/KEY: misc_feature
<222> LOCATION: (4)..(4)
<223> OTHER INFORMATION: n stands for 7-(2-thienyl)-3H-
      imidazo[4,5-b]pyridin-3-yl
<220> FEATURE:
<221> NAME/KEY: misc_feature
<222> LOCATION: (11)..(11)
<223> OTHER INFORMATION: n stands for 7-(2-thienyl)-3H-
      imidazo[4,5-b]pyridin-3-yl

<400> SEQUENCE: 40
cccnttgtac ngtg                                                        14

<210> SEQ ID NO 41
<211> LENGTH: 17
<212> TYPE: DNA
<213> ORGANISM: Artificial sequence
<220> FEATURE:
<223> OTHER INFORMATION: a part of sequence complementary to the 65-mer
      DNA
<220> FEATURE:
<221> NAME/KEY: misc_feature
<222> LOCATION: (4)..(4)
<223> OTHER INFORMATION: n stands for 4-substituted 2-nitro-1H-
      pyrrol-1-yl
<220> FEATURE:
<221> NAME/KEY: misc_feature
<222> LOCATION: (14)..(14)
<223> OTHER INFORMATION: n stands for 4-substituted 2-nitro-1H-
      pyrrol-1-yl

<400> SEQUENCE: 41
cacngtatta caanggg                                                     17

<210> SEQ ID NO 42
<211> LENGTH: 17
<212> TYPE: DNA
<213> ORGANISM: Artificial sequence
<220> FEATURE:
<223> OTHER INFORMATION: a part of the 65-mer DNA
```

```
<220> FEATURE:
<221> NAME/KEY: misc_feature
<222> LOCATION: (4)..(4)
<223> OTHER INFORMATION: n stands for 7-(2-thienyl)-3H-
      imidazo[4,5-b]pyridin-3-yl
<220> FEATURE:
<221> NAME/KEY: misc_feature
<222> LOCATION: (14)..(14)
<223> OTHER INFORMATION: n stands for 7-(2-thienyl)-3H-
      imidazo[4,5-b]pyridin-3-yl

<400> SEQUENCE: 42
cccnttgtaa tacngtg                                                   17

<210> SEQ ID NO 43
<211> LENGTH: 20
<212> TYPE: DNA
<213> ORGANISM: Artificial sequence
<220> FEATURE:
<223> OTHER INFORMATION: a part of sequence complementary to the 68-mer
      DNA
<220> FEATURE:
<221> NAME/KEY: misc_feature
<222> LOCATION: (4)..(4)
<223> OTHER INFORMATION: n stands for 4-substituted 2-nitro-1H-
      pyrrol-1-yl
<220> FEATURE:
<221> NAME/KEY: misc_feature
<222> LOCATION: (17)..(17)
<223> OTHER INFORMATION: n stands for 4-substituted 2-nitro-1H-
      pyrrol-1-yl

<400> SEQUENCE: 43
cacngtatcg taacaanggg                                                20

<210> SEQ ID NO 44
<211> LENGTH: 20
<212> TYPE: DNA
<213> ORGANISM: Artificial sequence
<220> FEATURE:
<223> OTHER INFORMATION: a part of the 68-mer DNA
<220> FEATURE:
<221> NAME/KEY: misc_feature
<222> LOCATION: (4)..(4)
<223> OTHER INFORMATION: n stands for 7-(2-thienyl)-3H-
      imidazo[4,5-b]pyridin-3-yl
<220> FEATURE:
<221> NAME/KEY: misc_feature
<222> LOCATION: (17)..(17)
<223> OTHER INFORMATION: n stands for 7-(2-thienyl)-3H-
      imidazo[4,5-b]pyridin-3-yl

<400> SEQUENCE: 44
cccnttgtaa cgatacngtg                                                20

<210> SEQ ID NO 45
<211> LENGTH: 55
<212> TYPE: DNA
<213> ORGANISM: Artificial sequence
<220> FEATURE:
<223> OTHER INFORMATION: DNA1
<220> FEATURE:
<221> NAME/KEY: misc_feature
<222> LOCATION: (30)..(30)
<223> OTHER INFORMATION: n stands for 7-(2-thienyl)-3H-
      imidazo[4,5-b]pyridin-3-yl

<400> SEQUENCE: 45
tttcacacag gaaacagcta tgacggcccn ttgccctata gtgagtcgta ttatc          55
```

<210> SEQ ID NO 46
<211> LENGTH: 55
<212> TYPE: DNA
<213> ORGANISM: Artificial sequence
<220> FEATURE:
<223> OTHER INFORMATION: DNA2

<400> SEQUENCE: 46
tttcacacag gaaacagcta tgacacatgg aactgctata gtgagtcgta ttatc    55

<210> SEQ ID NO 47
<211> LENGTH: 55
<212> TYPE: DNA
<213> ORGANISM: Artificial sequence
<220> FEATURE:
<223> OTHER INFORMATION: DNA3

<400> SEQUENCE: 47
tttcacacag gaaacagcta tgaccatgat gcagactata gtgagtcgta ttatc    55

<210> SEQ ID NO 48
<211> LENGTH: 55
<212> TYPE: DNA
<213> ORGANISM: Artificial sequence
<220> FEATURE:
<223> OTHER INFORMATION: DNA4

<400> SEQUENCE: 48
tttcacacag gaaacagcta tgacttgatc cgtatctata gtgagtcgta ttatc    55

<210> SEQ ID NO 49
<211> LENGTH: 11
<212> TYPE: DNA
<213> ORGANISM: Artificial sequence
<220> FEATURE:
<223> OTHER INFORMATION: a part of DNA1
<220> FEATURE:
<221> NAME/KEY: misc_feature
<222> LOCATION: (6)..(6)
<223> OTHER INFORMATION: n stands for 7-(2-thienyl)-3H-
      imidazo[4,5-b]pyridin-3-yl

<400> SEQUENCE: 49
ggcccnttgc c    11

<210> SEQ ID NO 50
<211> LENGTH: 11
<212> TYPE: DNA
<213> ORGANISM: Artificial sequence
<220> FEATURE:
<223> OTHER INFORMATION: a part of DNA2

<400> SEQUENCE: 50
acatggaact g    11

<210> SEQ ID NO 51
<211> LENGTH: 11
<212> TYPE: DNA
<213> ORGANISM: Artificial sequence
<220> FEATURE:
<223> OTHER INFORMATION: a part of DNA3

<400> SEQUENCE: 51
catgatgcag a    11

<210> SEQ ID NO 52
<211> LENGTH: 11
<212> TYPE: DNA
<213> ORGANISM: Artificial sequence
<220> FEATURE:
<223> OTHER INFORMATION: a part of DNA4

<400> SEQUENCE: 52
ttgatccgta t                                                            11

<210> SEQ ID NO 53
<211> LENGTH: 11
<212> TYPE: DNA
<213> ORGANISM: Artificial sequence
<220> FEATURE:
<223> OTHER INFORMATION: complementary sequence to the part of DNA1
<220> FEATURE:
<221> NAME/KEY: misc_feature
<222> LOCATION: (6)..(6)
<223> OTHER INFORMATION: n stands for 4-substituted 2-nitro-1H-
      pyrrol-1-yl

<400> SEQUENCE: 53
ggcaangggc c                                                            11

<210> SEQ ID NO 54
<211> LENGTH: 11
<212> TYPE: DNA
<213> ORGANISM: Artificial sequence
<220> FEATURE:
<223> OTHER INFORMATION: complementary sequence to the part of DNA2

<400> SEQUENCE: 54
cagttccatg t                                                            11

<210> SEQ ID NO 55
<211> LENGTH: 11
<212> TYPE: DNA
<213> ORGANISM: Artificial sequence
<220> FEATURE:
<223> OTHER INFORMATION: complementary sequence to the part of DNA3

<400> SEQUENCE: 55
tctgcatcat g                                                            11

<210> SEQ ID NO 56
<211> LENGTH: 11
<212> TYPE: DNA
<213> ORGANISM: Artificial sequence
<220> FEATURE:
<223> OTHER INFORMATION: complementary sequence to the part of DNA4

<400> SEQUENCE: 56
atacggatca a                                                            11

<210> SEQ ID NO 57
<211> LENGTH: 6
<212> TYPE: PRT
<213> ORGANISM: Artificial sequence
<220> FEATURE:
<223> OTHER INFORMATION: Histidine tag

<400> SEQUENCE: 57

His His His His His His
1               5

```
<210> SEQ ID NO 58
<211> LENGTH: 8
<212> TYPE: PRT
<213> ORGANISM: Artificial sequence
<220> FEATURE:
<223> OTHER INFORMATION: FLAG tag

<400> SEQUENCE: 58

Asp Tyr Lys Asp Asp Asp Asp Lys
1               5

<210> SEQ ID NO 59
<211> LENGTH: 10
<212> TYPE: PRT
<213> ORGANISM: Artificial sequence
<220> FEATURE:
<223> OTHER INFORMATION: MYC tag

<400> SEQUENCE: 59

Glu Gln Lys Leu Ile Ser Glu Glu Asp Leu
1               5                   10

<210> SEQ ID NO 60
<211> LENGTH: 49
<212> TYPE: DNA
<213> ORGANISM: Artificial sequence
<220> FEATURE:
<223> OTHER INFORMATION: DNA sequence recited in Figure 3
<220> FEATURE:
<221> NAME/KEY: misc_feature
<222> LOCATION: (23)..(25)
<223> OTHER INFORMATION: n stands for adenine, guanine, thymine, or
      cytosine
<220> FEATURE:
<221> NAME/KEY: misc_feature
<222> LOCATION: (26)..(26)
<223> OTHER INFORMATION: n stands for 4-substituted 2-nitro-1H-
      pyrrol-1-yl
<220> FEATURE:
<221> NAME/KEY: misc_feature
<222> LOCATION: (27)..(29)
<223> OTHER INFORMATION: n stands for adenine, guanine, thymine, or
      cytosine

<400> SEQUENCE: 60
gataatacga ctcactatag ggnnnnnnnc cgtcatagct gtttcctgt          49

<210> SEQ ID NO 61
<211> LENGTH: 41
<212> TYPE: DNA
<213> ORGANISM: Artificial sequence
<220> FEATURE:
<223> OTHER INFORMATION: DNA sequence recited in Figure 4(a) and Figure
      5-2
<220> FEATURE:
<221> NAME/KEY: misc_feature
<222> LOCATION: (26)..(26)
<223> OTHER INFORMATION: n stands for 4-substituted 2-nitro-1H-
      pyrrol-1-yl
<220> FEATURE:
<221> NAME/KEY: misc_feature
<222> LOCATION: (27)..(28)
<223> OTHER INFORMATION: n stands for adenine, guanine, thymine, or
      cytosine
<220> FEATURE:
<221> NAME/KEY: misc_feature
<222> LOCATION: (33)..(33)
<223> OTHER INFORMATION: n stands for adenine, guanine, thymine, or
      cytosine
<220> FEATURE:
<221> NAME/KEY: misc_feature
<222> LOCATION: (35)..(35)
<223> OTHER INFORMATION: n stands for adenine, guanine, thymine, or
      cytosine
```

```
<220> FEATURE:
<221> NAME/KEY: misc_feature
<222> LOCATION: (38)..(39)
<223> OTHER INFORMATION: n stands for adenine, guanine, thymine, or
      cytosine

<400> SEQUENCE: 61
gataatacga ctcactatag ggcaannntc ccncntannt g                          41

<210> SEQ ID NO 62
<211> LENGTH: 42
<212> TYPE: DNA
<213> ORGANISM: Artificial sequence
<220> FEATURE:
<223> OTHER INFORMATION: DNA sequence recited in Figure 4(b) and Figure
      5-2
<220> FEATURE:
<221> NAME/KEY: misc_feature
<222> LOCATION: (26)..(26)
<223> OTHER INFORMATION: n stands for 4-substituted 2-nitro-1H-
      pyrrol-1-yl
<220> FEATURE:
<221> NAME/KEY: misc_feature
<222> LOCATION: (32)..(32)
<223> OTHER INFORMATION: n stands for adenine, guanine, thymine, or
      cytosine

<400> SEQUENCE: 62
gataatacga ctcactatag ggcaangggc cngtcatagc tg                         42

<210> SEQ ID NO 63
<211> LENGTH: 7
<212> TYPE: DNA
<213> ORGANISM: Artificial sequence
<220> FEATURE:
<223> OTHER INFORMATION: DNA sequence recited in Figure 5-1, lanes 8 and
      13

<400> SEQUENCE: 63 atccatt                                                                 7

<210> SEQ ID NO 64
<211> LENGTH: 43
<212> TYPE: DNA
<213> ORGANISM: Artificial sequence
<220> FEATURE:
<223> OTHER INFORMATION: DNA sequence recited in Figure 5-2
<220> FEATURE:
<221> NAME/KEY: misc_feature
<222> LOCATION: (26)..(26)
<223> OTHER INFORMATION: n stands for adenine, guanine, thymine, or
      cytosine
<220> FEATURE:
<221> NAME/KEY: misc_feature
<222> LOCATION: (27)..(27)
<223> OTHER INFORMATION: n stands for 4-substituted 2-nitro-1H-
      pyrrol-1-yl
<220> FEATURE:
<221> NAME/KEY: misc_feature
<222> LOCATION: (28)..(39)
<223> OTHER INFORMATION: n stands for adenine, guanine, thymine, or
      cytosine
<220> FEATURE:
<221> NAME/KEY: misc_feature
<222> LOCATION: (41)..(42)
<223> OTHER INFORMATION: n stands for adenine, guanine, thymine, or
      cytosine

<400> SEQUENCE: 64
gataatacga ctcactatag ggcaannnnn nnnnnnnnnc nnc                        43
```

```
<210> SEQ ID NO 65
<211> LENGTH: 42
<212> TYPE: DNA
<213> ORGANISM: Artificial sequence
<220> FEATURE:
<223> OTHER INFORMATION: DNA sequence recited in Figure 5-2
<220> FEATURE:
<221> NAME/KEY: misc_feature
<222> LOCATION: (26)..(26)
<223> OTHER INFORMATION: n stands for 4-substituted 2-nitro-1H-
      pyrrol-1-yl
<220> FEATURE:
<221> NAME/KEY: misc_feature
<222> LOCATION: (32)..(32)
<223> OTHER INFORMATION: n stands for adenine, guanine, thymine, or
      cytosine

<400> SEQUENCE: 65
gataatacga ctcactatag ggcaangtac cngtcatagc tg                         42

<210> SEQ ID NO 66
<211> LENGTH: 42
<212> TYPE: DNA
<213> ORGANISM: Artificial sequence
<220> FEATURE:
<223> OTHER INFORMATION: DNA sequence recited in Figure 5-2
<220> FEATURE:
<221> NAME/KEY: misc_feature
<222> LOCATION: (26)..(26)
<223> OTHER INFORMATION: n stands for 4-substituted 2-nitro-1H-
      pyrrol-1-yl
<220> FEATURE:
<221> NAME/KEY: misc_feature
<222> LOCATION: (27)..(30)
<223> OTHER INFORMATION: n stands for adenine, guanine, thymine, or
      cytosine
<220> FEATURE:
<221> NAME/KEY: misc_feature
<222> LOCATION: (33)..(34)
<223> OTHER INFORMATION: n stands for adenine, guanine, thymine, or
      cytosine
<220> FEATURE:
<221> NAME/KEY: misc_feature
<222> LOCATION: (36)..(42)
<223> OTHER INFORMATION: n stands for adenine, guanine, thymine, or
      cytosine

<400> SEQUENCE: 66
gataatacga ctcactatag ggatannnnn ccnncnnnnn nn                         42

<210> SEQ ID NO 67
<211> LENGTH: 41
<212> TYPE: DNA
<213> ORGANISM: Artificial sequence
<220> FEATURE:
<223> OTHER INFORMATION: DNA sequence recited in Figure 5-2
<220> FEATURE:
<221> NAME/KEY: misc_feature
<222> LOCATION: (26)..(26)
<223> OTHER INFORMATION: n stands for 4-substituted 2-nitro-1H-
      pyrrol-1-yl

<400> SEQUENCE: 67
gataatacga ctcactatag ggatangatc cgtcatagct g                          41

<210> SEQ ID NO 68
<211> LENGTH: 46
<212> TYPE: DNA
<213> ORGANISM: Artificial sequence
<220> FEATURE:
<223> OTHER INFORMATION: DNA sequence recited in Figure 6
```

```
<220> FEATURE:
<221> NAME/KEY: misc_feature
<222> LOCATION: (26)..(26)
<223> OTHER INFORMATION: n stands for 4-substituted 2-nitro-1H-
      pyrrol-1-yl
<220> FEATURE:
<221> NAME/KEY: misc_feature
<222> LOCATION: (31)..(31)
<223> OTHER INFORMATION: n stands for 4-substituted 2-nitro-1H-
      pyrrol-1-yl

<400> SEQUENCE: 68
gataatacga ctcactatag ggcacngtaa ngggccgtca tagctg            46

<210> SEQ ID NO 69
<211> LENGTH: 46
<212> TYPE: DNA
<213> ORGANISM: Artificial sequence
<220> FEATURE:
<223> OTHER INFORMATION: DNA sequence recited in Figure 6
<220> FEATURE:
<221> NAME/KEY: misc_feature
<222> LOCATION: (26)..(26)
<223> OTHER INFORMATION: n stands for 4-substituted 2-nitro-1H-
      pyrrol-1-yl
<220> FEATURE:
<221> NAME/KEY: misc_feature
<222> LOCATION: (33)..(33)
<223> OTHER INFORMATION: n stands for 4-substituted 2-nitro-1H-
      pyrrol-1-yl

<400> SEQUENCE: 69
gataatacga ctcactatag ggcacngtac aangggccgt catagc            46

<210> SEQ ID NO 70
<211> LENGTH: 46
<212> TYPE: DNA
<213> ORGANISM: Artificial sequence
<220> FEATURE:
<223> OTHER INFORMATION: DNA sequence recited in Figure 6
<220> FEATURE:
<221> NAME/KEY: misc_feature
<222> LOCATION: (26)..(26)
<223> OTHER INFORMATION: n stands for 4-substituted 2-nitro-1H-
      pyrrol-1-yl
<220> FEATURE:
<221> NAME/KEY: misc_feature
<222> LOCATION: (36)..(36)
<223> OTHER INFORMATION: n stands for 4-substituted 2-nitro-1H-
      pyrrol-1-yl

<400> SEQUENCE: 70
gataatacga ctcactatag ggcacngtat tacaangggc cgtcat            46

<210> SEQ ID NO 71
<211> LENGTH: 46
<212> TYPE: DNA
<213> ORGANISM: Artificial sequence
<220> FEATURE:
<223> OTHER INFORMATION: DNA sequence recited in Figure 6
<220> FEATURE:
<221> NAME/KEY: misc_feature
<222> LOCATION: (26)..(26)
<223> OTHER INFORMATION: n stands for 4-substituted 2-nitro-1H-
      pyrrol-1-yl
<220> FEATURE:
<221> NAME/KEY: misc_feature
<222> LOCATION: (39)..(39)
<223> OTHER INFORMATION: n stands for 4-substituted 2-nitro-1H-
      pyrrol-1-yl

<400> SEQUENCE: 71
gataatacga ctcactatag ggcacngtat cgttacaang gccgt             46
```

```
<210> SEQ ID NO 72
<211> LENGTH: 41
<212> TYPE: DNA
<213> ORGANISM: Artificial sequence
<220> FEATURE:
<223> OTHER INFORMATION: DNA sequence recited in Figure 7
<220> FEATURE:
<221> NAME/KEY: misc_feature
<222> LOCATION: (21)..(31)
<223> OTHER INFORMATION: n stands for adenine, guanine, thymine, or
      cytosine

<400> SEQUENCE: 72
gataatacga ctcactatag nnnnnnnnnn ngtcatagct g                              41

<210> SEQ ID NO 73
<211> LENGTH: 41
<212> TYPE: DNA
<213> ORGANISM: Artificial sequence
<220> FEATURE:
<223> OTHER INFORMATION: DNA sequence recited in Figure 7
<220> FEATURE:
<221> NAME/KEY: misc_feature
<222> LOCATION: (26)..(26)
<223> OTHER INFORMATION: n stands for 4-substituted 2-nitro-1H-
      pyrrol-1-yl

<400> SEQUENCE: 73
gataatacga ctcactatag ggcaangggc cgtcatagct g                              41

<210> SEQ ID NO 74
<211> LENGTH: 43
<212> TYPE: DNA
<213> ORGANISM: Artificial sequence
<220> FEATURE:
<223> OTHER INFORMATION: DNA sequence recited in Figure 8
<220> FEATURE:
<221> NAME/KEY: misc_feature
<222> LOCATION: (25)..(25)
<223> OTHER INFORMATION: n stands for 4-substituted 2-nitro-1H-
      pyrrol-1-yl

<400> SEQUENCE: 74
ataatacgac tcactatagg gcaangggcc gtcatagctg ttt                            43
```